United States Patent
Aoki et al.

(10) Patent No.: US 10,893,795 B2
(45) Date of Patent: Jan. 19, 2021

(54) CAMERA SYSTEM FOR MONITORING INSIDE OF BODY AND AUXILIARY TOOL SET

(71) Applicant: Sharp Kabushiki Kaisha, Sakai (JP)

(72) Inventors: Hitoshi Aoki, Sakai (JP); Toshihisa Gotoh, Sakai (JP); Kei Urakawa, Sakai (JP)

(73) Assignee: Sharp Kabushiki Kaisha, Sakai (JP)

( * ) Notice: Subject to any disclaimer, the term of this patent is extended or adjusted under 35 U.S.C. 154(b) by 388 days.

(21) Appl. No.: 15/112,726

(22) PCT Filed: Jan. 20, 2015

(86) PCT No.: PCT/JP2015/051408
§ 371 (c)(1),
(2) Date: Jul. 20, 2016

(87) PCT Pub. No.: WO2015/111582
PCT Pub. Date: Jul. 30, 2015

(65) Prior Publication Data
US 2016/0338573 A1 Nov. 24, 2016

(30) Foreign Application Priority Data

Jan. 23, 2014 (JP) .................. 2014-010749
Dec. 16, 2014 (JP) .................. 2014-254476

(51) Int. Cl.
*A61B 1/04* (2006.01)
*A61B 17/34* (2006.01)
(Continued)

(52) U.S. Cl.
CPC .......... *A61B 1/041* (2013.01); *A61B 1/00112* (2013.01); *A61B 1/00114* (2013.01);
(Continued)

(58) Field of Classification Search
CPC ......... A61B 1/00147; A61B 1/04; A61B 1/05; A61B 1/313; A61B 1/3132;
(Continued)

(56) References Cited

U.S. PATENT DOCUMENTS

2008/0309758 A1 12/2008 Karasawa et al.
2011/0046440 A1 2/2011 Asada et al.
(Continued)

FOREIGN PATENT DOCUMENTS

EP 2 130 483 A1 12/2009
EP 2 471 435 A1 7/2012
(Continued)

OTHER PUBLICATIONS

Aoki et al., "Camera System for Monitoring Inside of Body", U.S. Appl. No. 15/546,291, filed Jul. 26, 2017.
(Continued)

*Primary Examiner* — Ryan N Henderson
(74) *Attorney, Agent, or Firm* — Keating & Bennett, LLP

(57) ABSTRACT

A camera system for monitoring the inside of a body having excellent work efficiency is suggested. The camera system for monitoring the inside of a body includes: a cable (12) in which one end is connected to the imaging part; a first auxiliary tool (8) which is connected to the other end of the cable (12); and a second auxiliary tool (7) which includes a holding unit (7g) which holds a held unit (8g) provided in the first auxiliary tool (8), and a rod-like unit (7x) connected to the holding unit (7g), and which draws out the held unit (8g) toward the outside of the body from the inside of the body through the inside of a tube-like device (6) of which one end is guided toward the inside of the body, in a state of being held by the holding unit (7g).

12 Claims, 40 Drawing Sheets

(51) Int. Cl.
*A61B 1/00* (2006.01)
*A61B 90/00* (2016.01)
*A61B 1/313* (2006.01)
*A61B 17/00* (2006.01)

(52) U.S. Cl.
CPC ...... *A61B 1/00147* (2013.01); *A61B 1/00158* (2013.01); *A61B 1/313* (2013.01); *A61B 1/3132* (2013.01); *A61B 17/3421* (2013.01); *A61B 90/361* (2016.02); *A61B 2017/00283* (2013.01); *A61B 2017/00477* (2013.01)

(58) Field of Classification Search
CPC ........ A61B 2017/00283; A61B 5/6861; A61B 2562/162
See application file for complete search history.

(56) References Cited

U.S. PATENT DOCUMENTS

| | | |
|---|---|---|
| 2012/0016198 A1 | 1/2012 | Takahashi et al. |
| 2016/0143510 A1 | 5/2016 | Gotoh et al. |

FOREIGN PATENT DOCUMENTS

| | | | | |
|---|---|---|---|---|
| JP | 4472727 B2 | 6/2010 | | |
| JP | 4599474 B1 | 12/2010 | | |
| JP | 2012239519 A | * 12/2012 | ............... | A61B 1/41 |
| WO | 2012/008188 A1 | 1/2012 | | |
| WO | 2015/020124 A1 | 2/2015 | | |
| WO | 2015/064743 A1 | 5/2015 | | |
| WO | 2015/080148 A1 | 6/2015 | | |
| WO | 2015/080293 A1 | 6/2015 | | |
| WO | 2015/107848 A1 | 7/2015 | | |

OTHER PUBLICATIONS

Gotoh et al., "In-Body Monitoring Camera System and Support Tube for In-Body Monitoring-Camera-System", U.S. Appl. No. 14/899,269, filed Dec. 17, 2015.

Inoue et al., "In-Vivo Monitoring Camera System, and Support Tube for In-Vivo Monitoring Camera System", U.S. Appl. No. 15/031,777, filed Apr. 25, 2016.

Urakawa et al., "Intracorporeal-Monitoring Camera System, Support Tube for Intracorporeal-Monitoring Camera System, and Cable Holder for Intracorporeal-Monitoring Camera System", U.S. Appl. No. 14/917,064, filed Mar. 7, 2016.

Urakawa et al., "Camera System for Monitoring Inside of Body, Accessory for Support Tube of Camera System for Monitoring Inside of Body, Fixing Tool for Camera System for Monitoring Inside of Body, and Method for Installing Camera System for Monitoring Inside of Body", U.S. Appl. No. 15/031,816, filed Apr. 25, 2016.

Aoki et al., "Camera System for Monitoring Inside of Body and Auxiliary Device and Method for Installing Imaging Apparatus for Monitoring Inside of Body", U.S. Appl. No. 15/111,514, filed Jul. 14, 2016.

Aoki et al., "In-Body Monitoring Camera System and Camera Unit", U.S. Appl. No. 15/129,044, filed Sep. 26, 2016.

* cited by examiner

FIG. 9
(a)
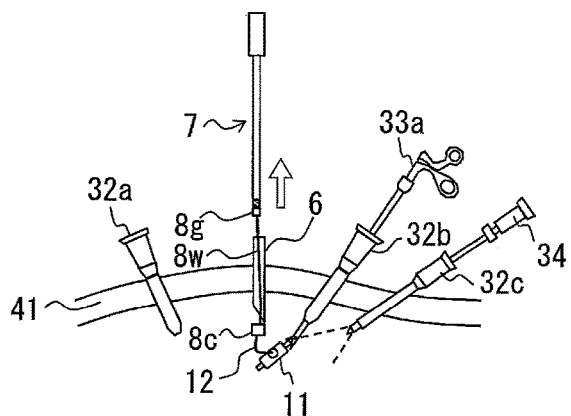
(b)
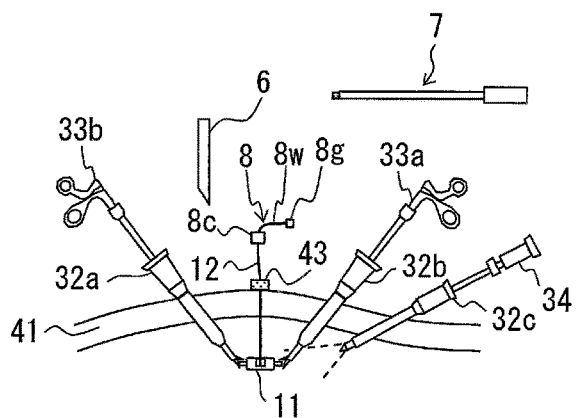
6: PUNCTURING TOOL
7: DRAWING TOOL
8: CONNECTOR PROTECTION CAP HAVING MAGNET
8g: MAGNET
8c: CAP UNIT
8w: LINKING WIRE
11: CAMERA UNIT
12: CAMERA SIDE CABLE
32a to 32c: TROCAR
33a, 33b: FORCEPS
34: ENDOSCOPE
41: BODY WALL
43: CABLE FASTENER FIG. 11
(a)
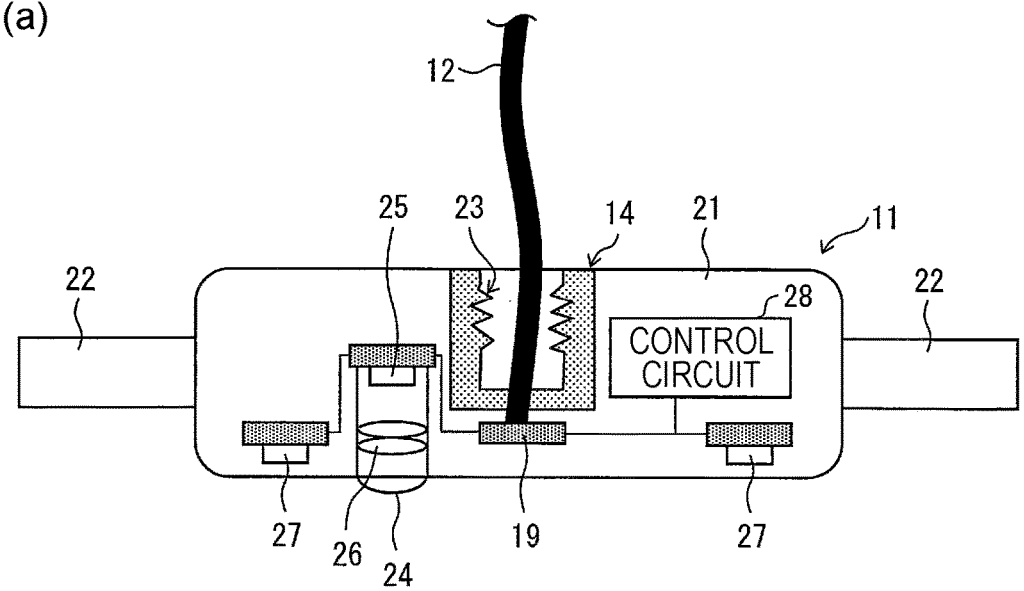
(b)
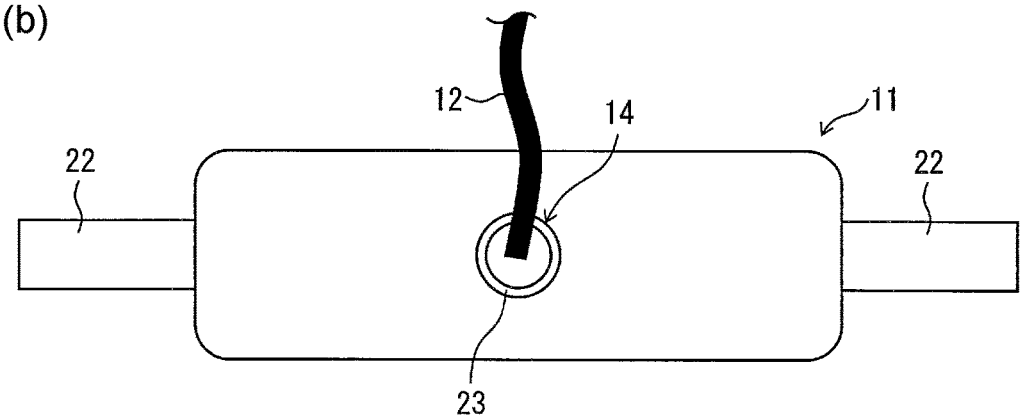
11: CAMERA UNIT
12: CAMERA SIDE CABLE
14: SUPPORT TUBE JOINING UNIT
19: CIRCUIT BOARD
21: CAMERA HOUSING
22: SUPPORT UNIT
23: LOCKING FEMALE SCREW
24: IMAGING UNIT
25: SOLID IMAGING ELEMENT
26: LENS
27: ILLUMINATION APPARATUS
28: CONTROL CIRCUIT

FIG. 15

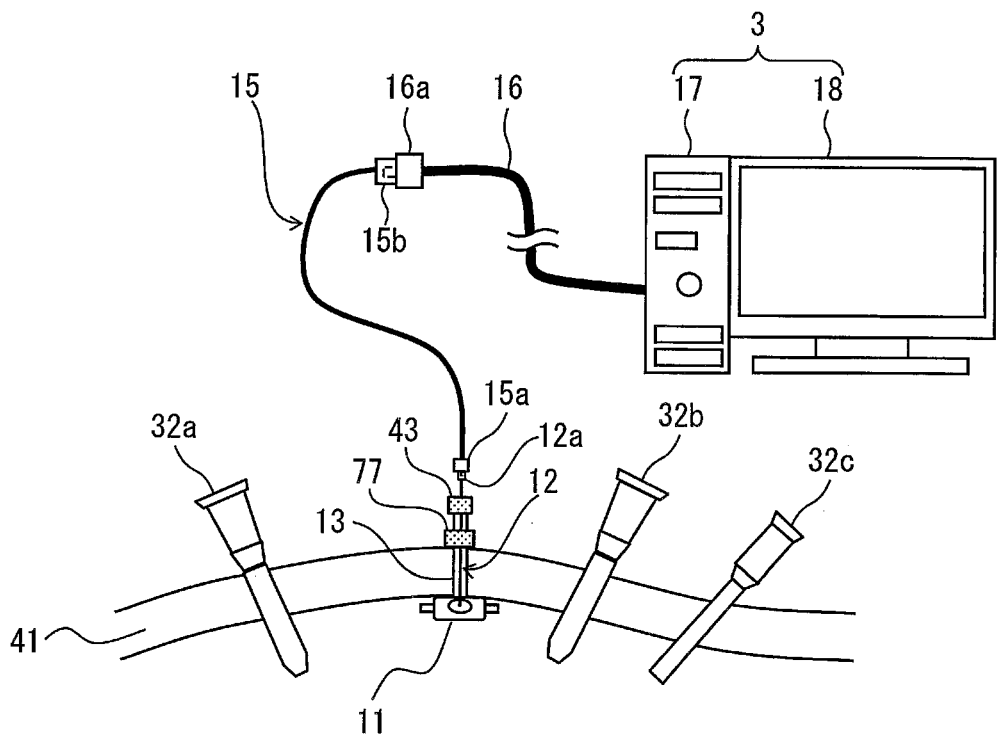

3: CONTROL SYSTEM
11: CAMERA UNIT
12: CAMERA SIDE CABLE
12a: CAMERA SIDE CABLE CONNECTOR
13: CAMERA SUPPORT TUBE
15: INTERMEDIATE CABLE
15a: FIRST INTERMEDIATE CABLE CONNECTOR
    (CAMERA SIDE)
15b: SECOND INTERMEDIATE CABLE CONNECTOR
    (EQUIPMENT SIDE)
16: EQUIPMENT SIDE CABLE
16a: EQUIPMENT SIDE CABLE CONNECTOR
17: CAMERA UNIT CONTROL EQUIPMENT
18: DISPLAY
32a to 32c: TROCAR
33a, 33b: FORCEPS
34: ENDOSCOPE
41: BODY WALL
43: CABLE FASTENER
77: STOPPER

FIG. 19

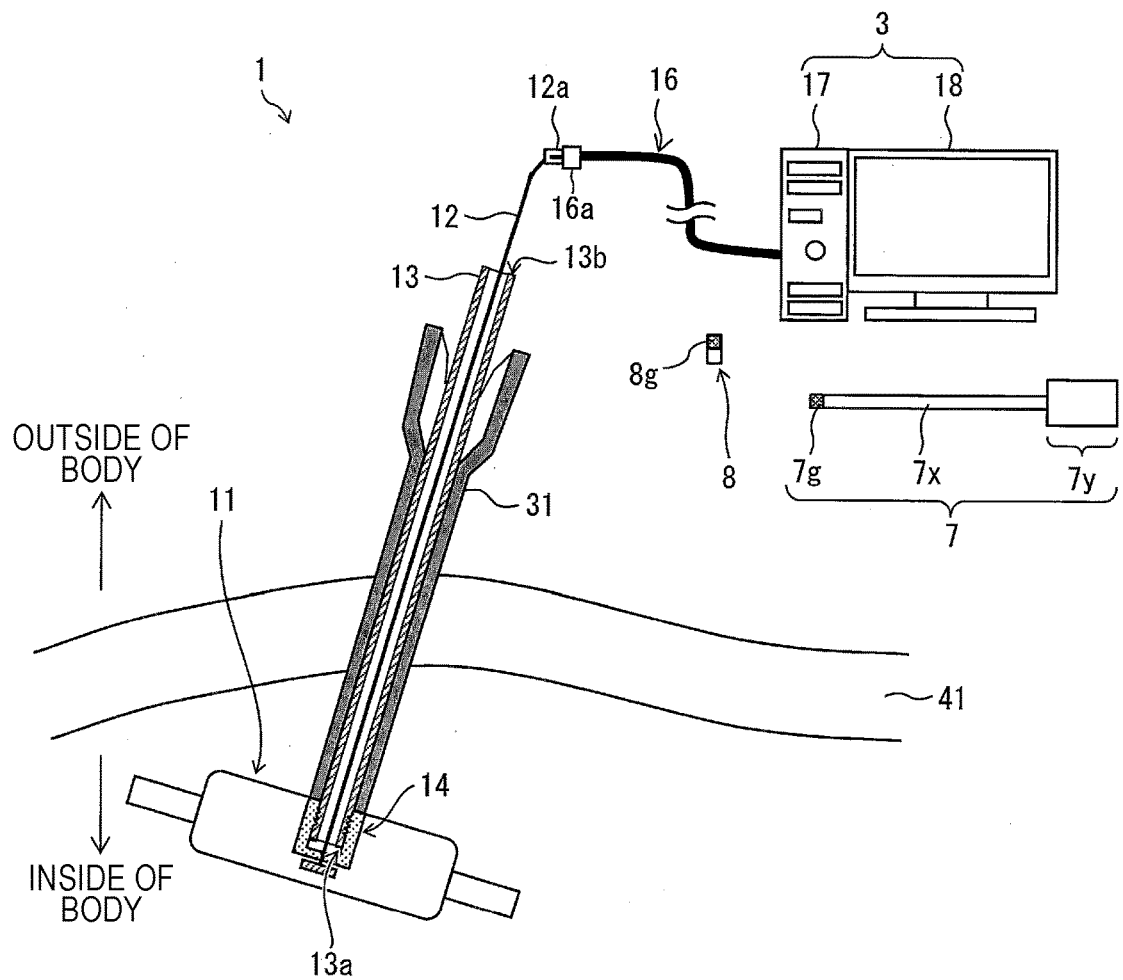

1: CAMERA SYSTEM FOR MONITORING INSIDE OF BODY
3: CONTROL SYSTEM
6: PUNCTURING TOOL (TUBE-LIKE TOOL)
7: DRAWING TOOL (SECOND AUXILIARY TOOL)
7x: ROD-LIKE UNIT
7y: HANDLE UNIT
7g: MAGNET (HOLDING UNIT)
8: CONNECTOR PROTECTION CAP HAVING MAGNET (FIRST AUXILIARY TOOL)
8g: MAGNET (HELD UNIT)
11: CAMERA UNIT
12: CAMERA SIDE CABLE
12a: CAMERA SIDE CABLE CONNECTOR
13: CAMERA SUPPORT TUBE
13a: END PART
13b: END PART
16: EQUIPMENT SIDE CABLE
16a: EQUIPMENT SIDE CABLE CONNECTOR
17: CAMERA UNIT CONTROL EQUIPMENT
18: DISPLAY
31: CANNULA (TUBE-LIKE DEVICE)
41: BODY WALL

CAMERA SYSTEM FOR MONITORING INSIDE OF BODY AND AUXILIARY TOOL SET

TECHNICAL FIELD

The present invention relates to a camera system for monitoring the inside of a body provided with an imaging part which can be guided toward the inside of a body.

BACKGROUND ART

Endoscopic surgery is minimally invasive surgery for performing examination or medical treatment without laparotomy with respect to a patient. In the endoscopic surgery, a treatment tool, such as forceps, and an endoscope are separately guided toward the inside of a body cavity of the patient, and a practitioner captures an image of a tip end part of the treatment tool inserted into the body cavity within an observation visual field of the endoscope, and performs the treatment operation while observing a treatment state of the patient by the treatment tool using the endoscope. In the endoscopic surgery, the treatment tool and the endoscope are guided toward the inside of the body cavity through a pipe punctured through a body wall (for example, an abdominal wall) in an abdomen or the like of the patient. In addition, the pipe is a tube-like member which is a so-called trocar.

The practitioner enlarges the image by making the endoscope approach an organ, and performs incision or suturing of the organ, but at this time, the visual field of the practitioner becomes extremely narrow. Therefore, an apparatus which can widely grasp a state outside the work region (for example, the movement of the treatment tool, a bleeding state, and a remaining state of a residual, such as gauze, outside a work region), is required.

Corresponding to such a request, in PTL 1, an apparatus which directly inserts a needle-like connector electrode into an abdominal wall, and joins the connector electrode and a camera to each other in a body, or reversely an apparatus which inserts the needle-like connector electrode into the abdominal wall from the inside of the body, and joins the connector electrode and the camera to each other on the outside of the body, is disclosed.

In PTL 2, an apparatus which inserts a camera unit and a communication cable which joins with the camera unit from a trocar, draws out a hooking needle and the communication cable from an abdominal wall hole toward the outside of a body in a state where an end part of the communication cable is hooked to the hooking needle inserted from the abdominal wall hole, and fixes the communication cable, is disclosed.

CITATION LIST

Patent Literature

PTL 1: Japanese Patent No. 4472727 (issued on Jun. 2, 2010)
PTL 2: Japanese Patent No. 4599474 (issued on Dec. 15, 2010)

SUMMARY OF INVENTION

Technical Problem

According to PTL 1, it becomes necessary that the needle-like connector electrode pierces through the abdominal wall, and the connector electrode and the camera are connected to each other on the inside of the body.

In PTL 2, it becomes necessary that the hooking needle pierces through the abdominal wall, and work of taking out the hooking needle and the communication cable toward the outside of the body through the abdominal hole in a state where the end part of the communication cable is hooked to the hooking needle is performed. In this case, there is a concern that the communication cable comes off of the needle in the abdominal wall.

Considering the above-described problems, an object of the present invention is to suggest a camera system for monitoring the inside of a body which has excellent work efficiency.

Solution to Problem

In order to solve the above-described problems, there is provided a camera system for monitoring the inside of a body according to an aspect of the present invention, including: an imaging part for monitoring the inside of a body; a control system which is provided on the outside of the body, and includes at least a display apparatus; a cable in which one end is connected to the imaging unit; a first auxiliary tool which is connected to the other end of the cable; and a second auxiliary tool which includes a holding unit which holds a held unit provided in the first auxiliary tool, and a rod-like unit connected to the holding unit, and which draws out the held unit toward the outside of the body from the inside of the body through the inside of a tube-like device in which one end is guided toward the inside of the body, in a state of being held by the holding unit.

Advantageous Effects of Invention

According to one aspect of the present invention, by drawing out the held unit of the first auxiliary tool toward the outside of the body from the inside of the body through the inside of the tube-like device in which one end is guided toward the inside of the body, in a state of being held by the holding unit of the second auxiliary tool, it is possible to easily guide the other end of the cable toward the outside of the body, and work efficiency is improved.

BRIEF DESCRIPTION OF DRAWINGS

FIG. 3(a) is a view of the puncturing device, FIG. 3(b) is a sectional view of FIG. 3(a), FIG. 3(c) is a view of an obturator which is used in puncturing by being combined with the puncturing device, and FIG. 3(d) is a sectional view illustrating a state where the obturator passes through the puncturing device.

FIG. 4(a) is a view of a drawing tool and a connector protection cap having a magnet, FIG. 4(b) is a sectional view in which the drawing tool is inserted into the puncturing device, FIG. 4(c) is a view illustrating a state where a stopper which fixes the drawing tool is added to FIG. 4(b), and FIG. 4(d) is a view illustrating a state where the drawing tool is pushed into the puncturing device. In addition, FIG. 4(e) is a view illustrating an example of the connector protection cap having a magnet, and FIG. 4(f) is a view illustrating a connector unit of a camera cable.

FIG. 5(a) is a view in which the connector protection cap having a magnet is mounted on a camera cable connector unit, and FIGS. 5(b) and 5(c) are views respectively illustrating a section taken along line A-A' and a section taken along line B-B' of FIG. 5(a). In addition, FIG. 5(d) is a view illustrating a state where the drawing tool and the connector protection cap having a magnet are mounted and inserted into the puncturing device. FIG. 5(e) is a view illustrating another example of the connector protection cap having a magnet, and FIG. 5(f) is a view illustrating a state where the drawing tool and the connector protection cap having a magnet of FIG. 5(e) are mounted and inserted into the puncturing device.

FIG. 6(a) is a view illustrating still another example of the connector protection cap having a magnet, FIG. 6(b) is a view illustrating a state where the drawing tool and the magnet connected to the connector protection cap having a magnet of FIG. 6(a) are adhered and inserted into the puncturing device, and FIG. 6(c) is a view illustrating a state where a magnet connected to the connector protection cap having a magnet is drawn out toward the outside of the body through the puncturing device.

FIG. 9(a) is a schematic view illustrating a modification example with respect to the process of FIG. 7(d), and FIG. 9(b) is a schematic view illustrating a modification example with respect to the process of FIG. 8(a).

FIG. 11(a) is a sectional view schematically illustrating a schematic configuration of main parts of an imaging apparatus according to Embodiment 2, and FIG. 11(b) is an upper view of the imaging apparatus illustrated in FIG. 11(a).

FIG. 15 is a schematic view illustrating a modification example with respect to the process of FIG. 14(d).

FIG. 16(a) is a sectional view illustrating each of sections of the puncturing device used as the camera support tube and the camera unit support tube joining unit illustrated in FIG. 11(a), and FIG. 16(b) is a sectional view illustrating a joined state of the puncturing device used as the camera support tube and the support tube joining unit which are illustrated in FIG. 16(a). FIG. 16(c) is a view illustrating a connected state by adding the camera unit and a camera side cable to FIG. 16(b). FIG. 16(d) is a view illustrating an example in which the puncturing device is fixed to the camera unit by using a cable fastener, and FIG. 16(e) is another example in which the fixing is performed by using the cable fastener.

FIG. 19 is a schematic view illustrating a schematic configuration of a camera system for monitoring the inside of a body according to Embodiment 3.

FIG. 24(a) is a view of the drawing tool having a whisk-like tip end part and a connector protection cap having a magnet and a hooking tool, FIG. 24(b) is a sectional view illustrating a state where the whisk-like tip end part is accommodated in a pipe-shaped rod-like unit, FIG. 24(c) is a view illustrating a state where the puncturing device is used instead of the pipe-shaped rod-like unit with respect to FIG. 24(a), and FIG. 24(d) is a view illustrating a state where the whisk-like tip end part is accommodated in the puncturing device.

FIG. 28(a) is a plan view of a joining surface of the magnet having a projected joining unit, FIG. 28(b) is a sectional view taken along line G-G' of FIG. 28(a), FIG. 28(c) is a plan view of a joining surface of the magnet having a recessed joining unit, FIG. 28(d) is a sectional view taken along line H-H' of FIG. 28(c), and FIG. 28(e) is a view illustrating a state where the projected joining unit and the recessed joining unit are fitted to each other.

FIG. 29(a) is a view illustrating an example in which the magnet is directly attached to the connector protection cap having a magnet, and FIG. 29(b) is a view illustrating a state where the drawing tool and the connector protection cap having a magnet of FIG. 29(a) are adhered and inserted into the puncturing device. FIG. 29(c) is a view illustrating another example of the connector protection cap having a magnet in which the magnet is connected by a linking wire, and FIG. 29(d) is a view illustrating a state where the drawing tool and the connector protection cap having a magnet of FIG. 29(c) are adhered and inserted into the puncturing device.

DESCRIPTION OF EMBODIMENTS

Embodiment 1

Camera System for Monitoring Inside of Body

Figure 1:
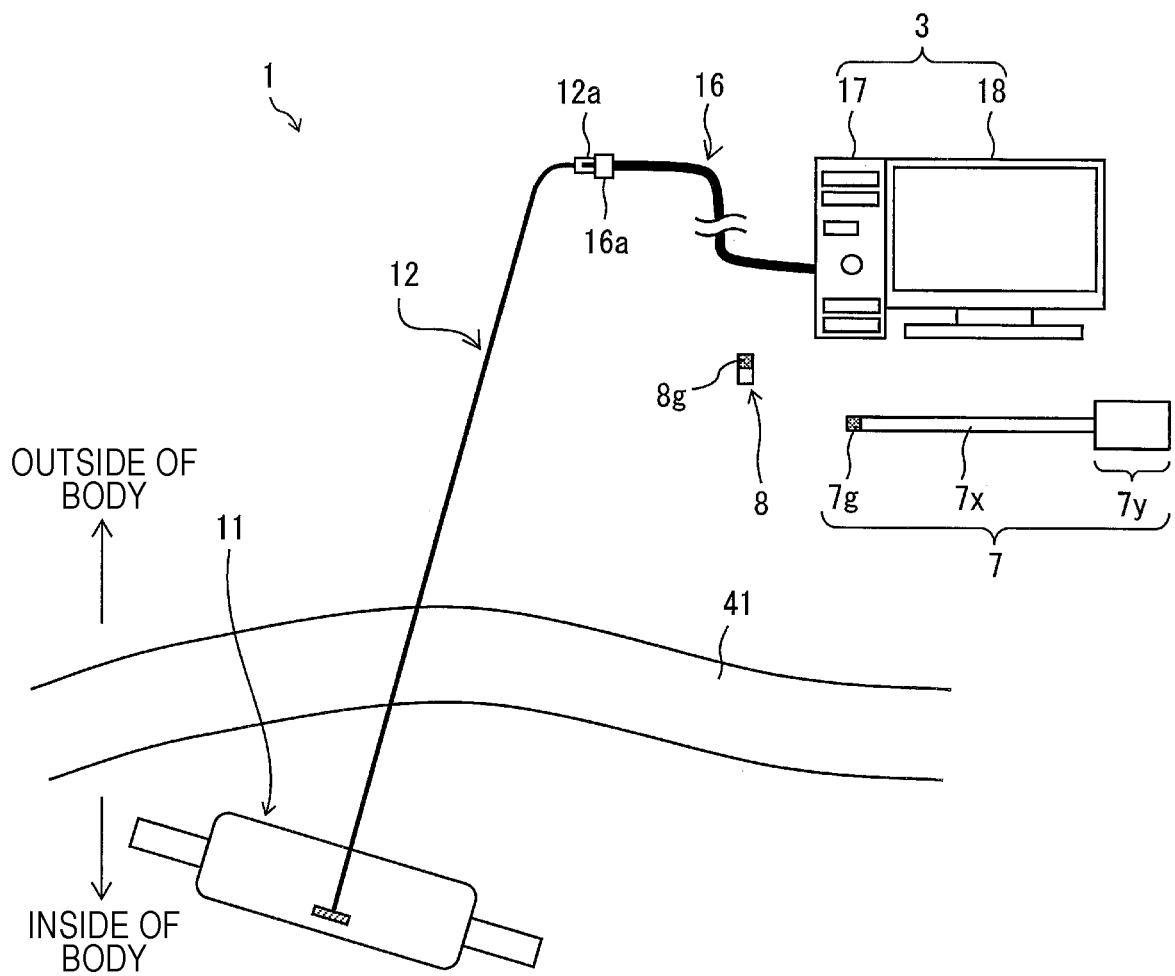
FIG. 1 is a schematic view illustrating a schematic configuration of a camera system for monitoring the inside of a body according to Embodiment 1.

FIG. 1 is a schematic view illustrating a schematic configuration of a camera system for monitoring the inside of a body 1 according to an embodiment.

As illustrated in FIG. 1, the camera system for monitoring the inside of a body 1 according to the embodiment is provided with a camera unit 11 (imaging part) which captures the inside of the body, a camera side cable 12 in which one end is connected to the camera unit 11, a control system 3 including a display 18 (display unit), an equipment side cable 16 in which one end is connected to the control system 3, a connector protection cap having a magnet 8 (first auxiliary tool) connected to the other end of the camera side cable 12, and a drawing tool 7 (second auxiliary tool) which includes a rod-like unit 7x connected to a magnet 7g (holding unit) which holds a magnet 8g (held unit) provided in the connector protection cap having a magnet 8, and a magnet 7g, and which draws out the magnet 8g toward the outside of the body from the inside of the body through the inside of a tube-like device in a state of being held by the magnet 7g. In addition, an equipment side cable connector 16a (projected type) provided at the other end of the equipment side cable 16 is fitted to a camera side cable connector 12a (recessed type) provided at the other end of the camera side cable 12, and the camera unit 11 and the control system 3 are electrically connected to each other. In addition, hereinafter, there is a case where the camera side cable connector 12a is briefly referred to as a connector 12a, and the equipment side cable connector 16a is briefly referred to as a connector 16a.

In addition, in FIG. 1, the number of pins inserted into the camera side cable connector 12a is set to be 1, but for simplification, in general, the number of pins becomes the number of pins which corresponds to the number of electric wires used as the cable. This is also similar in other drawings.

<Camera Unit>

Figure 2:
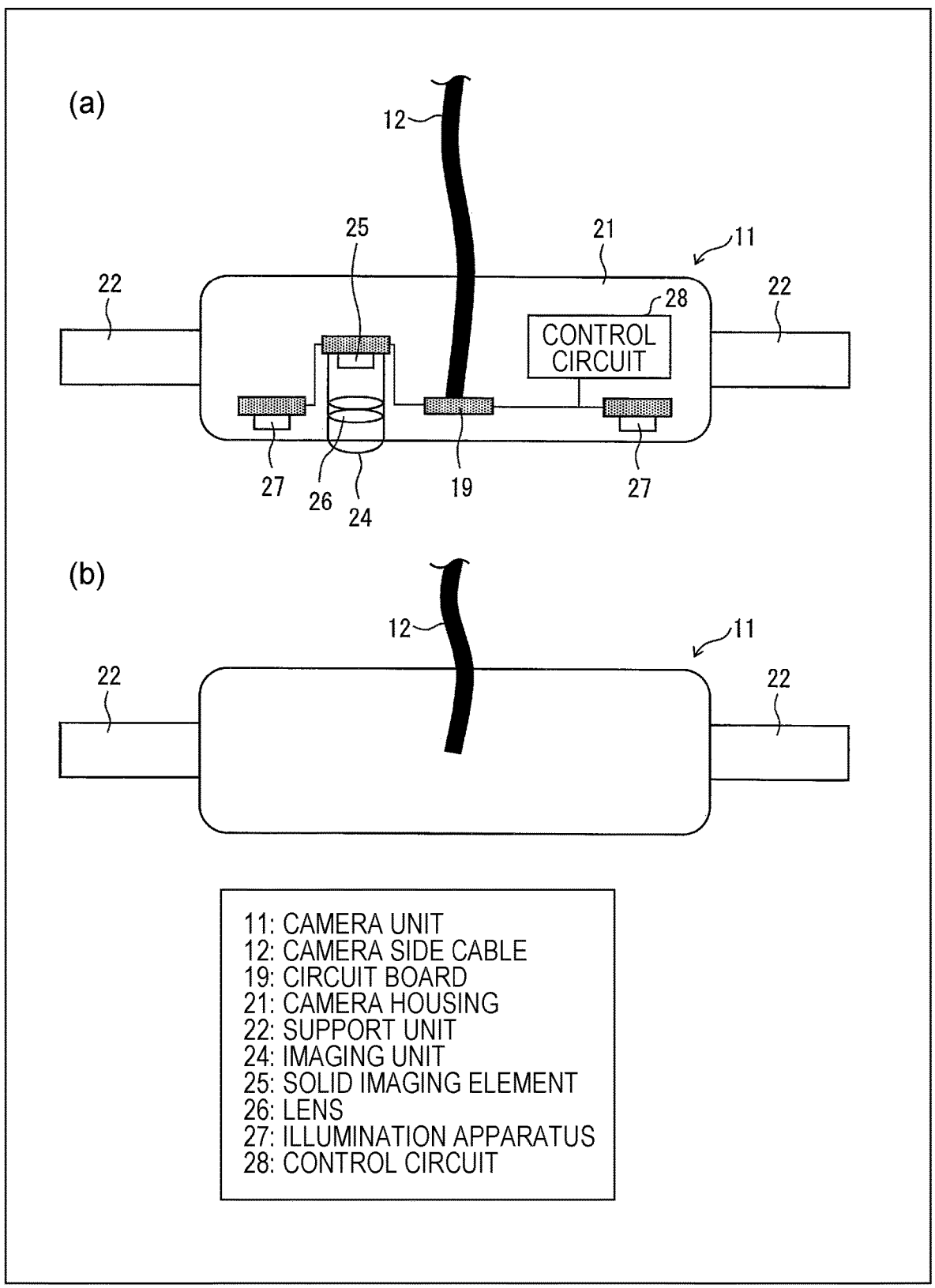
FIG. 2(a) is a sectional view schematically illustrating a schematic configuration of a camera unit according to Embodiment 1.
FIG. 2(b) is an upper view of the camera unit illustrated in FIG. 2(a).

FIG. 2(a) is a sectional view schematically illustrating a schematic configuration of main parts of the camera unit 11, and FIG. 2(b) is an upper view of the camera unit 11.

As illustrated in FIGS. 1, 2(a), and 2(b), the camera unit 11 is provided with a camera housing 21, a circuit board 19, an imaging unit 24, a control circuit 28, an illumination apparatus 27, and a support unit 22.

The circuit board 19, the imaging unit 24, the control circuit 28, and the illumination apparatus 27 are provided in the camera housing 21. Meanwhile, the support unit 22 is provided on the outer side of the camera housing 21.

The imaging unit 24 is provided with a lens 26 which is an imaging lens, and a solid-state imaging element 25. The solid-state imaging element 25 is disposed so that an optical axis and an axial center of the lens 26 match each other. Examples of the solid-state imaging element 25 include a charge coupled device (CCD) or a complementary metal-oxide semiconductor (CMOS) image sensors. The illumination apparatus 27 makes an image captured by the camera unit 11 clear by illuminating the inside of the body. It is preferable that the size of the illumination apparatus 27 is small, and for example, a light emitting diode (LED) or the like can be appropriately used. In addition, in the camera unit 11, only one illumination apparatus 27 may be provided, or a plurality of illumination apparatuses 27 may be provided as illustrated in FIG. 2(a).

The solid-state imaging element 25, the illumination apparatus 27, and the control circuit 28 are connected to the circuit board 19. The control circuit 28 is electrically connected to the imaging unit 24 and the illumination apparatus 27 via the circuit board 19.

In addition, one end part of the camera side cable 12 is connected to the circuit board 19, and a signal is input and output between the circuit board 19 and a camera unit control equipment 17 (refer to FIG. 1) in the control system 3 via the camera side cable 12 and the connectors 12a and 16a (refer to FIG. 1). Accordingly, the control circuit 28 controls the driving of the imaging unit 24 and the illumination apparatus 27 based on a control signal input from the camera unit control equipment 17 via the camera side cable 12 and the circuit board 19.

Since a wired method is employed in transfer from the camera unit 11 to the camera unit control equipment 17, when the speed of the transfer increases, stable sending and receiving of the signal becomes possible, and an image having a high resolution can be obtained. In addition, it is possible to perform communication at low power compared to a wireless method, and to reduce the size of the camera unit 11 by supplying power from the outside. By reducing the size, it is possible to minimize damage small when the camera unit 11 is guided toward the inside of the body, and there is a special effect that minimal invasiveness is improved.

Next, the camera housing 21 and the support unit 22 which is provided on the outside of the camera housing 21 will be described.

Figure 7:
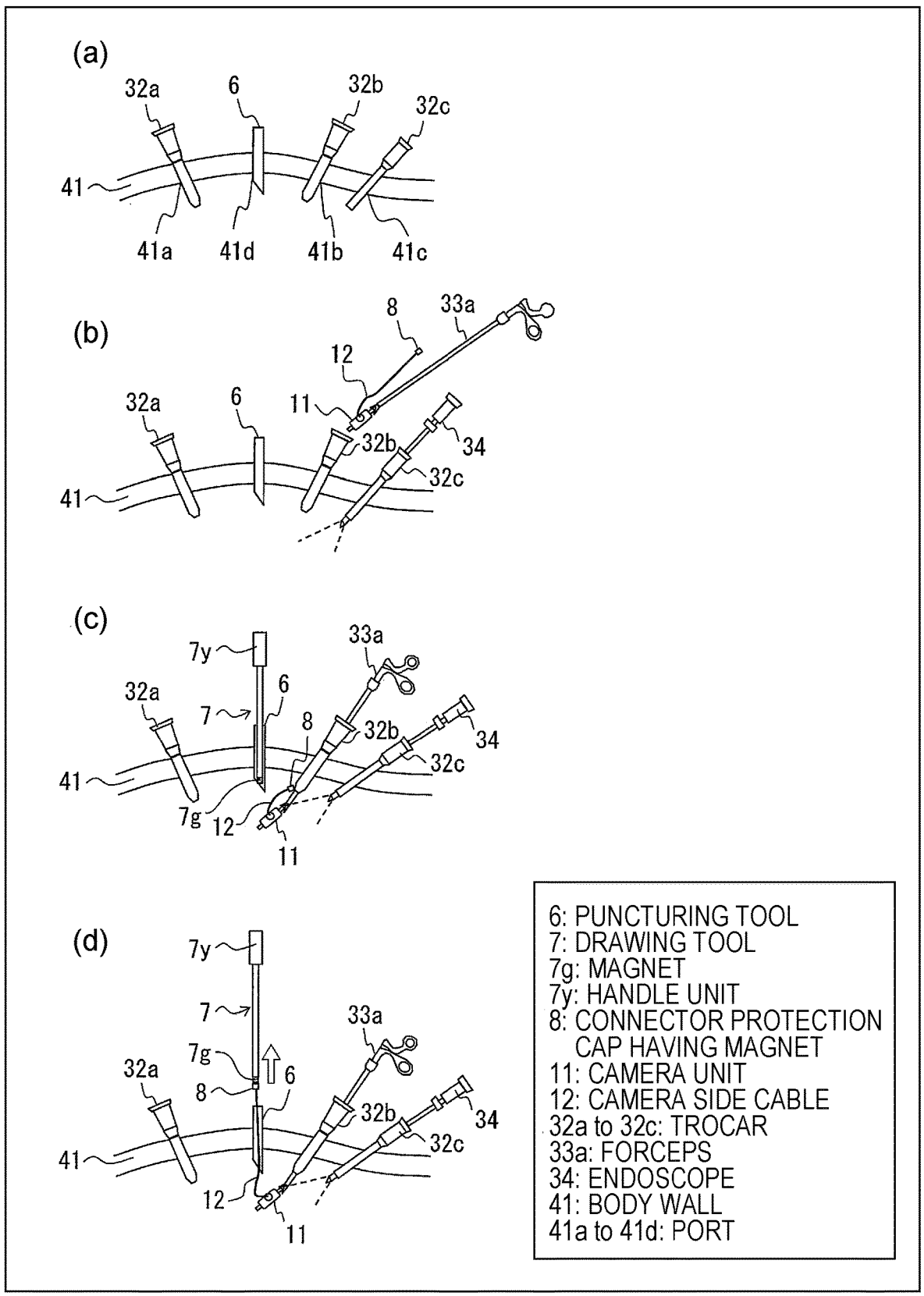
FIGS. 7(a) to 7(d) are schematic views illustrating a method for installing the imaging apparatus in the camera system for monitoring the inside of a body according to Embodiment 1, in a process order.

The support unit 22 is provided to protrude outward from each of both side surfaces which oppose each other in the camera housing 21. The support unit 22 is used as a gripping unit in the camera unit 11. The camera unit 11 passes through, for example, a trocar 32 (tube-like member, refer to FIG. 7), and is guided toward the inside of the body. The support unit 22 is for supporting the camera unit 11. When the camera unit 11 is guided toward the inside of the body from the trocar 32 by using forceps, when the camera unit is taken out of the support tube after being used, or when the camera unit is collected from the trocar, the support unit 22 is gripped, and can support the camera unit 11.

In addition, a part at which the lens 26 or the illumination apparatus 27 is disposed in the camera housing 21 of the camera unit 11 is configured of a transparent material, but it is desirable that other parts (including the support unit 22) are configured of a material having a blue color, a blue-green color, or a green color of a cold color system which is easily noticed on the inside of the body. In this manner, by using a blue color, a blue-green color, or a green color of the cold color system which are in a relationship of complementary colors with respect to the color of the inside of the body which is red or yellow, visual recognition can be easily performed when installation work or collection work which will be described later are performed on the inside of the body. Accordingly, by making the camera unit 11 blue, blue-green, or green, a special effect that it is possible to reduce the time for the installation work of the camera unit 11, and stability also increases, is achieved.

In addition, as described above, other than performing the coloring using a blue color or a green color, a light-storing material or a reflective material which are likely to be visually recognized may be used. According to this, when an object is in a shadow of an organ which is unlikely to be visually recognized, or at an end of a visual field to which illumination light is unlikely to reach, it is possible to directly find the object, and thus, the light-storing material or the reflective material is particularly effective.

<Control System>

As illustrated in FIG. 1, the control system 3 is provided with the camera unit control equipment 17 and a display 18 (display apparatus). The camera unit control equipment 17 displays the image sent from the camera unit 11 on the display 18. In addition, the camera unit control equipment 17 sends the control signal to the camera unit 11. In addition, the camera unit control equipment 17 and the display 18 may be integrated with each other, or may be configured as separate bodies.

<Cable>

The camera side cable 12 is a communication cable on a camera side. The camera side cable 12 sends the image captured by the camera unit 11 to the camera unit control equipment 17 via the connectors 12a and 16a and the equipment side cable 16 as an image signal, or sends the control signal from the camera unit control equipment 17 to the camera unit 11. In addition, a power source supply line for supplying the power to the camera unit 11 may be included in the camera side cable 12.

One end part of the camera side cable 12 is connected to the circuit board 19, and is guided toward the outside of the camera unit 11. In addition, the connection unit of the circuit board 19 and the camera side cable 12 is sealed by a resin or the like which is not illustrated. Furthermore, at a part where the camera side cable 12 is drawn out, the camera side cable 12 is adhered and fixed to the camera housing 21. An example of adhering and fixing includes sealing and fixing using an adhesive or an O-ring. Infiltration and incorporation of foreign substances into the camera unit 11 from the adhered and fixed part, are prevented.

Figure 3:
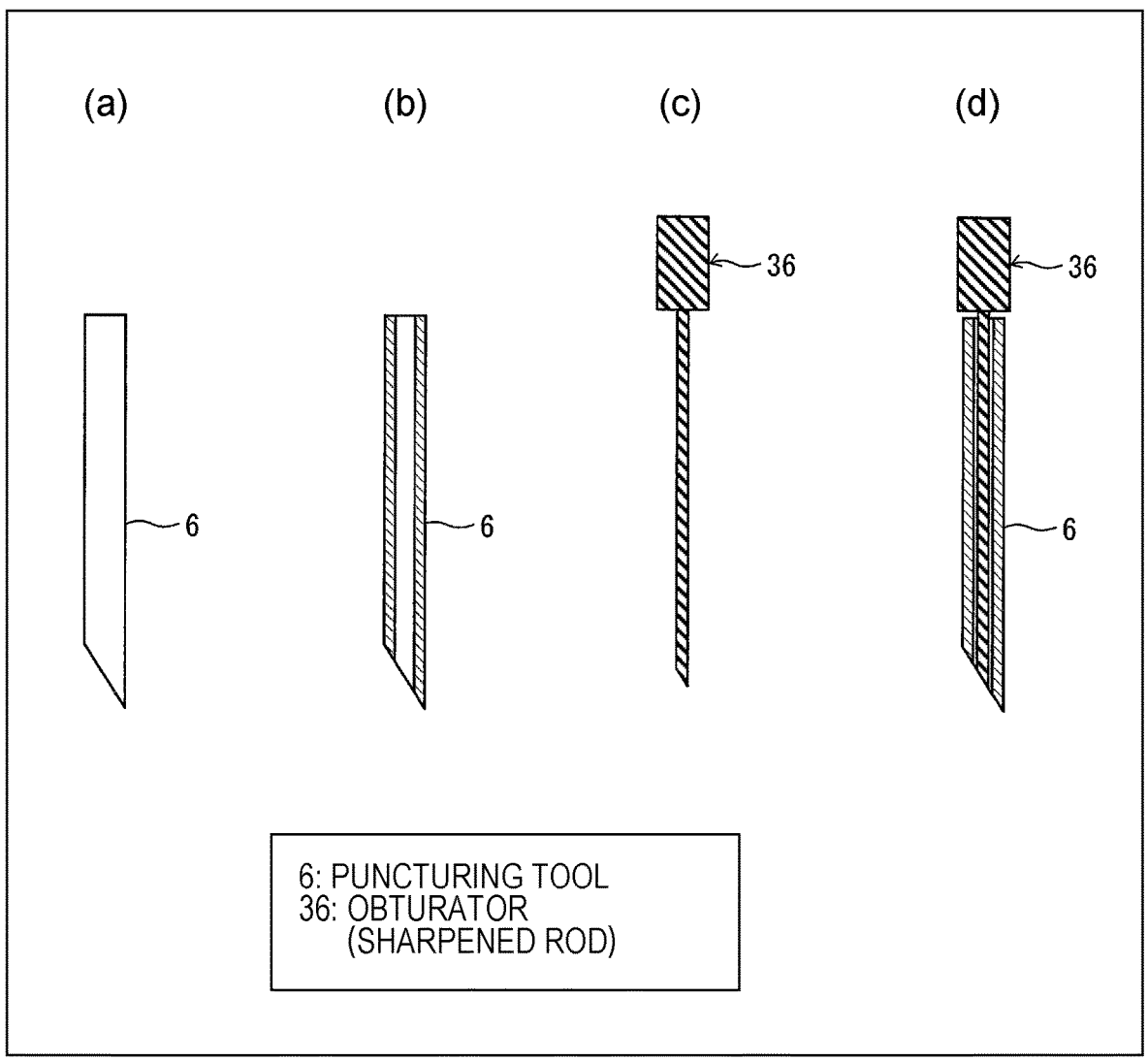
FIGS. 3(a) to 3(d) are views illustrating an example of a puncturing device according to Embodiment 1.

The camera side cable 12 passes through the tube-like member, such as the trocar 32 (refer to FIG. 7), in a state of being connected to the camera unit 11 and is guided toward the inside of a body cavity, or passes through a puncturing device 6 (refer to FIG. 3) or the camera support tube 13 (refer to FIG. 12) which will be described later and is drawn out toward the outside of the body. Therefore, the camera side cable 12 is formed of a flexible material having ductility.

In addition, it is described that it is desirable that the camera housing 21 is configured of a blue color, a blue-green color, or a green color of the cold color system which is easily noticed on the inside of the body. However, similarly, it is more desirable that a film of a surface of the camera side cable 12 is configured of a material having a blue color, a blue-green color, or a green color, which is easily noticed on the inside of the body. Furthermore, it is desirable that the camera side cable connector 12a is configured of a material which is similarly colored. In this manner, by using a blue color, a blue-green color, or a green color of the cold color system which are in a relationship of complementary colors with respect to the color of the inside of the body which is red or yellow, visual recognition can be easily performed when the installation work or the collection work which will be described later are performed on the inside of the body. For example, even when the camera unit 11 is mistakenly dropped on the inside of the body and is hidden by the shadow of the organ, since the camera side cable 12 is long compared to the camera unit 11, there are many cases where the camera side cable 12 is seen at a location which can be visually recognized, and the camera side cable 12 is likely to be found immediately. Therefore, by making the camera side cable 12 blue, blue-green, or green, a special effect that it is possible to reduce the time for the installation work of the camera unit 11, and stability also increases, is achieved.

In this manner, in making the camera housing 21 or the camera side cable 12 blue, it is possible to use a color (color which is easily seen on the inside of the body) which corresponds to visible light having a wavelength of 420 nm to 570 nm (more preferably, 450 nm to 530 nm).

In addition, as described above, other than performing the coloring using a blue material or a green material, the light-storing material or the reflective material which is likely to be visually recognized may be used. According to this, when an object is in a shadow of an organ which is unlikely to be visually recognized, or at an end of a visual field to which illumination light is unlikely to reach, it is possible to directly find the object, and thus, the light-storing material or the reflective material is particularly effective.

In FIG. 1, by inserting a pin part of the male type (projected type) equipment side cable connector 16a into the female type (recessed type) camera side cable connector 12a, both cable connectors are fitted to each other, but the invention is not limited thereto. A configuration in which the male type and the female type are reverse to each other, and the male type (projected type) camera side cable connector and the male type (recessed type) equipment side cable connector are fitted to each other, may be employed. In addition, in a case where the female type (recessed type) camera side cable connector is used, even in a case where the connector protection cap mistakenly comes off, and a terminal part is exposed, the male type pin part is not exposed to the outside, and thus, dust is unlikely to be adhered even in a case where the inside of the body is mistakenly touched. Therefore, it is desirable that the female type (recessed) cable connector is used on the camera side.

In addition, as will be described later, since the camera side cable 12 and the camera side cable connector 12a return to the inside of the body when collecting the camera unit 11, it is necessary that the equipment side cable connector 16a to be in contact and a part of the equipment side cable 16 on the equipment side cable connector 16a side to be touched by a clean hand, are maintained to be clean.

Figure 31:
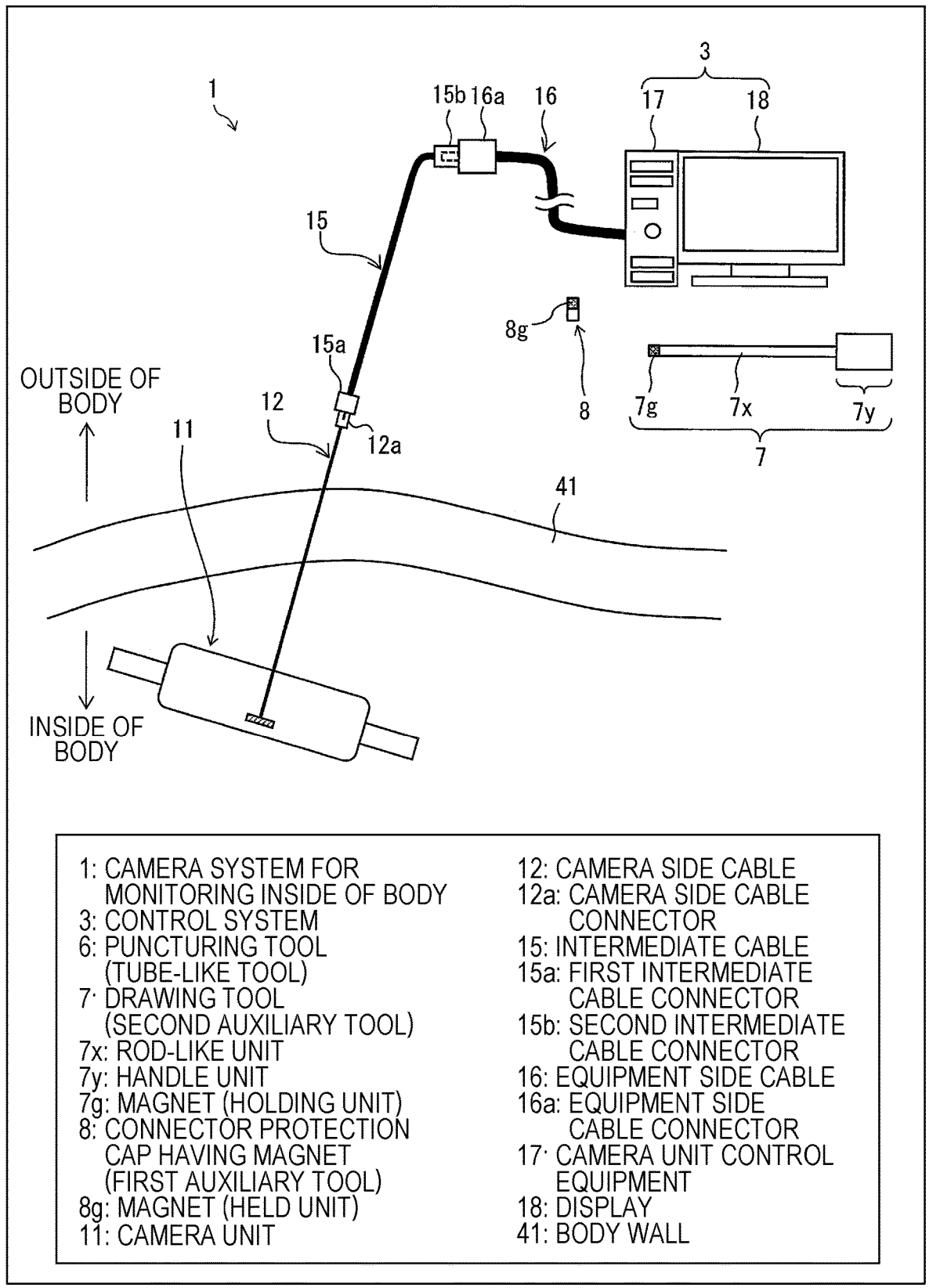
FIG. 31 is a schematic view illustrating an additional configuration of the camera system for monitoring the inside of a body according to Embodiment 1.

In addition, as illustrated in FIG. 31, it is desirable that an intermediate cable 15 is provided between the camera side cable 12 and the equipment side cable 16. Specifically, the pin part of a first intermediate cable connector 15a (projected type) provided at one end of the intermediate cable 15, is inserted into the camera side cable connector 12a (recessed type), and the pin part of the equipment side cable connector 16a (projected type) is inserted into a second intermediate cable connector 15b (recessed type) provided at the other end of the intermediate cable 15. In this manner, it is possible to gradually change the cable diameter of the fine camera side cable 12, the cable diameter of the thick equipment side cable 16, or the thickness of the cable connector, and to make the necessity of use of the fine cable which is comparatively slow in the transferring speed, the lowest limit. Accordingly, high-speed transfer becomes possible, and an image having a high resolution can be obtained. Hereinafter, there is a case where the first intermediate cable connector 15a is briefly referred to as a connector 15a, and the second intermediate cable connector 15b is briefly referred to as a connector 15b.

In a case where the cable diameter or the thickness of the cable connector gradually changes, as illustrated in FIG. 31, it is desirable that "the outer diameter of the camera side cable 12<the outer diameter of the intermediate cable 15<the outer diameter of the equipment side cable 16", and "the outer diameter of the camera side cable connector 12a≤the outer diameter of the first intermediate cable connector 15a<the outer diameter of the second intermediate cable connector 15b≤the outer diameter of the equipment side cable connector 16a".

In addition, by using the intermediate cable 15, there is a special effect that separation of a clean field and an unclean field during the surgery is effectively performed. In other words, in order to make the handling easy regarding the above-described transfer speed or during the installation, the camera side cable 12 is set to have a length which is the lowest necessary limit, and from here, until entering the unclean field beyond the clean field, the intermediate cable 15 to which sterilization treatment has already been performed, is used. According to this, the camera side cable connector 12a and the first intermediate cable connector 15a can be fitted to each other in the middle of the clean field, and a clean state can be maintained. Meanwhile, the second intermediate cable connector 15b is fitted to the equipment side cable connector 16a of the equipment side cable 16 which is unclean, and becomes unclean, and the second intermediate cable connector 15b is handled as an unclean device. Therefore, it is possible to completely separate the unclean device from the clean device side.

In addition, at a part included in the "clean field" in the camera system for monitoring the inside of a body, the sterilization treatment is performed and cleanness is maintained. Meanwhile, at a part included in the "unclean field", the sterilization treatment is not performed, and the part becomes a part which enters the "unclean field" after performing the sterilization treatment.

In addition, it is desirable that connection strength (fitting strength) when connecting (fitting) the camera side cable connector 12a, and the equipment side cable connector 16a or the first intermediate cable connector 15a, is set to be smaller than adhering strength of the adhering and fixing unit of the camera side cable 12 and the camera unit 11.

This is because, when an unexpected large force is applied to the cable in a normal use, by releasing the connection (FIG. 1) of the connectors 12a and 16a or the connection (FIG. 31) of the connectors 12a and 15a in advance, there is not a concern that the adhering and fixing unit of the camera side cable 12 is damaged or the body wall of a patient is damaged as the camera unit 11 is pulled in the direction toward the outside of the body, and the stability is improved. In addition, it is also possible to prevent an accident caused when the practitioner or an assistant is hooked by the cable and falls down, or the camera unit control equipment 17 is pulled and dropped from the table.

For example, it is desirable that the connection strength of the connectors 12a and 16a (FIG. 1) is equal to or less than 30 N (newton) which is less than the adhering strength of the adhering and fixing unit. Furthermore, it is desirable that the most appropriate range is set to be a range of 4 N to 10 N. When the range is set, it is possible to perform the connection without recklessly applying a large force when performing the connection, and, even when performing the removing, it is not necessary to recklessly apply a large force.

In addition, in FIG. 31, if the connection strength of the equipment side cable 16 and the camera unit control equipment 17 by the cable connector (not illustrated) which is on the camera unit control equipment 17 side in the equipment side cable 16, or the connection strength of the equipment side cable connector 16a which is in the unclean field and the second intermediate cable connector 15b, is set (for example, 50 N to 100 N) to be greater than the connection strength of the camera side cable connector 12a and the first intermediate cable connector 15a, when an unexpected force is applied to the cable, the connection (fitting of the connectors 12a and 15a) of the camera side cable 12 which is in the clean field and the intermediate cable 15 can be necessarily released in advance. In an opposite case, if the connection (connectors 15b and 16a) of the intermediate cable 15 which is in the unclean field and the equipment side cable 16 comes off in advance, as a reaction, a risk that a part which is in the unclean field of the intermediate cable 15, and the second intermediate cable connector 15b enter the clean field, is generated. Therefore, releasing the connection (fitting of connectors 12a and 15a) in the clean field, has a special effect in ensuring safety during surgery.

In addition, in a case where the connection comes off in the clean field, a part which is in the clean field of the intermediate cable 15, that is, the first intermediate cable connector 15a, and a part (clean part) having a predetermined length from the first intermediate cable connector 15a, are touched by the unclean field, the intermediate cable may be exchanged with a clean intermediate cable (including the first intermediate cable connector), and thus, safety is ensured. In addition, in a case where the first intermediate cable connector is configured of an independent single component (can be exchanged as a single body), and in a case where the first intermediate cable connector is touched by the unclean field together with a part which is in the clean field of the intermediate cable, the first intermediate cable connector and the intermediate cable can be exchanged with a clean one.

In addition, it is desirable that the camera side cable 12 is sufficiently short compared to the length (approximately 1 m) made by adding the lengths of the camera side cable 12 and the clean part. Specifically, it is desirable that the length of the camera side cable 12 is equal to or less than half of the length made by adding the lengths of the camera side cable 12 and the clean part, that is, the length of the camera side cable 12 is a maximum of 50 cm. Accordingly, it is possible to prevent the camera side cable 12 from entering the unclean field.

In the above-described description, a case where the camera side cable 12 and the equipment side cable 16 are connected to each other by the intermediate cable 15 is described, but as illustrated in FIG. 1, even in a case where the camera side cable 12 and the equipment side cable 16 are directly connected to each other, it is desirable that the camera side cable 12 is sufficiently short compared to the length (approximately 1 m) made by adding the lengths of the camera side cable 12 and the clean part (the equipment side cable connector 16a, and a part having a predetermined length from the equipment side cable connector 16a) of the equipment side cable 16.

<Auxiliary Tool Set>

The camera system for monitoring the inside of a body 1 according to the embodiment is provided with the connector protection cap having a magnet 8 which is the first auxiliary tool, and the drawing tool 7 which is the second auxiliary tool, as an auxiliary tool set, and the auxiliary tool set is, for example, a tube-like device, and is used together with the trocar or the cannula, or the puncturing device.

A structure of the puncturing device will be described in detail with reference to FIGS. 3(a) to 3(d). FIG. 3(a) is a view illustrating an example of the puncturing device 6 (tube-like member) according to the embodiment, FIG. 3(b) is a sectional view of FIG. 3(a), FIG. 3(c) is a view of an obturator (sharpened rod) which is used in puncturing by being combined with the puncturing device, and FIG. 3(d) is a sectional view illustrating a state where the obturator passes through the puncturing device. In general, the puncturing device, such as the trocar, has a sharp tip end, has a pipe-like hollow structure having a cavity on the inside thereof, and is used by passing through and being combined with the obturator 36 when puncturing is performed. Hereinafter, a puncturing device which has a tip end, such as an injection needle, will be described as an example.

(Drawing Tool and Connector Protection Cap Having Magnet)

Figure 4:
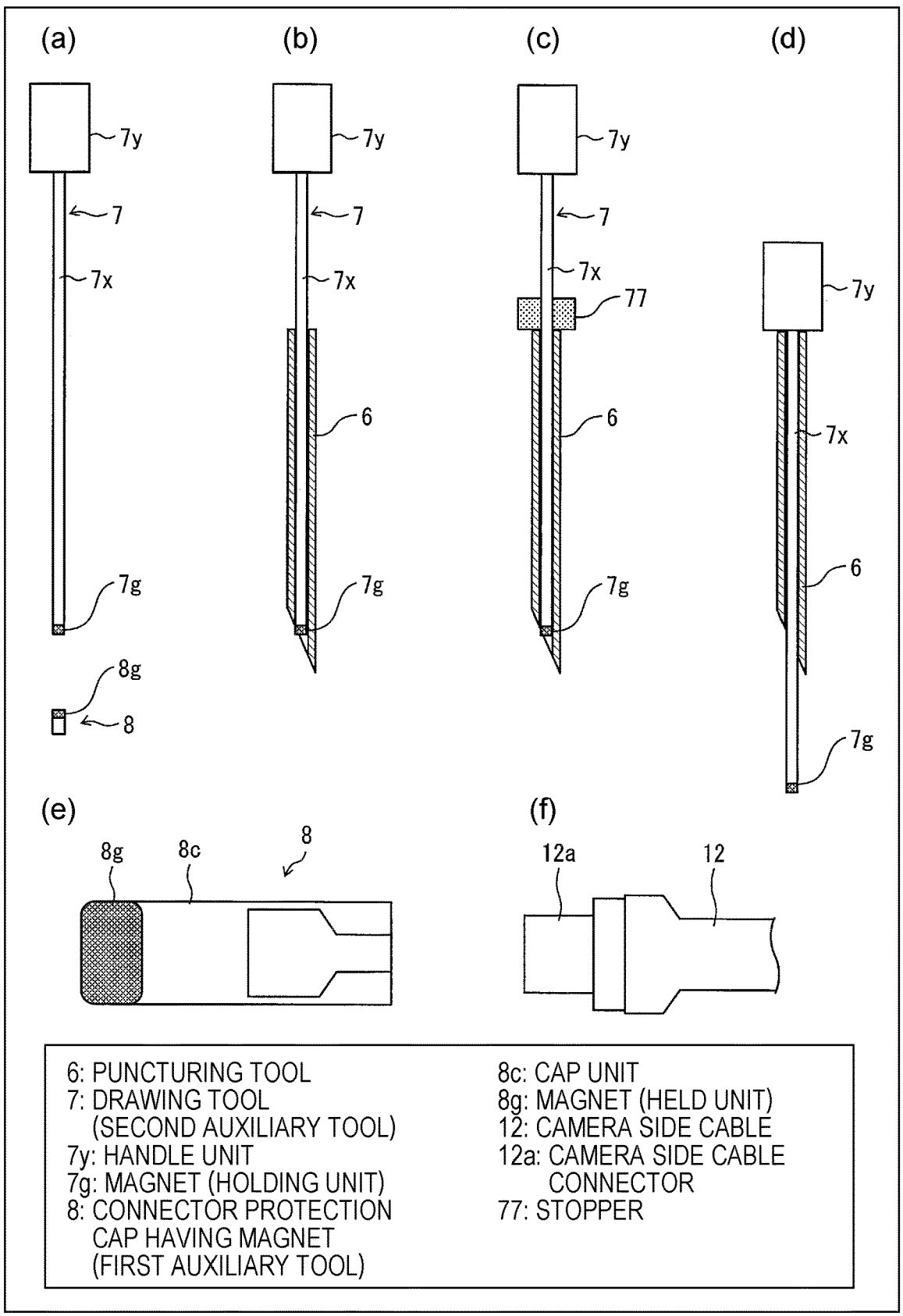
FIG. 4 is a view illustrating an example of an auxiliary tool set according to Embodiment 1.
Figure 5:
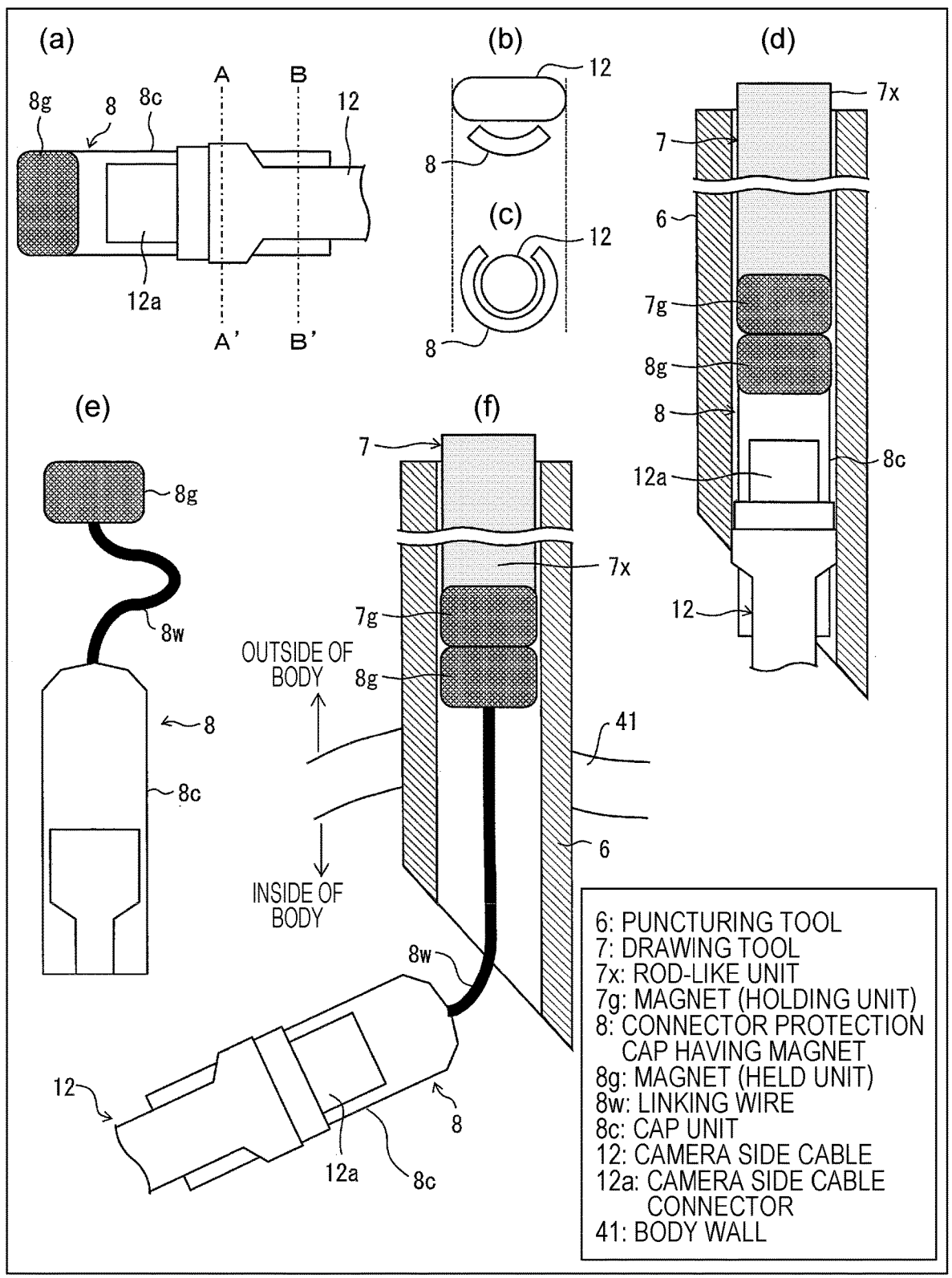
FIG. 5 is a view illustrating an example of the auxiliary tool set according to Embodiment 1.
Figure 6:
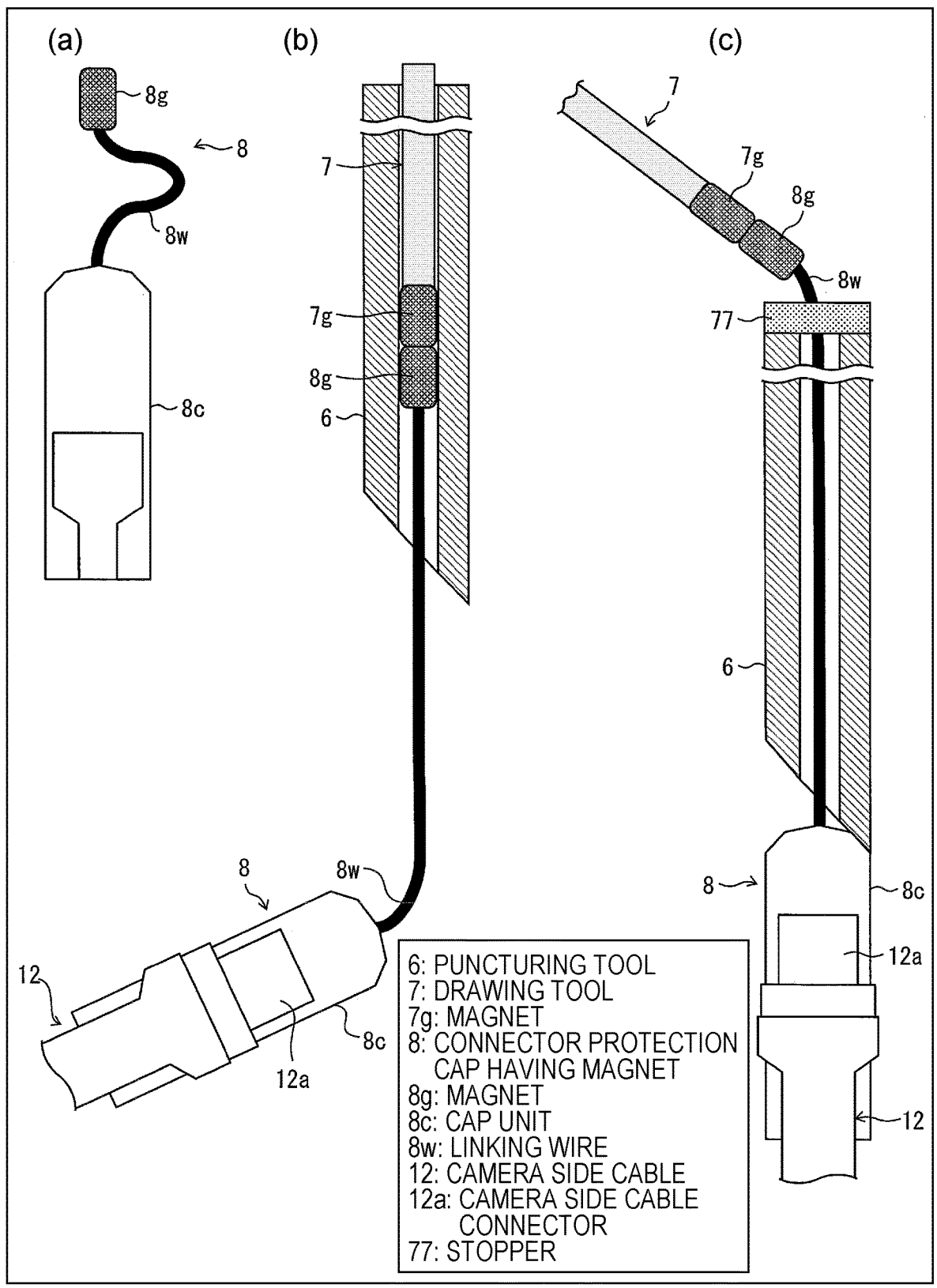
FIG. 6 is a view illustrating an example of the auxiliary tool set according to Embodiment 1.

FIG. 4(a) is a sectional view illustrating a schematic configuration of the drawing tool which is used in the embodiment, FIG. 4(b) is a sectional view in which the drawing tool is inserted into the puncturing device, FIG. 4(c) is a view illustrating a state where the stopper which fixes the drawing tool is added to FIG. 4(b), and FIG. 4(d) is a view illustrating a state where the drawing tool is pushed into the puncturing device. In addition, FIG. 4(e) is a view illustrating an example of the connector protection cap having a magnet, and FIG. 4(f) is a view illustrating a connector unit of a camera cable. FIG. 5(a) is a view in which the connector protection cap having a magnet is mounted on a camera cable connector unit, and FIGS. 5(b) and 5(c) are views respectively illustrating a section taken along line A-A' and a section taken along line B-B' of FIG. 5(a). In addition, FIG. 5(d) is a view illustrating a state where the drawing tool and the connector protection cap having a magnet are mounted and inserted into the puncturing device. FIG. 5(e) is a view illustrating another example of the connector protection cap having a magnet, and FIG. 5(f) is a view illustrating a state where the drawing tool and the connector protection cap having a magnet of FIG. 5(e) are mounted and inserted into the puncturing device. FIG. 6(a) is a view illustrating still another example of the connector protection cap having a magnet, FIG. 6(b) is a view illustrating a state where the drawing tool and the magnet connected to the connector protection cap having a magnet of FIG. 5(e) are adhered and inserted into the puncturing device, and FIG. 6(c) is a view illustrating a state where the magnet connected to the connector protection cap having a magnet is drawn out toward the outside of the body through the puncturing device.

As illustrated in FIG. 4(a), the drawing tool 7 used in the embodiment is configured of the magnet 7g (holding unit) which is provided at one end and adheres the connector protection cap having a magnet, the rod-like unit 7x, and a handle unit 7y provided at the other end. In addition, as illustrated in FIG. 4(b), the drawing tool 7 is a rod-like device in which the outer diameters of the magnet 7g and the rod-like unit 7x are smaller than the inner diameter of the needle-like puncturing device 6. In addition, the handle unit 7y has a dimension which is sufficiently greater than the inner diameter of the puncturing device 6.

FIG. 4(e) is a view illustrating an example of the connector protection cap having a magnet 8. The connector protection cap having a magnet 8 functions as a waterproof cap of the camera side cable connector 12a illustrated in FIG. 4(f), and is provided with a cap unit 8c and the magnet 8g (held unit) provided at the tip end thereof. As illustrated in FIG. 5(a), the connector protection cap having a magnet 8 has a recessed shape which corresponds to the shape of the camera side cable connector 12a, and mounts the camera side cable connector 12a to be fitted to the recessed unit. FIG. 5(b) is a section taken along line A-A' of FIG. 5(a), and FIG. 5(c) is a section taken along line B-B', and illustrates a structure which is hooked and fastened by using a neck of the camera side cable connector 12a therebetween, and which does not fall out even when being pulled. In order to make the inner diameter of the puncturing device 6 as small as possible, the width of the connector protection cap having a magnet 8 illustrated in FIGS. 5(a) to 5(c) becomes equal to or smaller than the width of a part (a thick part on the camera side cable connector 12a side) of the camera side cable connector 12a and the camera side cable 12.

In addition, the shape of the connector protection cap having a magnet 8 is not limited to the example, and can have an arbitrary shape corresponding to the shape of the camera side cable connector 12a.

For example, in a case where it is not possible to devise the cap unit 8c to be smaller than the outer diameter of the connector, due to the restriction caused by the shape of the camera side cable connector 12a without a neck, the outer diameter of the cap unit 8c may be slightly greater than the outer diameter of the camera side cable connector 12a.

In addition, for example, when the end part of the camera side cable connector 12a is formed to be slightly narrow, and the connector protection cap having a magnet 8 is fitted into the narrowed part, it is desirable that the outer circumference of the end surface of the connector protection cap having a magnet 8 matches the outer circumference of the part (thick part positioned further on a joint side than the end part) which is not the end part of the camera side cable connector 12a, and a step cannot be generated between the side surface of the connector protection cap having a magnet 8 and the side surface of the camera side cable connector 12a. In this manner, when pulling the camera side cable 12, it is possible to reduce a problem in which a boundary part between the camera side cable connector 12a and the connector protection cap having a magnet 8 is hooked to the inner wall of the tube-like device, such as the puncturing device 6, or the trocar or cannula, which is used in the other embodiment which will be described later, and the camera side cable 12 is dropped on the inside of the body.

In addition, regarding the connection (fitting) strength of the camera side cable connector 12a and the connector protection cap having a magnet 8, it is necessary not to make the camera side cable connector 12a and the connector protection cap having a magnet 8 come off when pulling up the camera side cable 12, and in a case where the magnet is used in the auxiliary tool set, a force which is equal to or greater than the magnetic force, for example, 2 N (newton) is desirable. In addition, when connecting the equipment side cable connector 16a or the first intermediate cable connector 15a, it is necessary to take out the connector protection cap having a magnet 8, and the connection strength by which a human being easily performs attachment and detachment is desirable. Therefore, it is desirable that the most appropriate range is set to be a range of 4 N to 10 N.

In addition, in general, the puncturing is performed by using the obturator 36, but instead of the obturator 36, the drawing tool 7 can be used. As illustrated in FIG. 4(c), a structure in which liquid is prevented from entering the inside of the tube of the puncturing device 6 in a case where the puncturing device 6 is inserted into a body wall 41 in a state where the drawing tool 7 is guided toward the inside of the puncturing device 6, and is fixed by the stopper 77, is achieved. In addition, as illustrated in FIG. 4(d), after performing the puncturing, when the stopper 77 comes off and is pushed into the inside of a body hole as it is, it is possible to immediately start pulling work of the next camera side cable 12.

Accordingly, when the needle-like puncturing device enters the inside of the body, there is not a case where the tube is clogged by the liquid, and the end part of the drawing tool 7 which has entered the needle-like puncturing device can pass through the body wall 41, and can be guided toward the inside of the body. In addition, since the obturator 36 is not used, it is possible to further simplify the puncturing work.

In addition, it is preferable that the diameter of the puncturing device 6 is small in order to realize the minimal invasiveness. Specifically, it is preferable that the diameter is equal to or less than 3 mm.

Another example of the connector protection cap having a magnet 8 is illustrated in FIGS. 5(e) and 5(f). The connector protection cap having a magnet 8 illustrated in FIG. 5(e) is configured to connect the cap unit 8c and the magnet 8g (held unit) by a linking wire 8w. In this case, since it is possible to reduce the size and the weight of a part of the magnet 8g, absorption is likely to occur in the drawing tool 7, and a range in which the absorption is possible can be widened. Therefore, since the absorption is possible even when the position is slightly deviated, a simple operation is possible during a short period of time.

Regarding the magnetic force of the magnet which is used in the connector protection cap having a magnet 8 of the examples, the adhering strength which is sufficiently large for drawing out the camera unit 11 and the camera side cable 12 is necessary. In the above-described example, the puncturing device 6 through which the camera unit 11 and the camera side cable 12 pass the inside thereof when drawing out the camera unit 11 and the camera side cable 12, does not have a valve structure. Therefore, since a large load is not applied when passing through the inside of the puncturing device 6, for example, a load which is equal to or greater than 0.5 N only for sufficiently supporting the weight combined by the camera unit 11 and the camera side cable 12, may be applied. In addition, when the removing is performed after the drawing-out, the adhering strength by which a human being can easily perform the removing by hand is desirable, and since it is necessary that the connection (fitting) strength of the connector protection cap having a magnet 8 and the camera side cable connector 12a is further reduced so that the connector protection cap having a magnet 8 does not come off during the drawing-out, it is desirable that the most appropriate range is set to be a range of 0.5 N to 4 N.

In addition, as illustrated in FIGS. 32(a) to 32(e), in a state where a holding unit 7h of the drawing tool 7 holds a held unit 8h of the connector protection cap having a magnet 8, it is desirable that the end surface (adhering surface) of the holding unit 7h and the end surface (adhering surface) of the held unit 8h overlap each other without being protruded, and each of the end surfaces is not exposed. For this, for example, the outer diameters of each of the holding unit 7h and the held unit 8h are the same, and the outer circumference of the end surface of the holding unit 7h and the outer circumference of the end surface of the held unit 8h are adhered to overlap each other. In addition, it is desirable that each of the end surfaces is circular so that end surfaces necessarily match each other even when the end surfaces are adhered in any orientation. In this manner, since a step is not generated between the side surface of the holding unit 7h and the side surface of the held unit 8h, it is possible to reduce a defect that the end surfaces of the holding unit 7h or the held unit 8h are hooked to the uneven part on the inside of the tube-like member and the held unit 8h comes off of the holding unit 7h when the held unit 8h is lifted.

In addition, since the absorbed part is touched by a living body, a medical material (biocompatible material) having biocompatibility is desirable, and it is desirable to cover the surface by a resin or SUS. In a case where the resin coating or an SUS (stainless steel) cover is used, in order to prevent deterioration of the absorption force, it is desirable that the thickness is equal to or less than 1 mm, and is preferably 0.15 mm (will be described later in detail). In addition, in a case of the magnetic body, if the thickness of the resin of the adhering surface (absorbed unit) is thinner than that of other parts, it is possible to prevent absorption at a location other than the adhering surface, and stable adhering is possible without deviating the position of the adhering surface. Accordingly, the hooking and the removing are not performed at an opening unit end of the puncturing device, and smooth passage is possible. Accordingly, reduction of the installation time is achieved.

Figure 32:
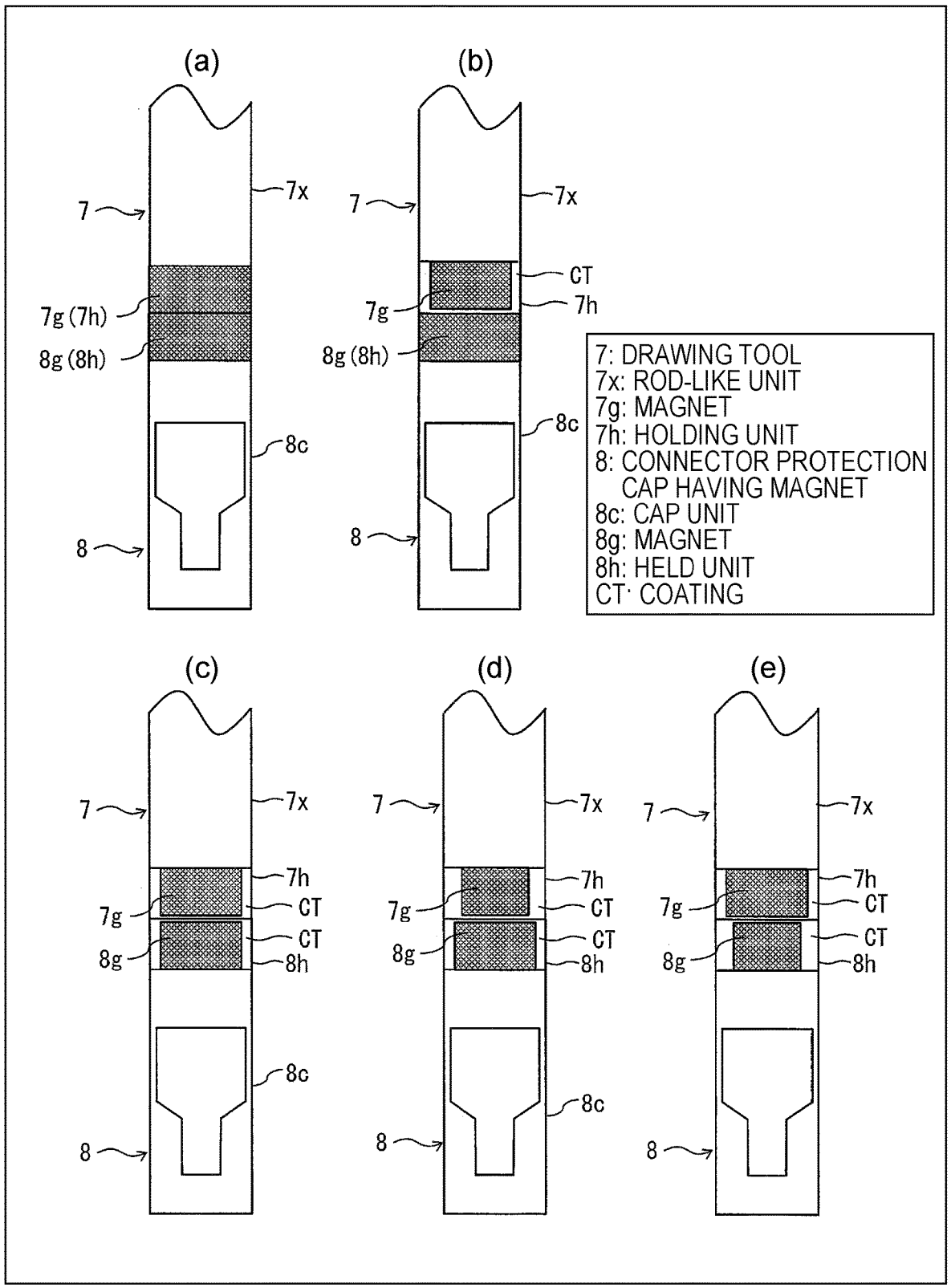
FIGS. 32(a) to 32(e) are schematic views illustrating a schematic example of a holding unit and a held unit.

FIG. 32(a) illustrates a case where the surfaces of the holding unit 7h and the held unit 8h are not coated with a biocompatible material (for example, biocompatible resin), FIG. 32(b) illustrates a case where the surface of the holding unit 7h is coated with the biocompatible material, and the surface of the held unit 8h is not coated with the biocompatible material, and FIGS. 32(c) to 32(e) illustrate a case where surfaces of the holding unit 7h and the held unit 8h are coated with the biocompatible material, and both the holding unit 7h and the held unit 8h have a cylindrical shape.

In FIGS. 32(a) to 32(e), the outer diameters of the end surfaces of the holding unit 7h and the held unit 8h are the same as each other, the gravity center of the end surface of the magnet 7g is disposed on the axis of the holding unit 7h, and the gravity center of the end surface of the magnet 8g is disposed on the axis of the held unit 8h. Accordingly, in a state where the held unit 8h is adhered to the holding unit 7h, the outer circumference of the end surface of the holding unit 7h and the outer circumference of the end surface of the held unit 8h overlap each other, and a step is not generated between the side surface of the holding unit 7h and the side surface of the held unit 8h.

Regarding the magnet 7g of the drawing tool 7 and the magnet 8g of the connector protection cap having a magnet 8, it is desirable that the outer diameter of the end surface of the magnet 7g and the outer diameter of the end surface of the magnet 8g are the same as illustrated in FIGS. 32(a) and 32(c), but even when the outer diameter of the end surface of the magnet 7g is smaller than the outer diameter of the end surface of the magnet 8g as illustrated in FIGS. 32(b) and 32(d), the outer diameter of the end surface of the magnet 7g may be greater than the outer diameter of the end surface of the magnet 8g as illustrated in FIG. 32(e). However, as will be described later, it is desirable that the outer diameter of the end surface of a smaller magnet is equal to or greater than 70% of the outer diameter of the end surface of a larger magnet.

As illustrated in FIGS. 32(b) to 32(e), regarding the thickness of a coating CT (biocompatible material) of the holding unit 7h or the held unit 8h, in order to maintain the magnetic force which becomes a holding force, the end surface (adhering surface) is smaller than the side surface. It is desirable that the coating CT of the end surface (adhering surface) is as thin as possible, but the thickness only for preventing the coating CT from being peeled in the use period is necessary.

In the above-described example, the absorption by the magnetic force is used in holding the connector protection cap having a magnet 8 by the drawing tool 7, but the invention is not limited thereto. For example, similar to a surface fastener, it is also possible to use a physical adhesion between fibers having different shapes.

In addition, a magnet is used in both the held unit of the first auxiliary tool and the holding unit of the second auxiliary tool, but the invention is not limited thereto. A magnet may be used in one of the held unit of the first auxiliary tool and the holding unit of the second auxiliary tool, and a magnetic body of a non-magnet absorbed in the magnet may be used in the other one of the held unit of the first auxiliary tool and the holding unit of the second auxiliary tool. In particular, in order to prevent the absorption to surgical instrument, such as the forceps, it is desirable that the held unit provided in the first auxiliary tool is a magnetic body of the non-magnet. In addition, it is desirable to use the non-magnetic body as the puncturing device 6 through which the magnet passes, and for example, a hard resin can be used.

Figure 33:
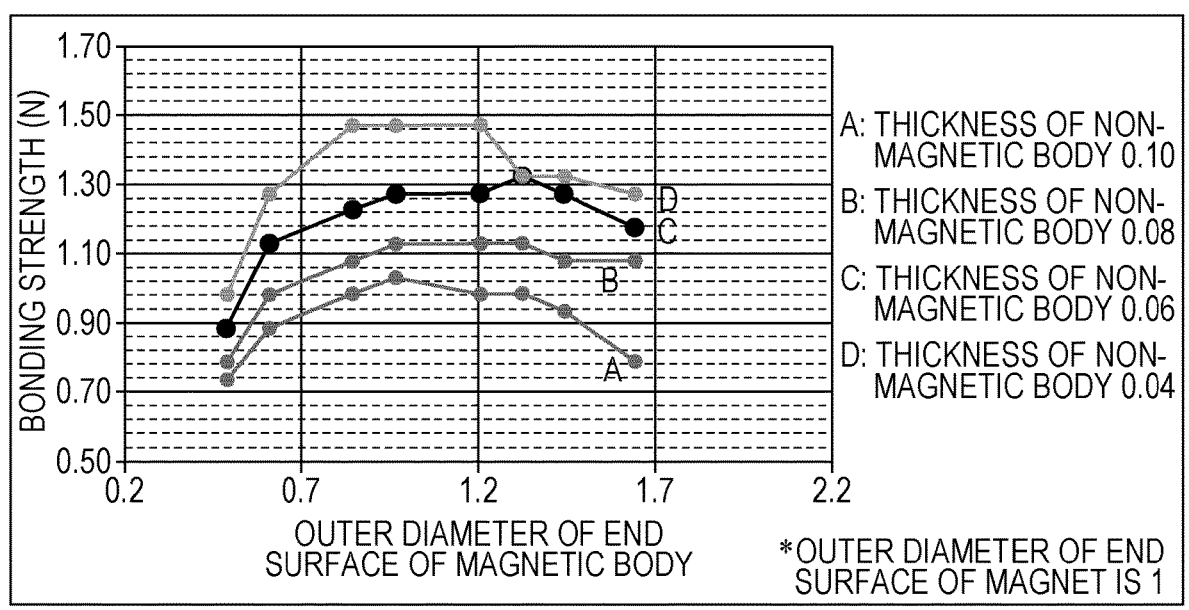
FIG. 33 is a view illustrating a relationship between the outer diameter and the adhering strength of each of the magnet and the magnetic body, which are provided in the auxiliary tool set, by using the thickness of a non-magnetic body, which is the thickness of coating, as a parameter.

FIG. 33 illustrates a relationship between the outer diameter and the adhering strength of the end surfaces of the magnet and the magnetic body in a case where the magnet is used in one of the held unit of the first auxiliary tool and the holding unit of the second holding tool, and the magnetic body (including the magnet) is used in the other one of the held unit of the first auxiliary tool and the holding unit of the second holding tool. In addition, the outer diameter of the end surface of the magnet is set to be 1, and the thicknesses of the non-magnetic body (biocompatible coating) which covers the surface of the magnetic body are set to be parameters (0.04, 0.06, 0.08, 0.10). For example, when the outer diameter of the end surface of the magnet is 2 mm, the thicknesses of the non-magnetic body are respectively 0.08 mm, 0.12 mm, 0.16 mm, and 0.20 mm.

As illustrated in FIG. 33, it is desirable that the outer diameter of the end surface of the magnetic body is substantially the same as the outer diameter of the end surface of the magnet. In addition, it is ascertained that it is desirable that the thickness of the non-magnetic body (biocompatible coating) is thin. For example, when the thickness of the non-magnetic body is set to be a half, the adhering strength is improved by approximately 30%. As will be described later, since the adhering strength which is equal to or greater than 1 N is necessary in order to pass through the valve structure, such as the trocar, in order to ensure stable strength which is equal to or greater than 1 N, it is desirable that the thickness of the non-magnetic body (coating of the magnetic body) is less than 8% (for example, 0.16 mm when the outer diameter of the magnet is 2 mm) of the outer diameter of the end surface of the magnet, or the outer diameter of the end surface of the magnetic body is 70% to 130% of the outer diameter of the end surface of the magnet.

In addition, as the magnet, not a permanent magnet, but an electromagnet can be used. In this case, except the time when the absorption is performed, it is desirable that the conduction is off, since it is possible to prevent the problem of the absorption to the other devices, and the material of other devices is not limited.

In addition, it is desirable that the tip end (in particular, a magnet which is a holding unit) of the drawing tool 7, the connector protection cap having a magnet 8, and a member inserted into the body, such as the linking wire 8w, are configured of a material having a blue color, a blue-green color, and a green color of the cold color system, which is easily noticed on the inside of the body, similar to the above-described camera housing 21 or the camera side cable 12. According to this, visual recognition can be easily performed when the installation work or the collection work is performed on the inside of the body, and the work time can be reduced. In this manner, in coloring the tip end of the drawing tool 7, the connector protection cap having a magnet 8, and a member inserted into the body, such as the linking wire 8w, it is possible to use a color (a color which is easily noticed on the inside of the body) which corresponds to the visible light having a wavelength of 420 nm to 570 nm (in particular, preferably 450 nm to 530 nm).

In addition, as described above, other than performing the coloring using a blue material or a green material, the light-storing material or the reflective material which is likely to be visually recognized may also be used. According to this, when an object is in a shadow of an organ which is unlikely to be visually recognized, or at an end of a visual field to which illumination light is unlikely to reach, it is possible to directly find the object, and thus, a special effect that the light-storing material or the reflective material is particularly effective, and stability is improved, is obtained.

<Method for Installing Camera System for Monitoring Inside of Body>

Next, both a method for installing the camera system for monitoring the inside of a body according to the embodiment, and a method of use thereof, will be described.

FIGS. 7(a) to 7(d) and FIGS. 8(a) to 8(c) are schematic views illustrating the method for installing the camera system for monitoring the inside of a body according to the embodiment, in a process order. In addition, FIGS. 9(a) and 9(b) are modification examples with respect to the process of each of FIG. 7(d) and FIG. 8(a).

As illustrated in FIG. 7(a), first, the practitioner opens ports 41a to 41c (holes) for inserting the forceps or the endoscope into the body cavity on the body wall 41, and inserts each of the plural trocars 32 (hereinafter, referred to as trocars 32a to 32c) into the ports 41a to 41c.

After inserting at least one trocar among the trocars 32a to 32c into the body wall 41, the practitioner sends gas into the body through at least one trocar among the trocars 32a to 32c, and expands the inside of the body cavity.

Furthermore, in order to install the camera unit 11 on the inside of the body cavity, a port 41d is opened at a position where the entire organ including an affected part can be seen on the body wall 41 by using the puncturing device 6.

Specifically, by puncturing the obturator into the port in a state where the needle-like obturator (not illustrated) has passed through the inside of the puncturing device 6, the puncturing device 6 is inserted into the body wall 41.

Instead of the obturator, the drawing tool 7 may be inserted again.

Next, as illustrated in FIG. 7(b), by gripping the support unit 22 of the camera unit 11 using the forceps 33a, the camera side cable 12 and the camera unit 11 in which the connector protection cap having a magnet 8 is mounted on the camera side cable connector (not illustrated) are inserted into the body cavity again.

Next, as illustrated in FIG. 7(c), the practitioner inserts the endoscope 34 into the body cavity through the trocar 32c, grips the support unit 22 of the camera unit 11 by the forceps 33a while observing the inside of the body using the endoscope 34, moves the camera side cable 12 and the camera unit 11 to the lower part of the port 41d, and further, inserts the drawing tool 7 into the puncturing device 6, and the end part of the camera side cable 12 is absorbed to the connector protection cap having a magnet 8. In the embodiment, since the magnets (7g, 8g) are used in adhering the drawing tool 7 and the connector protection cap having a magnet 8, the absorption is performed by the magnetic force even when the position is slightly deviated, and the operation can be simply performed during a short period of time.

Next, as illustrated in FIG. 7(d), the drawing tool 7 is drawn out of the puncturing device 6, and the connector protection cap having a magnet 8 to which the camera side cable 12 is connected is drawn out toward the outside of the body. Since the handle unit 7y is present at one more end part of the drawing tool 7, the drawing tool 7 is not mistakenly dropped on the inside of the body, and the operation can be completely performed.

Figure 8:
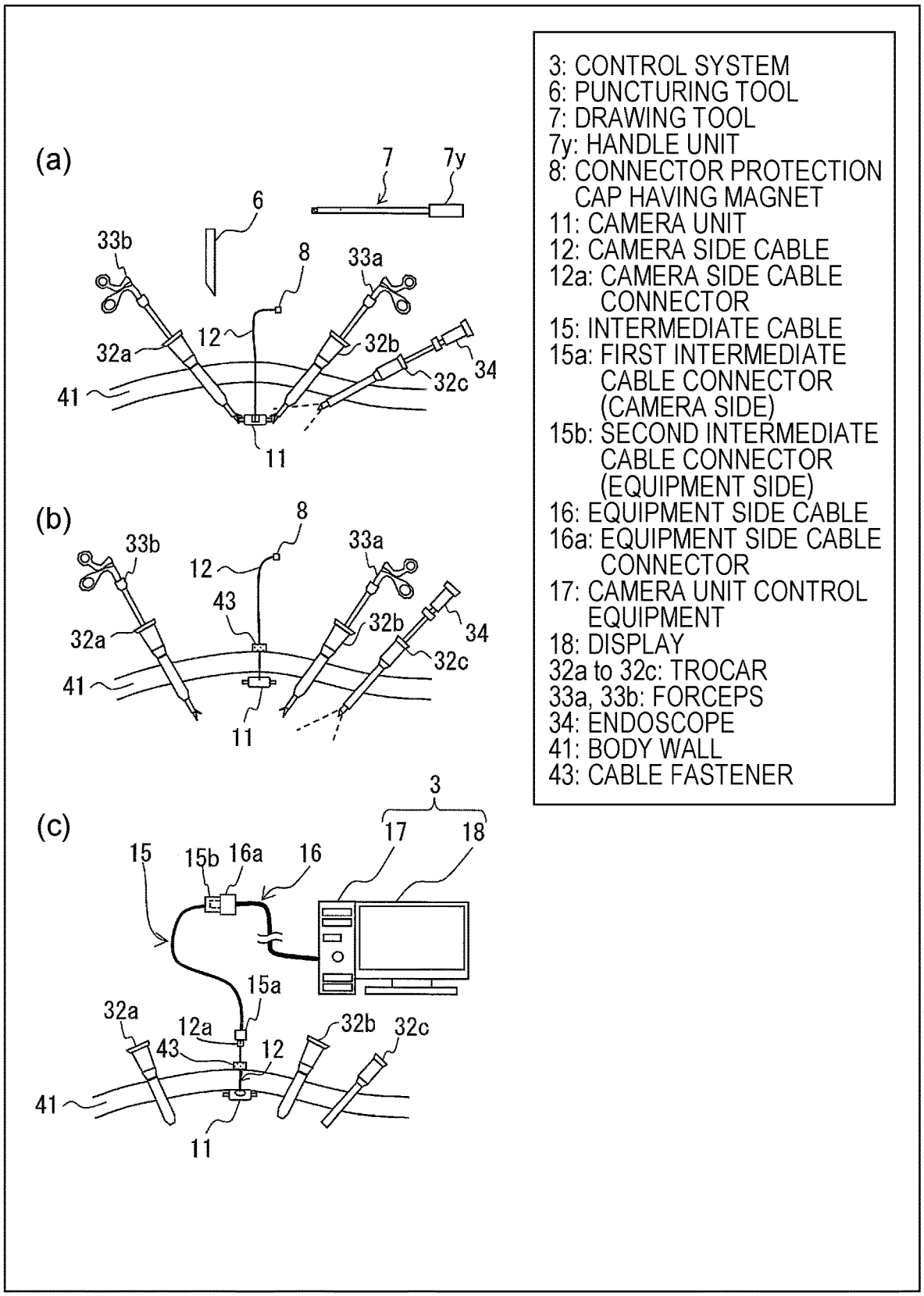
FIGS. 8(a) to 8(c) are schematic views illustrating the method for installing the imaging apparatus in the camera system for monitoring the inside of a body according to Embodiment 1, in a process order following FIGS. 7(a) to 7(d).

Next, as illustrated in FIG. 8(a), the connector protection cap having a magnet 8 is removed from the drawing tool 7, and the puncturing device 6 is extracted from the body wall 41, and as illustrated in FIG. 8(b), the camera unit 11 is pulled up to the installation position of the body wall, and is fixed by using a cable fastener 43.

Since the puncturing device 6 is extracted and only the camera side cable 12 remains, the hole diameter of the port 41d can be equivalent to the outer diameter of the camera side cable connector 12a, and for example, can be 3 mm.

In a medical apparatus of PTL 2, in order to draw out the communication cable toward the inside of the body, it is necessary to perform a difficult operation, such as hooking the wire to a hook unit on the inside of the body.

Meanwhile, in the camera system for monitoring the inside of a body of the embodiment, by a simple operation of making the magnet 7g provided at the tip end of the drawing tool 7 and the connector protection cap having a magnet 8 close to each other, it is possible to hold the connector protection cap having a magnet 8 at the tip end of the drawing tool 7. Accordingly, it is possible to easily draw out the camera side cable connector toward the outside of the body.

Here, the modification example with respect to the process of FIGS. 7(d) and 8(a) of the embodiment will be described by using FIGS. 9(a) and 9(b) and FIGS. 6(a) to 6(c).

In the modification example, the connector protection cap having a magnet 8 illustrated in FIG. 6(a) is used. The connector protection cap having a magnet 8 is configured so that the magnet 8g and the cap unit 8c are connected by the linking wire 8w, the diameter of the magnet 8g and the linking wire 8w is smaller than that of the cap unit 8c, and the length of the linking wire 8w is longer than that of the puncturing device 6.

As illustrated in FIG. 9(a), by the order described in FIG. 7(d), the magnet 8g is drawn out of the puncturing device 6. As illustrated in FIG. 6(c), since the inner diameter of the puncturing device 6 is greater than the outer diameter of the cap unit 8c, the pulling-up is stopped at this position, but fixing is performed by the stopper 77. Next, the camera side cable connector 12a part of the end part of the camera side cable 12 is drawn out toward the outside of the body for each puncturing device 6. Since the camera side cable 12 is fixed by the stopper 77, it is possible to prevent the camera side cable 12 from being mistakenly dropped on the inside of the body when drawing out the puncturing device 6.

The diameter of the camera side cable connector 12a unit slightly increases to be approximately 3 mm, but since the area is small, the camera side cable connector 12a can pass through the body wall 41 while temporarily expanding the hole of the body wall. Accordingly, the diameter of the puncturing device 6 and the camera side cable 12 can be the diameter which is approximately 2 mm. Therefore, the wound of an installation unit of the camera unit 11 can be the minimum, and more minimal invasiveness can be achieved.

Next, as illustrated in FIG. 9(b), after the temporary stopping by the cable fastener 43, the stopper 77 is removed, and the puncturing device 6 is extracted from the linking wire 8w.

Hereinafter, similarly, as illustrated in FIG. 8(b), the camera unit 11 is pulled up to the installation position of the body wall, and is fixed by using the cable fastener 43, and the drawing tool 7 is removed.

Next, as illustrated in FIG. 8(c), the connector protection cap having a magnet 8 is removed from the camera side cable connector 12a, the camera side cable 12 and the intermediate cable 15 are connected by the camera side cable connector 12a and the first intermediate cable connector 15a, and the intermediate cable 15 and the equipment side cable 16 are connected by the second intermediate cable connector 15b and the equipment side cable connector 16a. In addition, since the intermediate cable 15 or the equipment side cable 16 do not pass through the inside of the body, the cable having a large diameter can be used.

Accordingly, the entire image of the inside of the body captured by the camera unit 11 is displayed on the display 18 by the camera unit control equipment 17.

Next, while seeing the image of the display 18 and the image of the camera unit 11 reflected by the endoscope 34, the support unit 22 is gripped by the forceps 33, the camera unit 11 is moved, and the orientation inside the body cavity is adjusted.

In a case where the camera image is seen not from immediately above but diagonally at a certain angle, a camera unit of a type in which a part at which the camera side cable 12 is drawn out of the camera unit 11 is deviated in the diagonal direction from an optical axis of the camera, may be prepared in advance.

After the positioning of the camera unit is completed, by using the cable fastener 43, the camera unit is then fixed to the body wall, and is started to be used.

Accordingly, the practitioner can perform treatment using the forceps while enlarging and observing the work region (local region) on the display of the endoscope, and can also grasp the state (movement of the forceps or the like, a bleeding site, and a residual, such as gauze, outside the work region) outside the work region on the display 18.

<Method for Collecting Camera Unit>

An order of collecting the camera unit 11 after the surgery is finished, will be described.

First, the camera side cable connector 12a and the cable fastener 43 are removed, and the practitioner grips the support unit 22 of the camera unit 11 on the inside of the body using the forceps 33, draws in the pulled camera side cable 12 toward the inside of the body, and then, draws out the camera side cable 12 toward the outside of the body from the trocar 32. Otherwise, the camera side cable 12 may be drawn out of the hole opened for drawing out a cut organ.

<Effect>

As described above, according to the embodiment, during the endoscopic surgery, it is possible to install an apparatus which can grasp a situation on the inside of the body in a wide viewing field and can substantially enhance safety, during a short period of time without stressing out a practitioner by a simple and safe method only by generating a minimal wound which is equivalent to the size of the outer diameter of the camera side cable 12.

Modification Example

A modification example of the magnet which is used in the drawing tool and the connector protection cap having a magnet, or the magnetic body, will be described in FIGS. 28 to 30.

Figure 28:
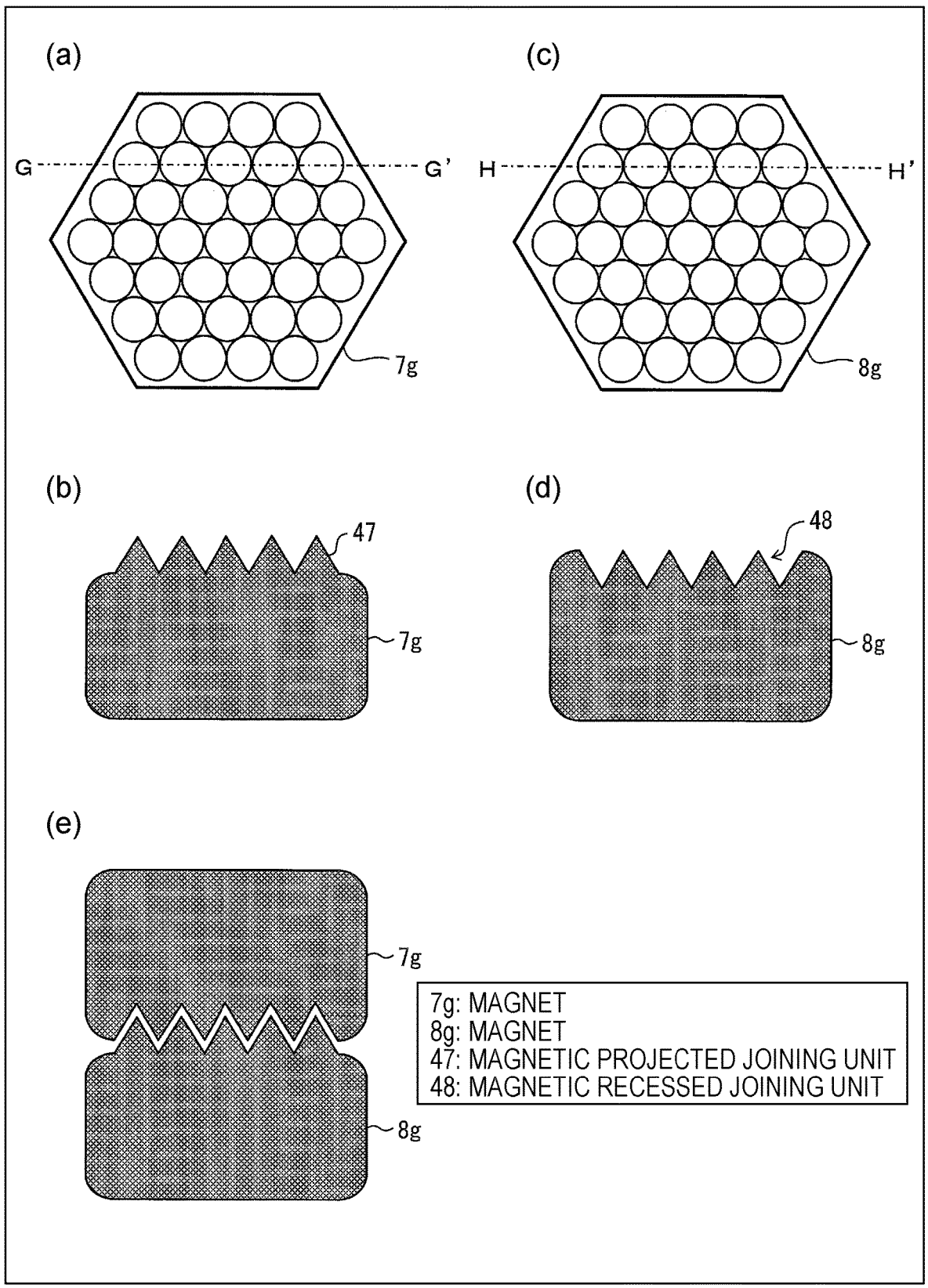
FIG. 28 is a view illustrating an example of a magnet which is used in a modification example of Embodiment 1.

FIG. 28 is a view illustrating an example of the magnet which is used in the modification example. FIG. 28(a) is a plan view of a joining surface of the magnet having a projected joining unit, FIG. 28(b) is a sectional view taken along line G-G' of FIG. 28(a), FIG. 28(c) is a plan view of a joining surface of the magnet having a recessed joining unit, FIG. 28(d) is a sectional view taken along line H-H' of FIG. 28(c).

As illustrated in FIG. 28(e), a structure in which the projected joining unit and the recessed joining unit are fitted to each other is employed, and here, a shape in which multiple conical projections or hollows are disposed in the shape of a honeycomb, is employed. Therefore, by performing rotation within 60 degrees at the time of the connection, it is possible to cause the projected joining unit and the recessed joining unit to be tightly adhered and fitted to each other. In addition, a fitting structure of the unevenness is not limited to the structure in which the conical projections are disposed in the shape of a honeycomb.

Figure 29:
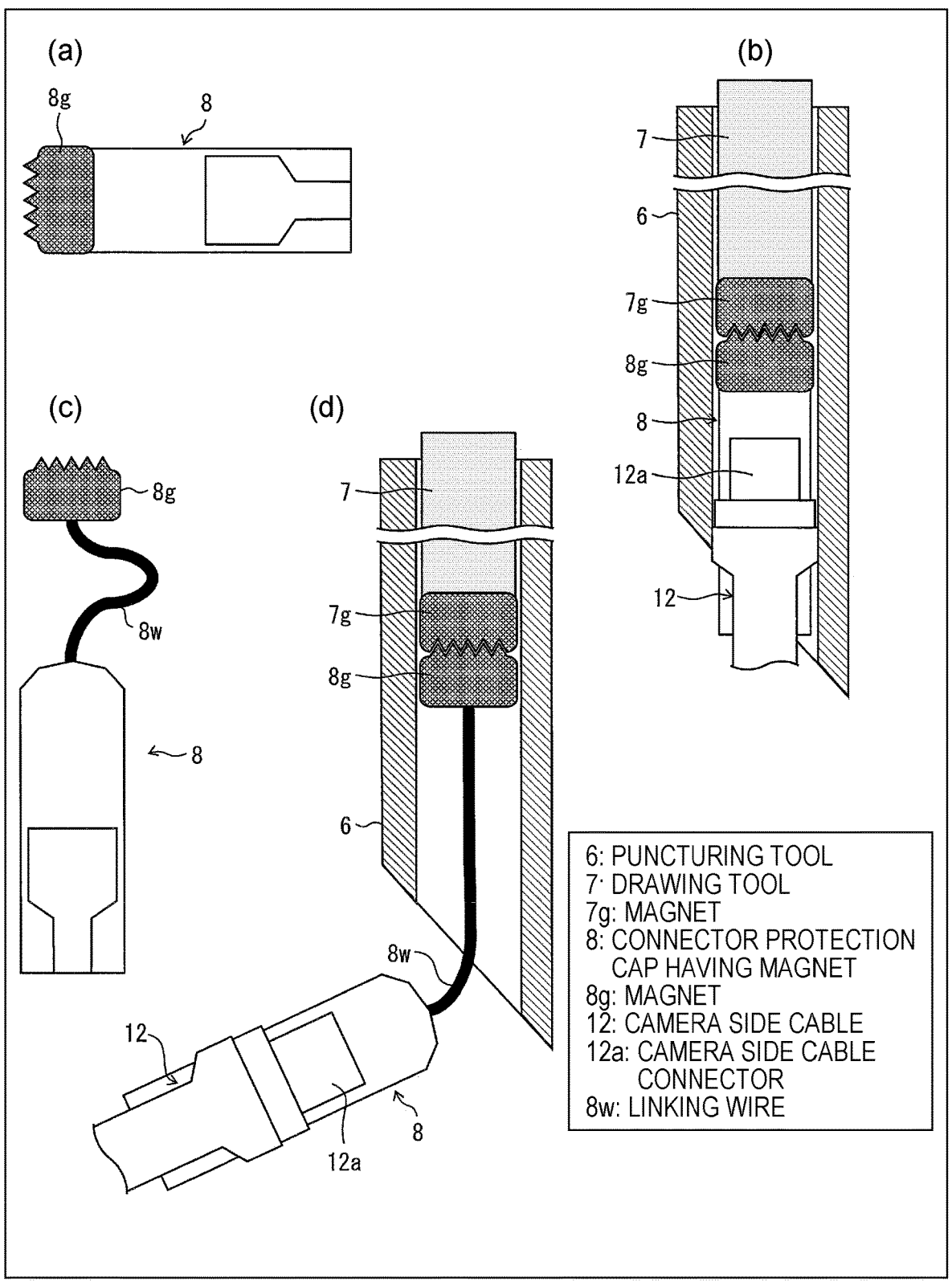
FIG. 29 is a view illustrating a drawing tool and a connector protection cap having a magnet which are configured by using a magnet of the modification example of Embodiment 1.

FIG. 29 is a view illustrating the drawing tool and the connector protection cap having a magnet which are configured by using the magnet, FIG. 29(a) is a view illustrating an example in which the magnet is directly attached to the connector protection cap having a magnet, and FIG. 29(b) is a view illustrating a state where the drawing tool and the connector protection cap having a magnet of FIG. 29(a) are adhered and inserted into the puncturing device. FIG. 29(c) is a view illustrating another example of the connector protection cap having a magnet to which the magnet is connected by the linking wire, and FIG. 29(d) is a view illustrating a state where the drawing tool and the connector protection cap having a magnet of FIG. 29(c) are adhered and inserted into the puncturing device.

As illustrated in FIGS. 29(b) and 29(d), when the magnets used in the modification example have uneven shapes fitted to each other, in order to completely tightly adhere the magnets, the absorption is strongly performed. However, in other devices of which the shapes do not match, a structure in which the absorption force is weakened in order to generate a space therebetween, is employed.

Figure 30:
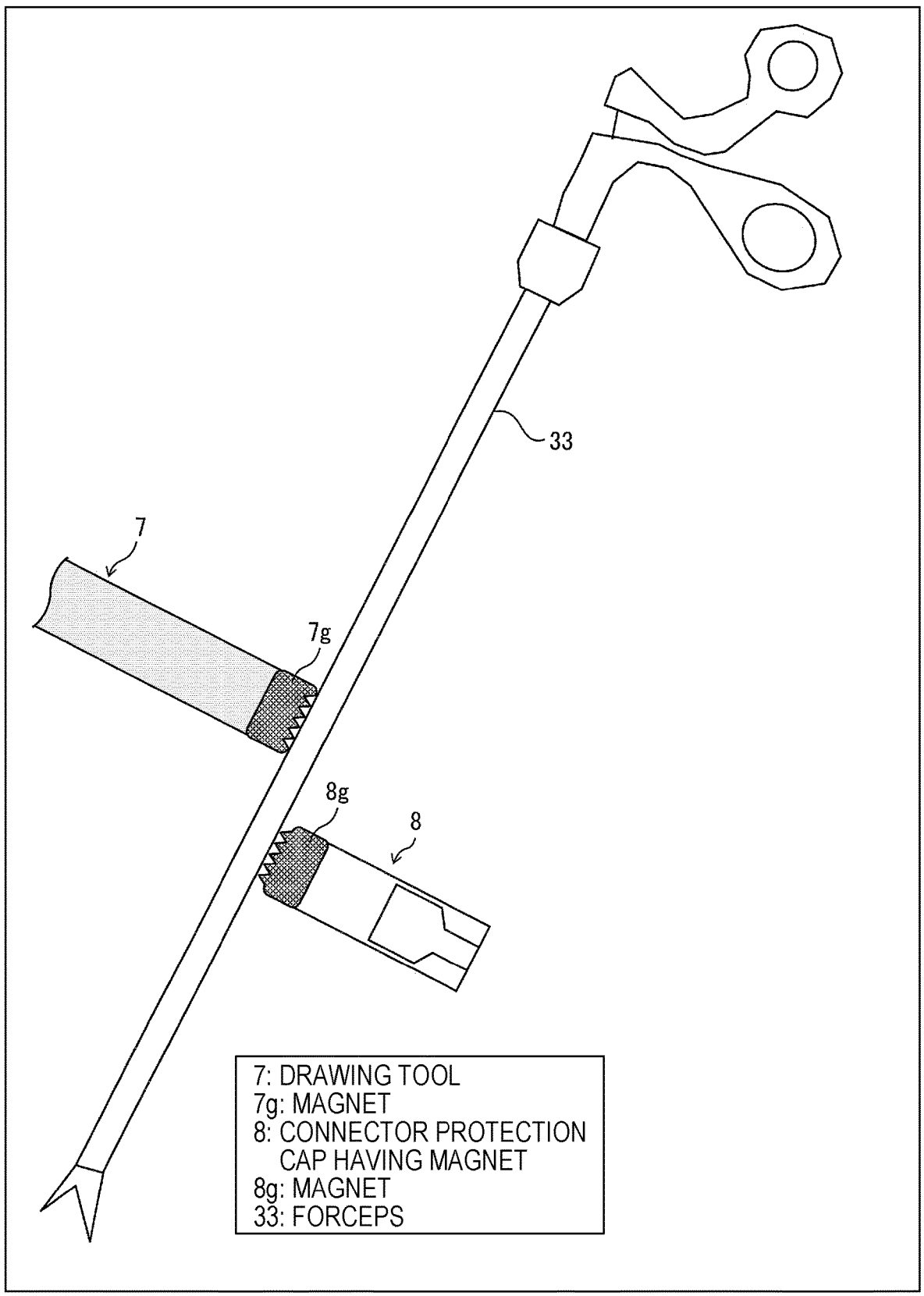
FIG. 30 is a view illustrating a state where forceps and the magnet are close to each other.

Accordingly, as illustrated in FIG. 30, even when the surgical instrument, such as the forceps, is absorbed to the magnet, since only small part of the area is in contact with the magnet, a defect that the absorption force is weak and the surgical instrument is absorbed and is not separated, is avoided.

Regarding the magnetic force of the magnet which is used in the connector protection cap having a magnet 8 of the examples, the adhering strength which is sufficiently large for drawing out the camera unit 11 and the camera side cable 12 is necessary. In the above-described example, the puncturing device 6 through which the camera unit 11 and the camera side cable 12 pass the inside thereof when drawing out the camera unit 11 and the camera side cable 12, does not have a valve structure. Therefore, since a large load is not applied when passing through the inside, for example, a load which is equal to or greater than 0.5 N only for sufficiently supporting the weight of the camera unit 11 and the camera side cable 12 combined, may be applied. Therefore, it is desirable that the adhering strength with other devices of which the shapes do not match each other is less than 0.5 N.

In addition, when the removing is performed after the drawing-out, the adhering strength by which a human being can easily perform the removing by hand is desirable, and since it is necessary that the fitting strength of the connector protection cap having a magnet 8 and the camera side cable connector 12a is further reduced so that the connector protection cap having a magnet 8 does not come off during the drawing-out, it is desirable that the most appropriate range is set to be a range of 0.5 N to 4 N.

In addition, the magnet is used in both the held unit of the first auxiliary tool and the holding unit of the second auxiliary tool, but the invention is not limited thereto. A magnet may be used in one of the held unit of the first auxiliary tool and the holding unit of the second auxiliary tool, and a magnetic body of a non-magnet absorbed in the magnet may be used in the other one of the held unit of the first auxiliary tool and the holding unit of the second auxiliary tool.

In addition, since the absorbed part is touched by a living body, a medical material having biocompatibility is desirable, and it is desirable to cover the surface by a resin or SUS. In a case where the resin coating or an SUS cover is used, in order to prevent deterioration of the absorption force, it is desirable that the thickness is equal to or less than 1 mm, and is preferably 0.15 mm. In addition, in a case of the magnetic body, if the thickness of the resin of the adhering surface is thinner than that of other parts, it is possible to prevent absorption at a location other than the adhering surface, and stable adhering is possible without deviating the position of the adhering surface. Accordingly, without hooking and removing at the opening unit end of the device, such as the puncturing device, the camera support tube, the cannula, or the trocar, which is used when drawing out the cable, smooth passage is possible. Accordingly, reduction of the installation time is achieved.

Embodiment 2

Another embodiment of the present invention will be described based on FIGS. 10 to 18 as follows. In addition, mainly, differences from Embodiment 1 will be described, configuration elements which have the same functions as those of the configuration elements used in Embodiment 1 will be given the same reference numerals, and the description thereof will be omitted. In addition, in the embodiment, it is also needless to say modifications similar to those of Embodiment 1 are possible.

<Schematic Configuration of Camera System for Monitoring Inside of Body>

Figure 10:
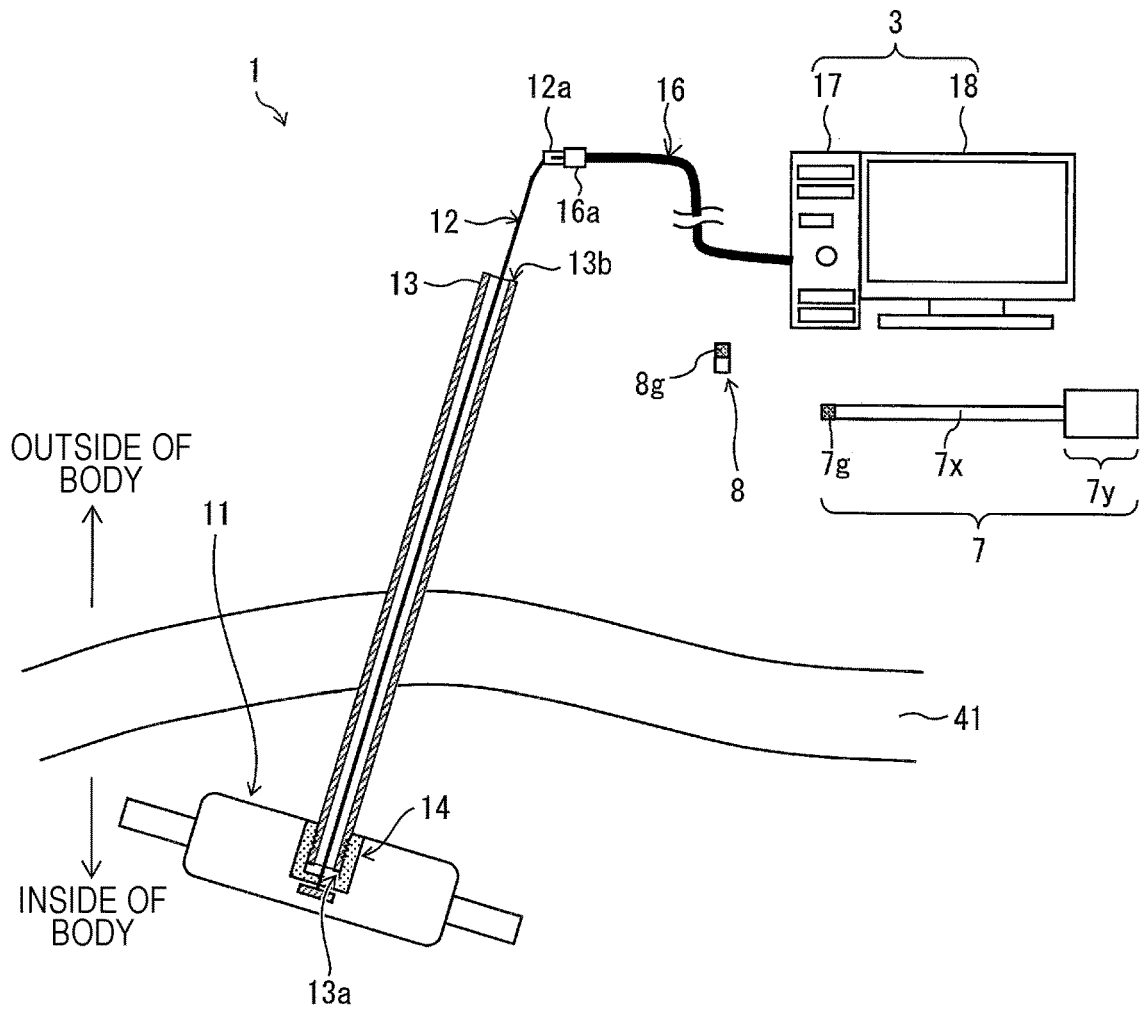
FIG. 10 is a schematic view illustrating a schematic configuration of a camera system for monitoring the inside of a body according to Embodiment 2.

FIG. 10 is a schematic view illustrating a schematic configuration of the camera system for monitoring the inside of a body 1 according to the embodiment.

As illustrated in FIG. 10, the camera system for monitoring the inside of a body 1 according to the embodiment is provided with the camera unit 11 (imaging part) which captures the inside of the body, the camera side cable 12 in which one end is connected to the camera unit 11, the control system 3 including the display 18 (display unit), the equipment side cable 16 in which one end is connected to the control system 3, the connector protection cap having a magnet 8 (first auxiliary tool) connected to the other end of the camera side cable 12, the drawing tool 7 (second auxiliary tool) which includes the rod-like unit 7x connected to the magnet 7g (holding unit) which holds the magnet 8g (held unit) provided in the connector protection cap having a magnet 8, and the magnet 7g, and which draws out the magnet 8g toward the outside of the body from the inside of the body through the inside of the tube-like device in a state of being held by the magnet 7g, and the camera support tube 13 (support tube). In addition, an equipment side cable connector 16a (projected shape) provided at the other end of the equipment side cable 16 is fitted to a camera side cable connector 12a (recessed shape) provided at the other end of the camera side cable 12, and the camera unit 11 and the control system 3 are electrically connected to each other. In addition, hereinafter, there is a case where the camera side cable connector 12a is briefly referred to as a connector 12a, and the equipment side cable connector 16a is briefly referred to as a connector 16a.

<Camera Unit>

As illustrated in FIGS. 11(a) and 11(b), the camera unit 11 is provided with the camera housing 21, the circuit board 19, the imaging unit 24, the control circuit 28, the illumination apparatus 27, and the support unit 22.

The circuit board 19, the imaging unit 24, the control circuit 28, and the illumination apparatus 27 are provided in the camera housing 21. Meanwhile, the support unit 22 is provided on the outer side of the camera housing 21.

Since configuration elements except a support tube joining unit 14 are the same as those of Embodiment 1, the description thereof will be omitted.

The camera housing 21 includes a recessed support tube joining unit 14 (joining unit) on an upper surface thereof. The support tube joining unit 14 has an annular opening shape (hole structure) when viewed from above as illustrated in FIG. 11(b), and has a configuration in which a locking female screw 23 is provided on an inner wall of the opening as illustrated in FIG. 11(a). The joining unit 14 may be configured to be fixed at a separate part having not a shape of a screw, but a shape only of being inserted. In addition, it is possible to use the needle-like puncturing device as it is as a support tube, and a recessed shape which corresponds to a shape of the puncturing device may be provided.

(Camera Side Cable)

The camera side cable 12 is a camera side communication cable. The camera side cable 12 sends the image captured by the camera unit 11 to the camera unit control equipment 17 via the connectors 12a and 16a as the image signal, or sends the control signal from the camera unit control equipment 17 to the camera unit 11.

The camera side cable 12 is connected to the circuit board 19, and is guided toward the outside of the camera unit 11 to pass through the inside of the support tube joining unit 14. In addition, the connection unit of the circuit board 19 and the camera side cable 12 is sealed by a resin or the like which is not illustrated. Furthermore, in the support tube joining unit 14, at a part (bottom part of the recessed support tube joining unit 14) at which the camera side cable 12 is drawn out, the camera side cable 12 is adhered and fixed to the inside of the support tube joining unit 14. An example of adhering and fixing includes sealing and fixing using an adhesive or an O-ring. Infiltration and incorporation of foreign substances into the camera unit 11 from the adhered and fixed part, are prevented.

In addition, the camera side cable 12 passes through the tube-like member, such as the trocar 32 (refer to FIG. 13) in a state of being connected to the camera unit 11 and is guided toward the inside of a body cavity, or passes through the camera support tube 13 (refer to FIGS. 10 and 12) which will be described later and is joined to the camera unit 11 via the support tube joining unit 14, or the puncturing device 6 (refer to FIG. 3), and is drawn out toward the outside of the body. Therefore, the camera side cable 12 is formed of a flexible material having ductility.

In addition, although will be described late in detail, when connecting the camera unit 11 and the camera support tube 13, the camera side cable connector 12a and the camera side cable 12 are drawn out toward the outside of the body from the inside of the body through the camera support tube 13. Therefore, the outer diameter of the camera side cable connector 12a becomes smaller than the outer diameter of the camera support tube 13. Therefore, when the outer diameter of the camera side cable connector 12a is decreased, it is possible to decrease the outer diameter of the camera support tube 13. Accordingly, a special effect that minimal invasiveness is improved. In other words, it is desirable that the outer diameter of the camera side cable connector 12a as small as possible. For example, as illustrated in FIG. 10, it is preferable that the outer diameter of the camera side cable connector 12a becomes smaller than the outer diameter of the equipment side cable connector 16a.

In addition, in FIG. 10, it is described that the outer diameter of the camera side cable connector 12a is greater than the real outer diameter for making the drawings easy to understand. In reality, as described above, the outer diameter of the camera side cable connector 12a is smaller than the outer diameter of the camera support tube 13. In addition, in FIG. 10, the number of pins inserted into the camera side cable connector 12a is set to be 1, but for simplification, in general, the number of pins becomes the number of pins which corresponds to the number of electric wires used as the cable. This is also similar in other drawings.

<Camera Support Tube>

As illustrated in FIG. 10, the camera support tube 13 is a support tube which supports the camera unit 11 as being joined to the camera unit 11 on the inside of the body in a state where the camera side cable 12 passes through the inside thereof, and is drawn out toward the outside of the body.

From the viewpoint of the joining strength with the camera unit 11, the camera support tube 13 is formed of a hard material. The material of the camera support tube 13 is not particularly limited if the material has rigidity which makes it possible to obtain the joining strength that can stably support the camera unit 11, and which makes it possible to fix the camera unit 11 at a desirable position and orientation. For example, stainless steel, ceramics (fine ceramics), or reinforced plastic may be used.

One end part 13a (first end part) of the camera support tube 13 is guided toward the inside of the body through the body wall 41, such as an abdominal wall. At this time, one end part 13a of the camera support tube 13 may be directly guided toward the inside of the body. In addition, the needle-like puncturing device 6 which is used in puncturing may be used as it is as the camera support tube 13. A method of use of the puncturing device 6 as the camera support tube 13 will be described later in a modification example 2.

The end part 13a guided toward the inside of the body joins with the camera unit 11 by the support tube joining unit 14.

Here, a structure of the camera support tube 13 will be described in more detail with reference to FIGS. 12(a) to 12(c).

FIG. 12(a) is a perspective view illustrating an example of the camera support tube 13 according to the embodiment, FIG. 12(b) is a sectional view illustrating each of sections of the camera support tube 13 illustrated in FIG. 12(a) and the support tube joining unit 14 illustrated in FIG. 11(a), and FIG. 12(c) is a sectional view illustrating a joined state of the camera support tube 13 and the support tube joining unit 14 which are illustrated in FIG. 12(b). In addition, in FIG. 12(c), the camera side cable 12 is omitted.

As illustrated in FIG. 12(a), the camera support tube 13 preferably has a cylindrical tube structure. As the camera support tube 13 has a cylindrical shape, as will be described in Embodiment 3 later, it is easy to combine the camera support tube 13 with a general cannula which is the same cylindrical tube.

One end part 13a (inside of the body) of the camera support tube 13 and the camera unit 11 on the inside of the body join with each other by the support tube joining unit 14 (joining unit).

As illustrated in FIGS. 12(a) to 12(c), the camera support tube 13 includes a locking male screw 123 which is screwed (screw-fitted) to the locking female screw 23 provided in the support tube joining unit 14, at the end part 13a on a side which is guided toward the inside of the body.

As the locking male screw 123 of the camera support tube 13 is screwed to the locking female screw 23 of the support tube joining unit 14 in this manner, it is possible to join the camera unit 11 and the camera support tube 13 to each other with high mechanical strength.

In addition, as illustrated in FIG. 12(a), it is desirable that a slit 223 is provided on a side surface of the camera support tube 13.

The camera support tube 13 illustrated in FIG. 12(a) has a structure in which the linear slit 223 which reaches from one opening (inside of the body) to the other opening part (outside of the body) is provided along the axis of the camera support tube 13 on the side surface of the cylindrical tube, and has the locking male screw 123 at the end part which is guided toward the inside of the body. In addition, the width of the slit 223 is greater than the diameter of the camera side cable 12 (greater than at least a short diameter of the section of the cable). In addition, it is possible to directly set the presence or the absence of the slit as necessary, and the invention is not limited thereto.

In addition, as illustrated in FIG. 34(a), most of the width of the slit 223 is greater than the diameter of the camera side cable 12, but a part thereof may be smaller than the diameter of the camera side cable 12. For example, regarding both ends of the camera support tube 13, a plurality of pair projections 255 are formed to face each other at both edges of the slit. In this manner, regarding one part 223p of the slit which corresponds to the pair projection 255, the slit width becomes smaller than the cable diameter, and when the camera side cable 12 passes through the camera support tube 13, the camera side cable 12 can be temporarily elastically deformed and passes at the one part 223p of the slit, and after the camera side cable 12 passes, the diameter of the camera side cable 12 returns to the original diameter. Accordingly, the camera side cable 12 do not easily come off of the camera support tube 13, and the workability when installing the camera support tube 13 is considerably improved. In addition, as illustrated in FIG. 34(b), similar effects are achieved even when the pair projections 255 are formed one by one at each of both ends (a tip end and a terminal end of the slit) of the camera support tube 13.

Figure 34:
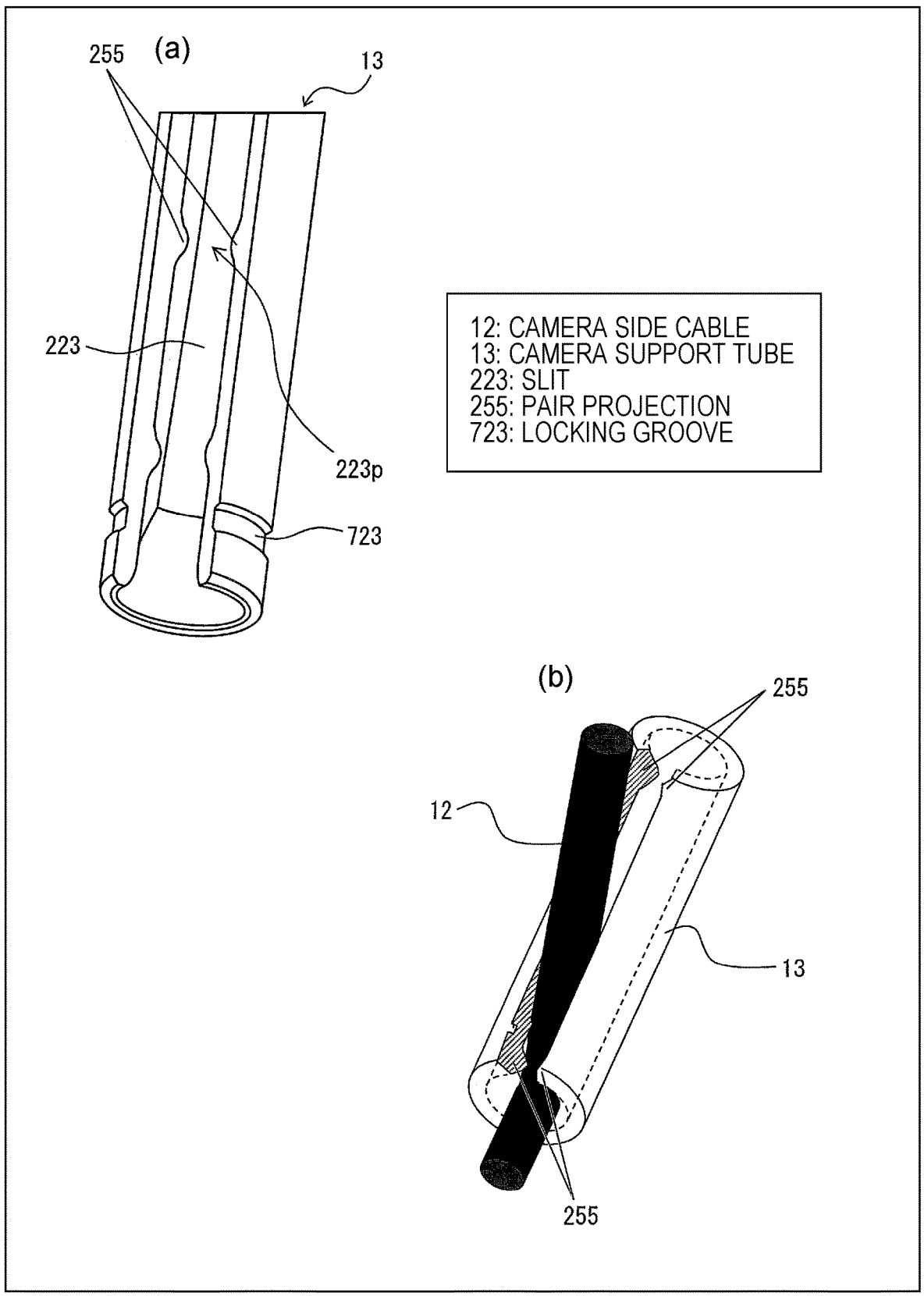
FIGS. 34(a) and 34(b) are perspective views illustrating an example of a shape of a slit provided in the camera support tube.

In FIG. 34, the pair projections 255 are formed on both sides of the one part 223p of the slit 223, but the invention is not limited thereto. As the projection is provided only on one side of a part of the slit 223, a configuration in which the width of a part of the slit 223 becomes smaller than the diameter of the camera side cable 12, can also be employed.

In addition, advantages of a case where the slit 223 is provided on the side surface of the camera support tube 13, will be described later.

<Method for Installing Camera System for Monitoring Inside of Body>

Next, both a method for installing the camera system for monitoring the inside of a body according to the embodiment, and a method of use thereof, will be described.

FIGS. 13(a) to 13(e) and FIGS. 14(a) to 14(e) are schematic views illustrating the method for installing the camera system for monitoring the inside of a body according to the embodiment, in a process order. Since the process in FIGS. 13(a) to 13(d) is the same as that in Embodiment 1, the description thereof will be omitted. In addition, here, FIG. 15 is a modification example with respect to the process of FIG. 14(d).

As illustrated in FIG. 13(e), after further drawing out the handle unit 7y, the connector protection cap having a magnet 8 is removed from the drawing tool 7.

Next, as illustrated in FIG. 14(a), after extracting the puncturing device 6 from the body wall 41, the camera side cable 12 which is guided toward the outside of the body passes through the inside of the camera support tube 13 from the slit 223 on the side surface of the camera support tube 13, and inserts the camera support tube 13 into the body wall 41 by using the camera side cable 12 as a guide. The practitioner inserts the forceps 33 into the body cavity through the trocar 32, grips the support units 22 on both side surfaces of the camera unit 11 using two forceps 33a and 33b so that the support tube joining unit 14 of the camera unit 11 and the opening of the camera support tube 13 become parallel and close to each other, stably holds the posture of the camera unit 11 while pulling the camera side cable 12, and joins the camera support tube 13 and the support tube joining unit 14 to each other by a method of screwing or inserting.

In addition, not using the screw shape, but using the locking claw or the like, similar to modification example 1 which will be described later, in a case where the camera support tube 13 and the support tube joining unit 14 are inserted and fitted to each other, it is desirable that the fitting strength of the camera support tube 13 and the support tube joining unit 14 is set to be smaller than the adhering strength of the adhering and fixing unit of the camera side cable 12 and the camera unit 11. This is because, since it is necessary to grip, pull, support, and insert the cable while guiding the cable when the camera support tube 13 is inserted into the support tube joining unit 14 of the camera unit 11, if the fitting strength of the camera support tube 13 and the support tube joining unit 14 is greater than the adhering strength of the adhering fixing unit, there is a concern that the adhering and fixing unit is damaged and the body wall of the patient is damaged as the camera unit 11 is pulled in the direction toward the outside of the body.

For example, it is desirable that the fitting strength of the camera support tube 13 and the support tube joining unit 14 is equal to or less than 30 N (newton) which is smaller than the adhering strength of the adhering and fixing unit. Furthermore, it is desirable that the most appropriate range is set to be a range of 3 N to 6 N. When the range is set, it is possible to perform the connection without recklessly applying a large force when performing the fitting, and since the feeling that the camera support tube 13 is fitted is transferred to the hand, a special effect that the installation can be performed safely without keeping recklessly applying a force.

Figure 35:
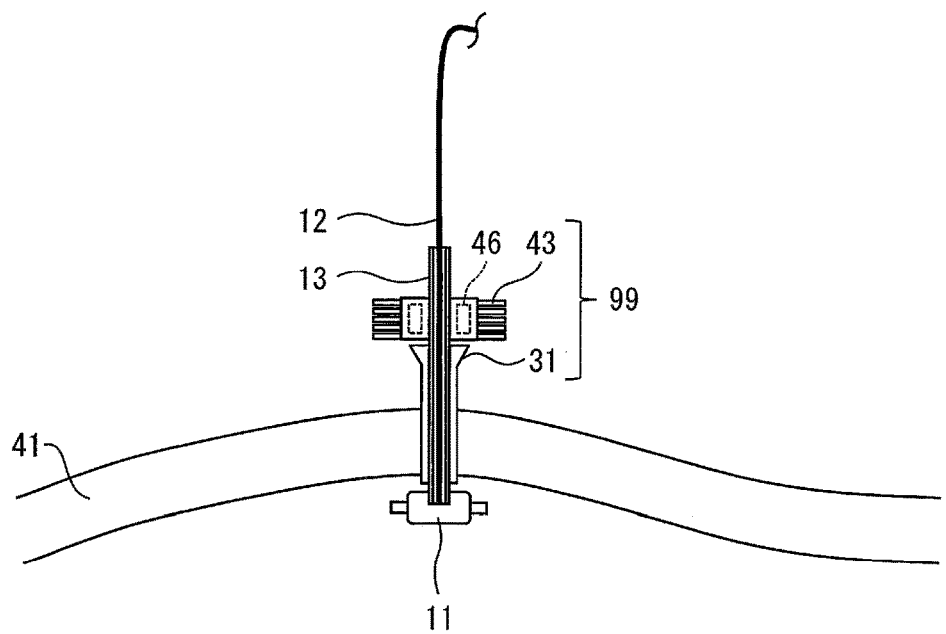
FIG. 35 is a sectional view illustrating a method for radiating heat from the camera support tube.

In addition, at the above-described fitting strength, since the camera support tube 13 and the support tube joining unit 14 sufficiently come into contact with each other, in a case where the side surfaces of the camera support tube 13 and the support tube joining unit 14 are made of a material having high heat conduction properties, the heat generated in the camera unit 11 is transferred to the camera support tube 13 via the support tube joining unit 14, and heat radiation from the part on outside of the body of the camera support tube 13 can be performed. In addition, in order to enhance the effect of heat radiation, as illustrated in FIG. 35, it is also possible to provide a heat sink 43 and a cooling system 99 including a heat radiating fan 46 which sends the wind thereto, on the outside of the camera support tube 13.

Next, in a case of screwing, as illustrated in FIG. 14(b), the camera unit 11 is pulled up to the installation position of the body wall by using the camera support tube 13, and as illustrated in FIG. 14(c), the camera support tube 13 is fixed to the body wall 41 by using the stopper 77.

In a case of inserting, although not illustrated, after fixing the camera side cable 12 and the camera support tube 13 by the cable fastener 43, the camera unit 11 is pulled up to the installation position of the body wall by using the camera support tube 13, and the camera support tube 13 is fixed to the body wall 41 by using the stopper 77.

In addition, in a case of inserting, in order not to make the camera support tube 13 come off of the support tube joining unit 14 provided in the camera unit 11, it is necessary that the cable holding strength of the cable fastener 43 for holding the camera side cable 12 by the camera support tube 13 is greater than the fitting strength of the camera support tube 13 and the support tube joining unit 14. Specifically, for example, in a case where the fitting strength of the inserted camera support tube 13 is 3 N to 6 N, strength which is greater than 3 N to 6 N, that is, strength which is equal to or greater than at least 5 N is necessary. In addition, desirably, it is preferable that the strength is greater than the fitting strength (4 N to 10 N) of the connector protection cap having a magnet 8 and the camera side cable connector 12a. According to this, even when an unexpected force is applied to the camera side cable 12 when removing the connector protection cap having a magnet 8 from the camera side cable connector 12a, the cable fastener 43 does not come off, and the removing is safely performed. In addition, since it is not necessary that the strength is equal to or greater than the strength the camera side cable 12 itself, the most appropriate range is set to be a range of 5 N to 50 N.

In addition, at the above-described cable holding strength, since the camera support tube 13 and the support tube joining unit 14 sufficiently come into contact with each other, in a case where the side surfaces of the camera support tube 13 and the support tube joining unit 14 are made of a material having high heat conduction properties, the heat generated in the camera unit 11 is transferred to the camera support tube 13 via the support tube joining unit 14, and heat radiation from the part on outside of the body of the camera support tube 13 can be performed.

Since the puncturing device 6 is extracted and exchanged with the camera support tube 13, the outer diameter of the camera support tube 13 is smaller than the outer diameter of the puncturing device 6, and for example, can be 3 mm. The diameter of the camera side cable connector 12*a* is approximately 3 mm, but since the slit 223 is provided in the camera support tube 13, the camera side cable 12 having a diameter of approximately 2 mm can pass through the inside. Therefore, the wound when the camera unit 11 is installed is small, minimal invasiveness can be achieved.

Figure 14:
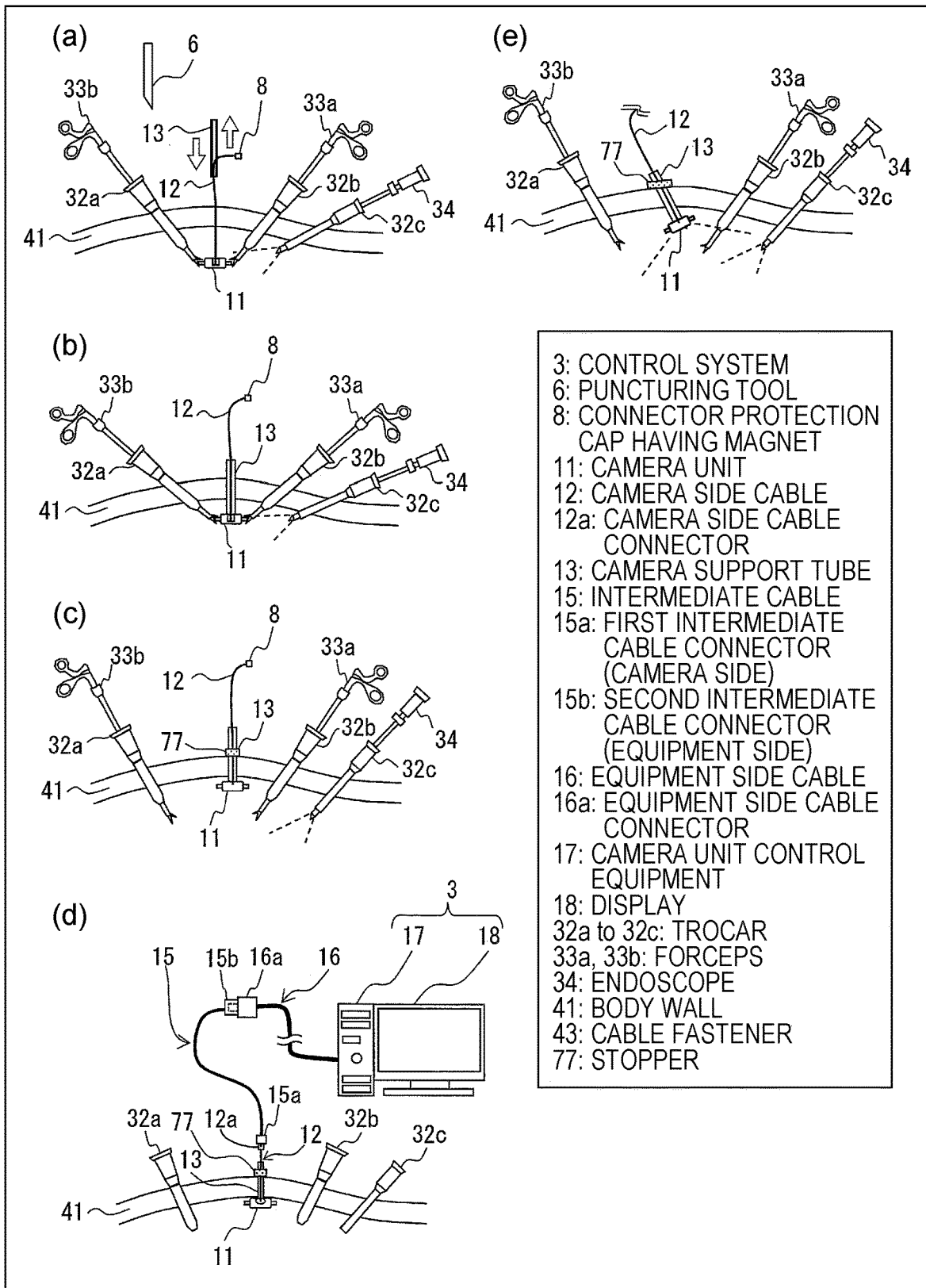
FIGS. 14(a) to 14(e) are schematic views illustrating the method for installing the imaging apparatus in the camera system for monitoring the inside of a body according to Embodiment 2, in a process order following FIGS. 13(a) to 13(e).
Figure 16:
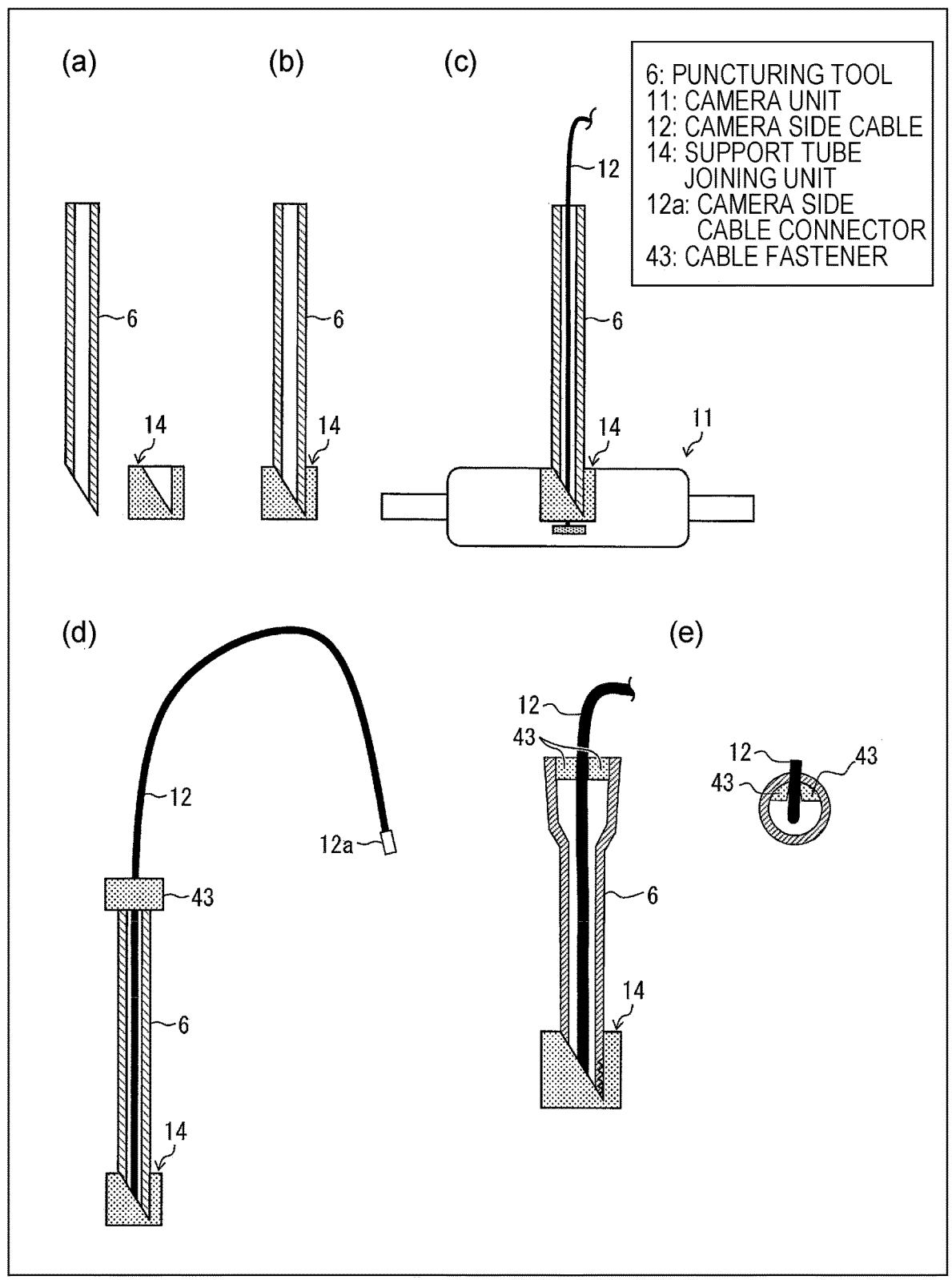
FIG. 16 is a view illustrating a modification example in which the puncturing device is used as the camera support tube according to Embodiment 2.
Figure 17:
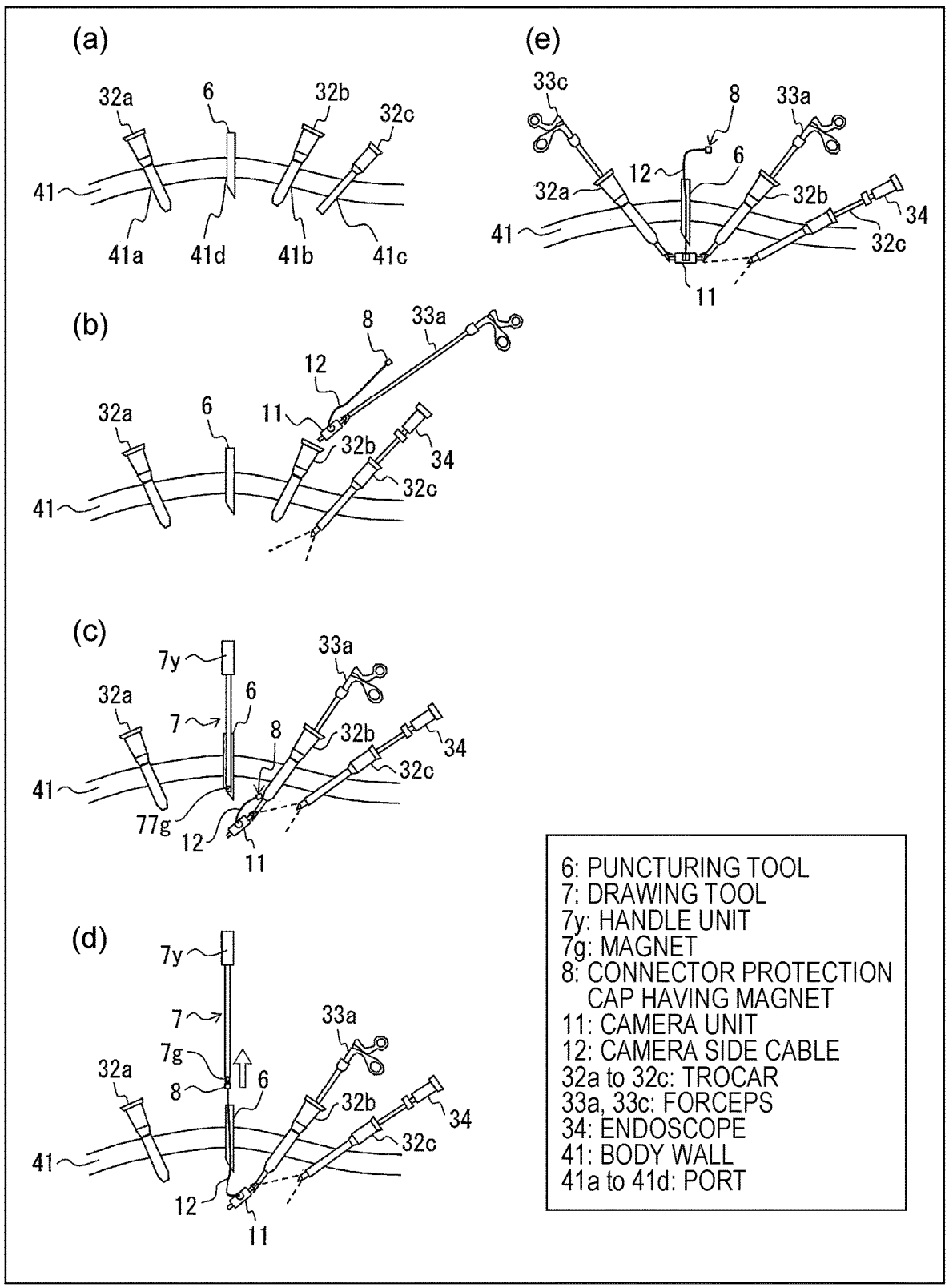
FIGS. 17(a) to 17(e) are schematic views illustrating a method for installing an imaging apparatus in a camera system for monitoring the inside of a body according to the modification example of Embodiment 2, in a process order.
Figure 18:
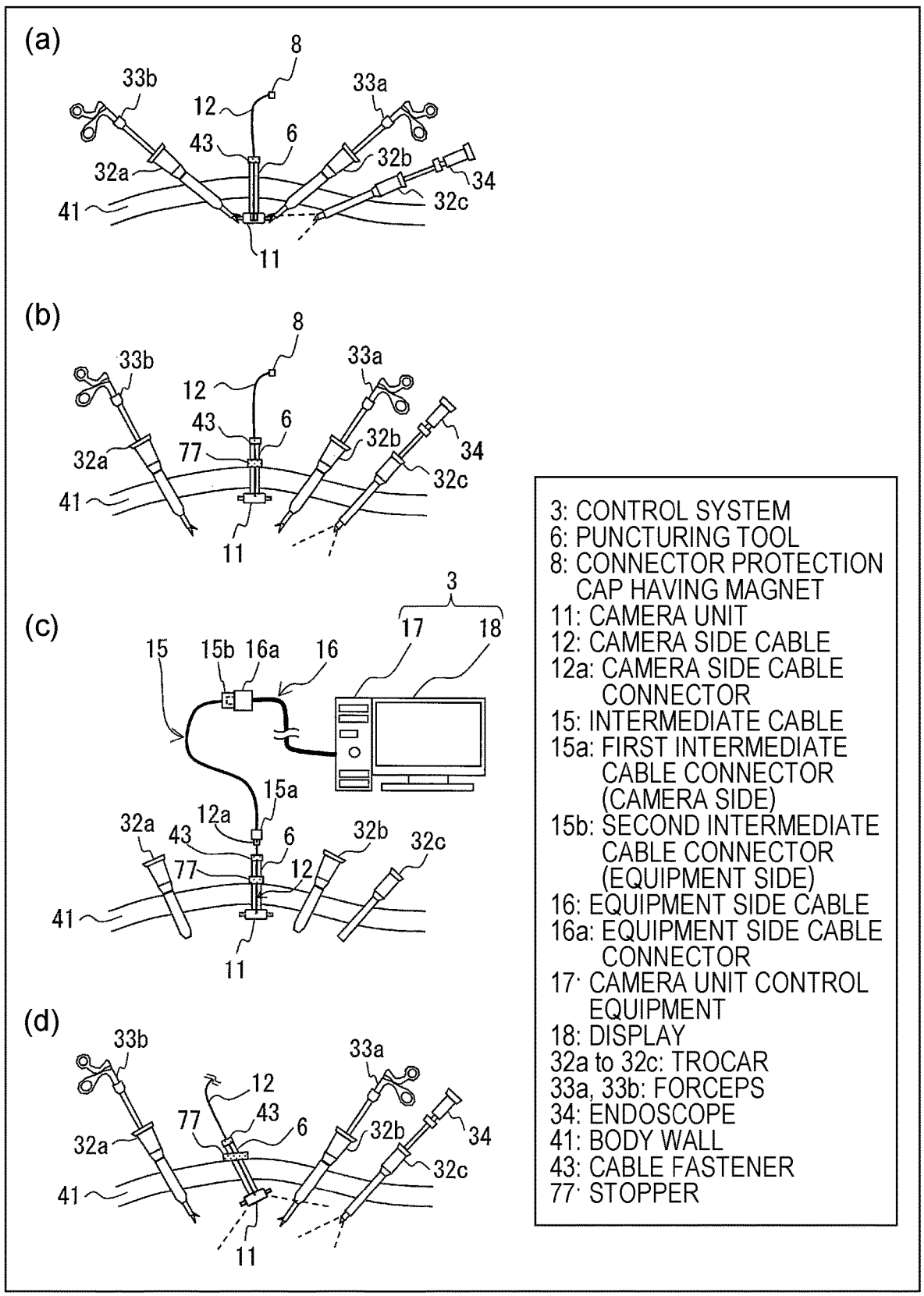
FIGS. 18(a) to 18(d) are schematic views illustrating the method for installing the imaging apparatus in the camera system for monitoring the inside of a body according to the modification example of Embodiment 2, in a process order following FIGS. 17(a) to 17(e).

Next, as a case of screwing is illustrated in FIG. 14(*d*), and a case of inserting is illustrated in FIG. 15, the connector protection cap having a magnet 8 is removed from the camera side cable connector 12*a*, the camera side cable 12 and the intermediate cable 15 are connected to each other by the camera side cable connector 12*a* and the first intermediate cable connector 15*a*, and the intermediate cable 15 and the equipment side cable 16 are connected to each other by the second intermediate cable connector 15*b* and the equipment side cable connector 16*a*. In addition, since the intermediate cable 15 or the equipment side cable 16 does not pass through the inside of the body, the cable having a large diameter can be used.

Accordingly, the entire image of the inside of the body captured by the camera unit 11 is displayed on the display 18 by the camera unit control equipment 17.

Next, as illustrated in FIG. 14(*e*), while seeing the image of the display 18, the camera support tube 13 is operated, the camera unit 11 is moved, the height, the orientation, and the angle on the inside of the body cavity is adjusted, and fixing is performed by a fixing tool. An example of the fixing will be described later by using FIG. 23 combining with Embodiment 3.

After the positioning of the camera unit 11 is completed, the camera system for monitoring the inside of a body 1 is started to be used.

Accordingly, the practitioner can perform treatment using the forceps while enlarging and observing the work region (local region) on the display of the endoscope, and can also grasp the state (movement of the forceps or the like, a bleeding site, and a residual, such as gauze, outside the work region) outside the work region on the display 18.

Figure 13:
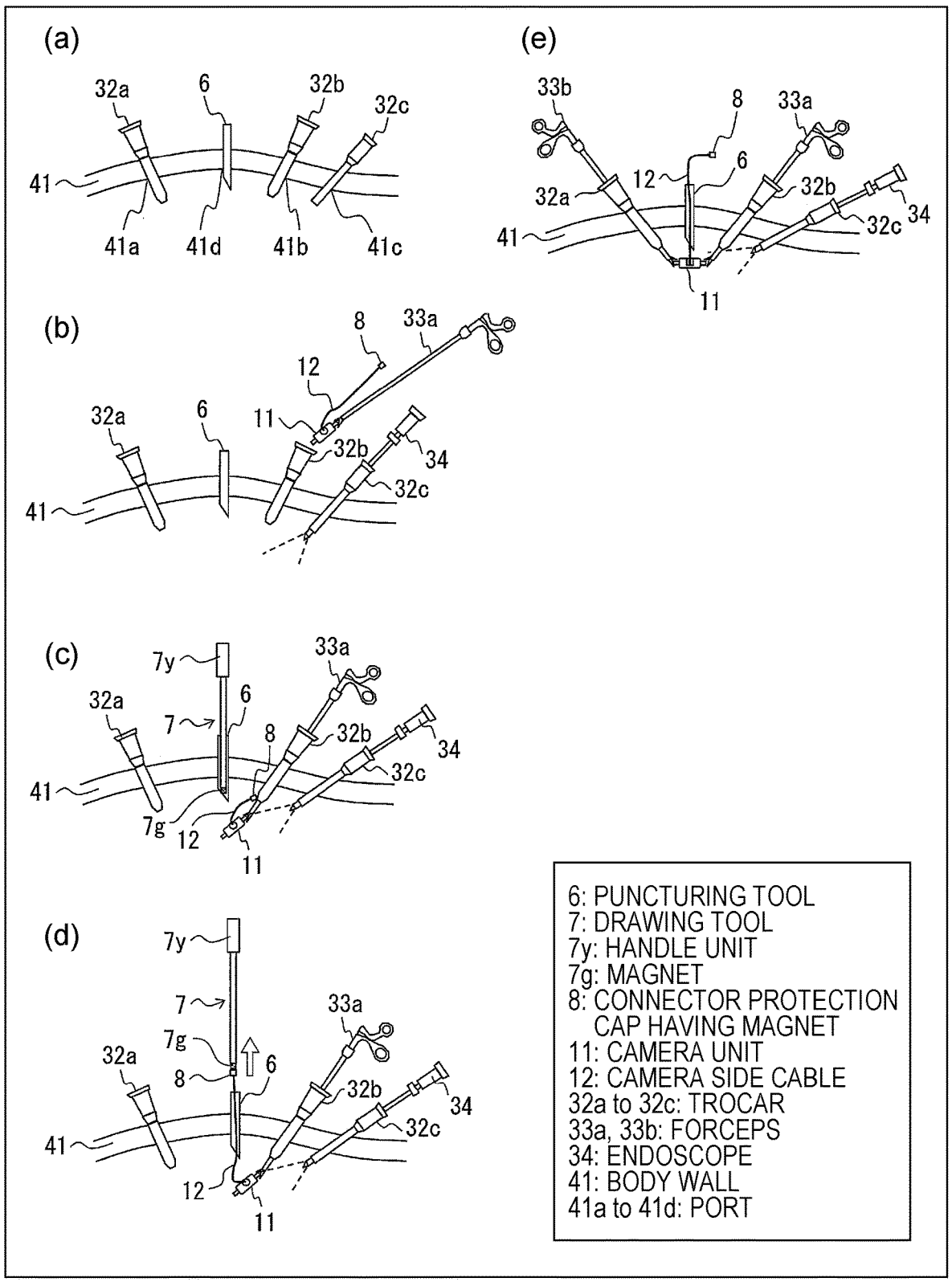
FIGS. 13(a) to 13(e) are schematic views illustrating a method for installing the imaging apparatus in the camera system for monitoring the inside of a body according to Embodiment 2, in a process order.

Furthermore, in the installation method illustrated in FIGS. 13(*a*) to 13(*d*) and FIGS. 14(*a*) to 14(*e*), a method of guiding the auxiliary tool set through the puncturing device 6 is described, but the invention is not limited thereto. After performing the puncturing in the process of FIG. 13(*a*), the puncturing device 6 may be exchanged with the camera support tube 13, and the auxiliary tool set may be guided through the camera support tube 13.

<Method for Collecting Camera Unit>

An order of collecting the camera unit 11 after the surgery is finished, will be described.

First, while the stopper 77 and the cable fastener 43 are removed, and the camera side cable 12 is removed through the slit 223 in a case where the joined camera support tube 13 is inserted, the support tube 13 is extracted to the outside of the body. In a case where the joined camera support tube 13 is inserted, the stopper 77 is removed, the support units 22 on both side surfaces of the camera unit 11 are gripped using two forceps 33*a* and 33*b*, the screwed camera support tube 13 and the support tube joining unit 14 are removed, and the camera support tube 13 is extracted while the camera side cable 12 is removed through the slit 223.

Next, camera side cable connector 12*a* is removed, and the practitioner grips the support unit 22 of the camera unit 11 on the inside of the body using the forceps 33, draws in the pulled camera side cable 12 toward the inside of the body, and then, draws out the camera side cable 12 toward the outside of the body from the trocar 32. Otherwise, the camera side cable 12 may be drawn out of the hole opened for drawing out a cut organ.

Before removing the camera side cable connector 12*a* from the equipment side cable connector 16*a*, in a state where the connectors 12*a* and 16*a* are connected to each other, the work of removing the camera support tube 13 through the slit 223 is possible. Therefore, since there is a low possibility that the camera side cable 12 is mistakenly dropped on the inside of the body during the work, and the camera side cable 12 is lost and it is necessary to search the camera side cable 12, and the work can be efficiently performed during a short period of time, there is a special effect that minimal invasiveness is improved.

In addition, not using the screw shape, but using the locking claw or the like, in a case where the camera support tube 13 and the support tube joining unit 14 are inserted and fitted to each other, similar to the time when the camera unit 11 and the camera support tube 13 are separated, it is desirable that the fitting strength of the camera support tube 13 and the support tube joining unit 14 is set to be smaller than the adhering strength of the adhering and fixing unit of the camera side cable 12 and the camera unit 11. If the fitting strength of the camera support tube 13 and the support tube joining unit 14 is greater than the adhering strength of the adhering and fixing unit, when removing the camera support tube 13 from the camera unit 11, it is necessary to apply a large force, and thus, there is a concern that the adhering and fixing unit is damaged and the body wall of the patient is damaged as the camera unit 11 is pulled in the direction toward the outside of the body.

For example, when the fitting strength is within a range of 3 N to 6 N, it is possible to remove the camera support tube 13 without recklessly applying a large force, and since the feeling that the camera support tube 13 is removed is transferred to the hand, a special effect that the separation can be performed safely without keeping recklessly applying a force.

In addition, the camera side cable connector 12*a* passes via the inside of the body when being collected, and as described above, there is not a problem in maintaining cleanness.

<Effect>

As described above, according to the embodiment, during the endoscopic surgery, it is possible to install an apparatus which can grasp a situation on the inside of the body in a wide viewing field and can substantially enhance safety, during a short period of time without stressing out a practitioner by a simple and safe method only by generating a minimal wound which is equivalent to the size of the outer diameter of the support tube 13.

Modification Example 1

Method for Joining Camera Support Tube and Camera Unit

In the embodiment, a case where the camera support tube 13 and the camera unit 11 are screwed to each other as the locking male screw 123 is provided in the camera support tube 13 and the locking female screw 23 is provided in the support tube joining unit 14, will be described as an example.

However, the method for joining the camera support tube 13 and the camera unit 11 to each other is not limited thereto, and any shape in which the camera support tube 13 and the support tube joining unit 14 are able to be fitted to each other may be employed.

Figure 12:
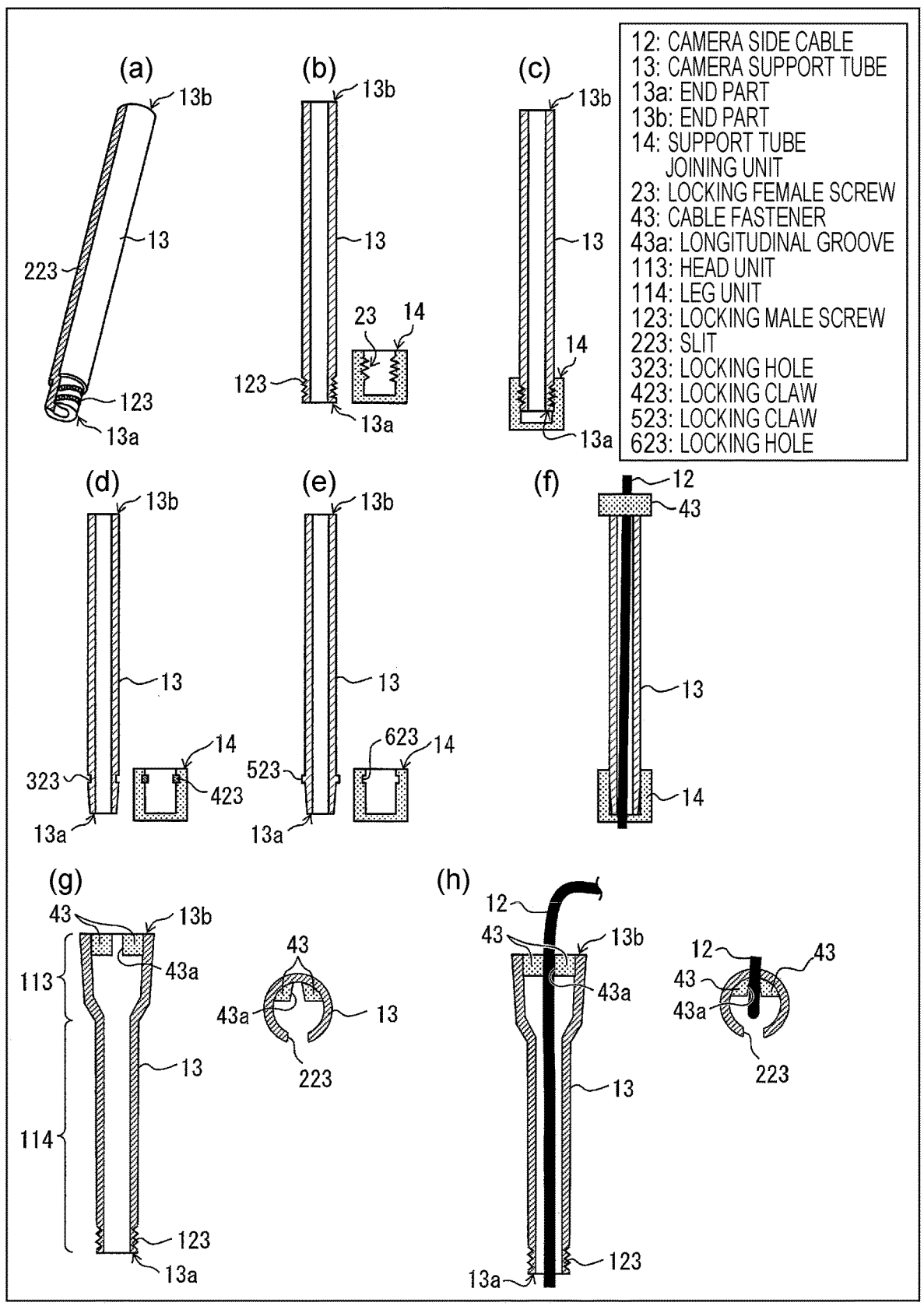
FIG. 12(a) is a perspective view illustrating an example of a camera support tube according to Embodiment 2.
FIG. 12(b) is a sectional view illustrating each of sections of the camera support tube illustrated in FIG. 12(a) and a support tube joining unit illustrated in FIG. 11(a)
FIG. 12(c) is a sectional view illustrating a joined state of the camera support tube and the support tube joining unit which are illustrated in FIG. 12(b). In addition.
FIGS. 12(d) to 12(g) are sectional views illustrating another example of the support tube.
FIG. 12(h) is a sectional view illustrating a state where the camera cable is inserted in FIG. 12(g).

FIGS. 12(*d*) to 12(*h*) are respectively sectional views illustrating modification examples of the camera support tube 13 and the support tube joining unit 14 according to the embodiment.

FIG. 12(*d*) illustrates an example in which a locking hole 323 is provided in the camera support tube 13 and a locking claw 423 is provided in the support tube joining unit 14.

FIG. 12(*e*) illustrates an example in which a locking claw 523 is provided in the camera support tube 13 and a locking hole 623 is provided in the support tube joining unit 14.

In addition, FIGS. 12(*d*) and 12(*e*) are sectional views illustrating each section of the camera support tube 13 and the support tube joining unit 14 in each modification example.

As described in FIGS. 12(*d*) and 12(*e*), in the camera support tube 13 according to the modification example, a part further at a tip part than the locking hole 323 has a tapered shape. Therefore, the tip end (inside of the body) of the camera support tube 13 is not hooked to the locking claw 423 of the support tube joining unit 14, and when pushing the camera support tube 13 until the tip end thereof reaches a deep part of the support tube joining unit 14, the locking hole 323 is fitted to the locking claw 423.

In this manner, in a case where the tip end part of the camera support tube 13 has a tapered shape in order to make it easy to insert the camera support tube 13, it is possible to make the tapered shape by making the thickness of the camera support tube 13 thin. At this time, it is more desirable that the inner diameter of the camera support tube 13 is constant, and only the outer diameter changes (the size of the outer shape is small toward the tip end), since there is not a case where the device is hooked and is not extracted in the middle (at a narrowed location) when inserting the device into the inside of the camera support tube.

However, the camera support tube 13 is not limited to the above-described structure. The thicknesses of both end parts of the camera support tube 13 may be the same.

In addition, a groove-like recessed unit which goes around the outer side surface may be provided at the end part of the camera support tube 13, and a rib-like projected unit which goes around the inner side surface may be provided in the corresponding support tube joining unit 14. In addition, a rib-like projected unit which goes around the outer side surface may be provided at the end part of the camera support tube 13, and a groove-like recessed unit goes around the inner side surface may be provided in the corresponding support tube joining unit 14. This manner is more desirable since it is not necessary to perform an operation of matching the positions of the locking hole and a locking claw when inserting the camera support tube 13, it becomes easy to join both of the camera support tube 13 and the support tube joining unit 14 to each other, and the fitting strength is also strong.

In addition, the camera support tube 13 and the support tube joining unit 14 may be respectively configured of a plurality of materials. For example, the locking claw 423 or the locking claw 523 may be configured of an elastic material, such as a resin. In other words, at least one of the support tube recessed unit and the joining unit projected unit may be configured of an elastic material, such as a resin, and the other one of the support tube recessed unit and the joining unit projected unit may be configured of a hard material, such as metal.

According to this configuration, since the elastic material is deformed and passes through the location which is slightly narrowed and at which the locking claw 423 (elastic material) of the joining unit is disposed, returns to the original shape due to the elastic force after the passage, and completely fitted, the joining strength is improved. The invention is not limited to the example, and at least one of the uneven parts of the support tube and the joining unit may be formed of the elastic material.

In addition, according to this, since the feeling that the claw is fitted is transferred to the hand, the practitioner who performs the operation feels the reaction of the fitting, and can recognize that the fitting is performed, and thus, there is also an advantage that it is not necessary to keep recklessly applying the force.

In addition, when a configuration in which the plurality of materials having different properties are used in order to add functions of enhancing the heat radiation effect from the camera support tube 13 by forming the side surfaces of the camera support tube 13 and the support tube joining unit 14 by a material having high heat conduction properties, enhancing the joining strength using the elastic material only at the projected unit of the support tube joining unit 14, and feeling the reaction of the fitting, is employed, it is possible to achieve the plurality of required functions, such as joining properties and heat radiation properties at the same time.

In addition, regardless of the configuration example of the above-described example, the combination of the materials may be performed in reverse. In other words, the locking claw may be configured of a hard material, such as metal, and a part including the locking hole may be configured of an elastic material, such as a resin.

Figure 40:
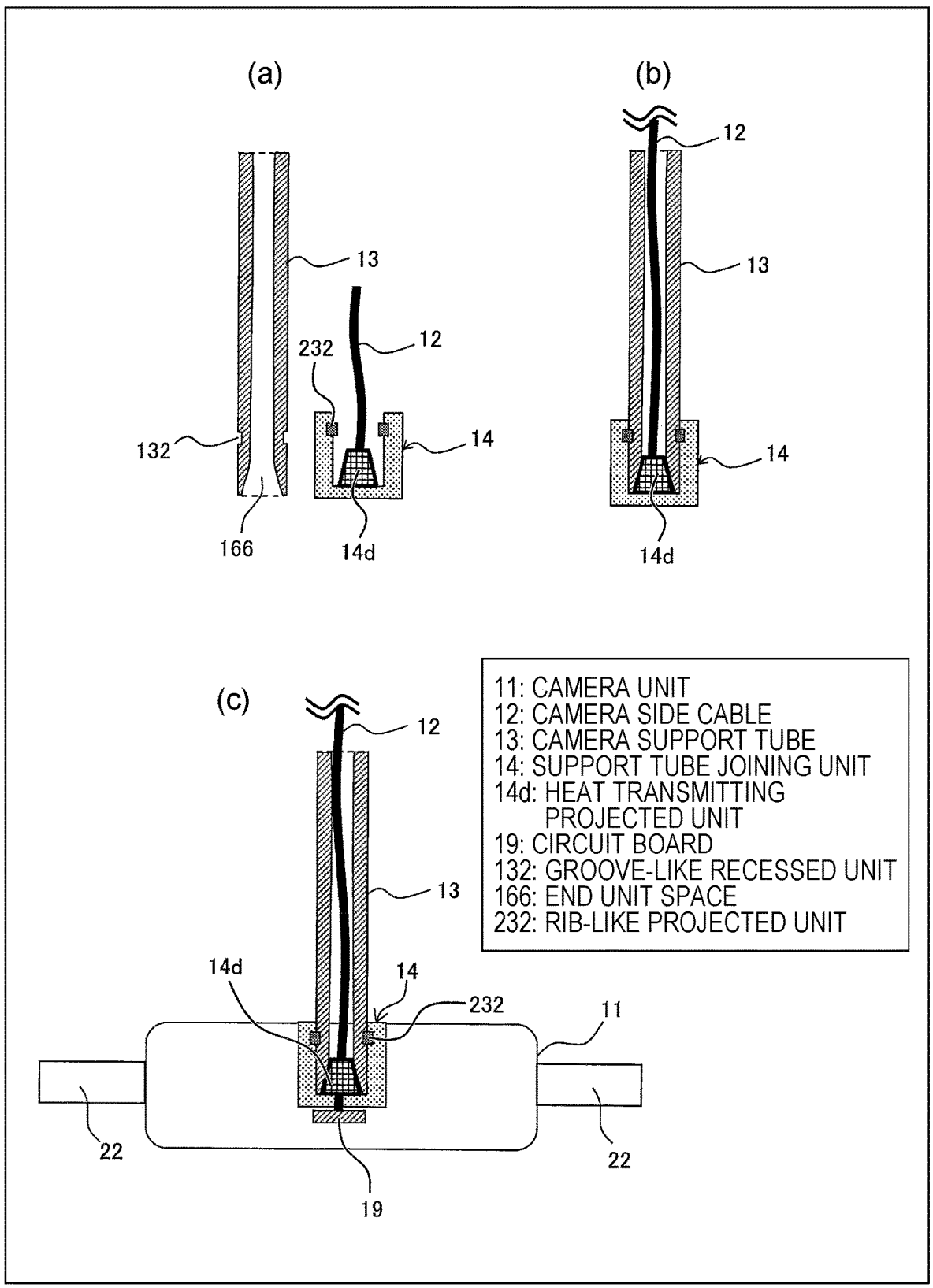
FIG. 40(a) is a sectional view illustrating a modification example of the camera support tube and the support tube joining unit.
FIG. 40(b) is a sectional view illustrating a state where the camera support tube is inserted into the support tube joining unit.
FIG. 40(c) is a sectional view illustrating a joined state of the camera support tube and the camera unit.

FIG. 40 illustrates an example of a configuration in which the above-described joining properties and the heat radiation properties are enhanced. FIG. 40(*a*) is a sectional view illustrating the camera support tube 13 and the support tube joining unit 14, FIG. 40(*b*) is a sectional view illustrating a state where the camera support tube 13 is inserted into the support tube joining unit 14, and FIG. 40(*c*) is a sectional view illustrating a joined state of the camera support tube 13 and the camera unit 11 illustrated in FIG. 11.

As illustrated in FIGS. 40(*a*) and 40(*b*), a groove-like recessed unit 132 which goes around the outer side surface is provided in the camera support tube 13, and a rib-like projected unit 232 which goes around the inner side surface is provided in the corresponding support tube joining unit 14.

Furthermore, the recessed support tube joining unit 14 includes a heat transferring projected unit 14*d* made of a metal material having excellent heat conduction properties, in the bottom part thereof, and the camera side cable 12 is adhered and fixed to the inside of the heat transferring projected unit 14*d*. In this case, the camera side cable 12 is drawn out of the heat transferring projected unit 14*d* of the support tube joining unit 14. An example of adhering and fixing includes sealing and fixing using pressure, an adhesive or an O-ring. Infiltration and incorporation of foreign substances into the camera unit 11 from the adhered and fixed part, are prevented.

More specifically, the heat transferring projected unit 14d has a shape of a truncated cone which is tapered when approaching the opening part (inlet unit) of the support tube joining unit 14, the camera side cable 12 passes through the hole formed in the axial direction, and the camera side cable 12 and the heat transferring projected unit 14d are adhered and fixed in the hole. Regarding the end part (inside of the body) of the camera support tube 13 joined to the support tube joining unit 14, the inside (end part space 166) becomes reverse tapered shape (a shape of which the inner diameter increases when approaching the tip end) which corresponds to the shape of a truncated cone of the heat transferring projected unit 14d. According to this, when joining the camera support tube 13 by using the camera side cable 12 as a guide, since the reverse tapered end part space 166 of the camera support tube 13 is induced to the heat transferring projected unit 14d of the support tube joining unit 14, it becomes easy to insert the camera support tube 13.

In addition, when the camera support tube 13 is fitted to the support tube joining unit 14, the outer circumferential surface of the end part of the camera support tube 13 comes into contact with the inner side wall of the support tube joining unit 14, and the inner circumferential surface of the end part of the camera support tube 13 comes into contact with the heat transferring projected unit 14d of the support tube joining unit 14. Therefore, a special effect that the joining properties of both of the camera support tube 13 and the support tube joining unit 14 increases, and the heat radiation properties of the heat transferred to the camera support tube 13 from the camera unit 11 is further improved, is generated.

In a case where the end part space 166 of the camera support tube 13 has a reverse tapered shape, it is desirable not to make the outer diameter of the camera support tube 13 thick by making the outer diameter of the camera support tube 13 constant, or have a slightly tapered shape, or by making the thickness of the camera support tube 13 toward the tip end thin. According to this, when the camera support tube 13 is inserted into the tube-like device, such as a cannula, it is possible to avoid a situation where the camera support tube 13 is hooked to the inner wall of the tube-like device and is not extracted.

Above, various examples are described, but even in other embodiments, it is needless to say that a plurality of configuration materials of the support tube and the joining unit can be used being similarly combined with each other.

In addition, in the modification examples, a design that the engagement of the locking claw 423 and the locking hole 323 and the engagement of the locking claw 523 and the locking hole 623 are released by applying a force which is equal to or greater than a threshold value, for example, by giving elasticity to the locking claws 423 and 523, or by giving flexibility to the support tube joining unit 14, in order to separate the camera unit 11 and the camera support tube 13, is preferable. Otherwise, a design that the locking claw 423 retracts (that is, changes to a non-projected state) from the inner wall surface of the opening of the support tube joining unit 14, or the locking claw 523 retracts from the surface of the camera support tube 13, by an external force, such as the magnetism or electricity, is desirable.

In addition, instead of joining the camera support tube 13 and the support tube joining unit 14 by using the locking male screw 123 and the locking female screw 23, or the locking claws 423 and 523 and the locking holes 323 and 623, it is possible to join the camera support tube 13 and the support tube joining unit 14 by forming a part of the inner wall of the support tube joining unit 14 by an elastic material, such as rubber, and by pressing the camera support tube 13 into the support tube joining unit 14.

In addition, even in FIG. 12(f), an example of a case where the tip part of the camera support tube 13 has a tapered shape, is illustrated. This case is another modification example in which a method of pulling and fixing the camera side cable 12 without using the locking hole and locking claw is used.

In addition, still another modification example in which the cable fastener 43 is provided in the camera support tube 13, is illustrated in FIGS. 12(g) and 12(h).

FIG. 12(g) is a view in which a sectional view and an upper view of the camera support tube 13 when the cable fastener 43 (locking member) is provided at the end part 13b on the outside of the body in the camera support tube 13, are aligned, and FIG. 12(h) is a view in which a sectional view and an upper view of the camera support tube 13 when the camera side cable 12 passes through the camera support tube 13 are aligned.

As described in Embodiment 1, the camera side cable 12 is connected to the equipment side cable 16 via the connectors 12a and 16a. In the modification example, in order to lock the camera side cable 12 to the camera support tube 13, as illustrated in FIGS. 12(g) and 12(h), the cable fastener 43 (locking member) is provided at the end part 13b of the camera support tube 13.

In addition, according to the embodiment, by fixing the camera side cable 12 to the camera support tube 13 using the cable fastener 43, it is possible to temporarily stop the camera side cable 12 in the middle of the installation work of the camera unit 11, and there is also an advantage that the workability is improved. In addition, even when the camera side cable 12 is pulled on the outside of the body after the installation, there is also an advantage that a load is not applied to the connection unit of the camera unit and the camera side cable 12, and it is possible to prevent the camera side cable from being cut.

(Camera Support Tube)

Here, first, a schematic configuration of the camera support tube 13 according to the modification example will be described.

As illustrated in FIG. 12(g), the camera support tube 13 which is used in the modification example includes a head unit 113 and a leg unit 114, and has a configuration which is similar to that of the camera support tube 13 according to Embodiment 2, except that the camera support tube 13 is a funnel-shaped tube in which the inner diameter of the head unit 113 is greater than the inner diameter of the leg unit 114.

The end part 13a on the leg unit 114 side of the camera support tube 13 according to the modification example is guided toward the inside of the body through the body wall 41, such as an abdominal wall.

In addition, in the modification example, the leg unit 114 of the camera support tube 13 has a cylindrical shape. Therefore, it is easy to combine the camera support tube 13 with a general cannula which is the same cylindrical tube that will be described later in Embodiment 3.

(Cable Fastener)

As described above, in the camera support tube 13 used in the modification example, the end part 13b (outside of the body) on the head unit 113 side has a shape which is thicker than that of the end part 13a on the leg unit 114 side (inside of the body) inserted into the body.

The cable fastener 43 is provided at the end part 13b on the head unit 113 side in the camera support tube 13.

As illustrated in FIGS. 12(g) and 12(h), the cable fastener 43 has a longitudinal groove 43a which extends in the axial direction of the camera support tube 13, and of which the width narrows (a lateral section is tapered in the outward orientation) to the outside (a direction of a side surface) from the center of the camera support tube 13. In addition, as the longitudinal groove 43a, instead of providing the tapered longitudinal groove in the cable fastener 43, the cable fastener 43 is configured of the elastic member, and by providing a cut-out as the longitudinal groove 43a in the cable fastener 43, the camera side cable 12 may also be held using the biasing force by the elastic material.

According to the modification example, in this manner, by fixing the camera side cable 12 to the bottom part (a part having a narrowed width) of the longitudinal groove 43a of the cable fastener 43, it is possible to fix the camera side cable 12 to the camera support tube 13.

Therefore, according to the modification example, it is possible to fix the camera side cable 12 and the camera support tube 13 using the cable fastener 43 as illustrated in FIG. 12(h).

In addition, the cable fastener 43 may be integrally formed with the camera support tube 13, and may be separately formed. In a case of being separately formed, after the camera side cable 12 passes through the camera support tube 13, by inserting the cable fastener 43 which is a separate component into the camera support tube 13, and holding the camera side cable 12 by the cable fastener 43, the camera side cable 12 is held by the cable fastener 43 fixed to the camera support tube 13, and as a result, the camera side cable 12 is held by the camera support tube 13.

Modification Example 2

Method of Using Puncturing Device as Camera Support Tube

In the embodiment, a case where the camera support tube 13 is inserted and the camera unit 11 is fixed after extracting the puncturing device 6, is described as an example.

However, the camera support tube 13 is not limited thereto, and may have a shape in which the puncturing device 6 and the support tube joining unit 14 are fitted to each other, and the puncturing device 6 may be used as the camera support tube 13.

The method thereof will be described by using FIGS. 16(a) to 16(e).

The camera unit 11 illustrated in FIG. 16(c) includes the recessed support tube joining unit 14 (joining unit) on the upper surface thereof. The support tube joining unit 14 has an annular opening shape (hole structure) when viewed from above as illustrated in FIG. 11(b).

FIG. 16(a) is a sectional view illustrating each sections of the puncturing device 6 (functions as both of the support tube and the tube-like member) and the support tube joining unit 14 according to the modification example 2, and FIG. 16(b) is a sectional view illustrating a joined state of the puncturing device 6 and the support tube joining unit 14. In addition, in FIG. 16(b), the camera side cable 12 is omitted. The support tube joining unit 14 has a recessed shape which corresponds to the shape of the needle-like puncturing device 6.

FIG. 16(c) is a view in which the camera unit 11 and the camera side cable 12 are added in FIG. 16(b), and by rotating the puncturing device 6 in the axial direction while pulling the camera side cable 12, it is possible to be fitted to the support tube joining unit 14.

Next, by making the cable fastener 43 pass through the camera side cable 12 while pulling the camera side cable 12, and by pushing the camera side cable 12 to the end part of the puncturing device 6, the camera side cable 12 is fixed. Since the tip end of the puncturing device 6 has an asymmetric shape which is diagonally cut, when the puncturing device 6 is rotated, it is possible to rotate the camera unit 11.

In addition, a structure in which the cable fastener 43 is provided in the puncturing device 6 as illustrated in FIG. 16(e) may be employed. In addition, when the head unit is thicker than the leg unit in this manner, the puncturing device 6 is prevented from being dropped on the inside of the body, and thus, it is possible to further improve safety.

In addition, in order to prevent the puncturing device 6 (camera support tube) from coming off of the support tube joining unit 14 provided in the camera unit 11, it is necessary that the cable holding strength of the cable fastener 43 which holds the camera side cable 12 by the puncturing device 6 (camera support tube) is greater than the fitting strength of the puncturing device 6 (camera support tube). Specifically, for example, in a case where the fitting strength of the inserted puncturing device 6 (camera support tube) is 3 N to 6 N, strength which is greater than 3 N to 6 N, that is, strength which is equal to or greater than at least 5 N is necessary. In addition, desirably, it is preferable that the strength is greater than the fitting strength (4 N to 10 N) of the connector protection cap having a magnet 8. According to this, even when an unexpected force is applied to the cable when removing the connector protection cap having a magnet 8, the cable fastener 43 does not come off, and the removing is safely performed. In addition, since it is not necessary that the strength is equal to or greater than the strength the cable itself, the most appropriate range is set to be a range of 5 N to 50 N.

In addition, at the above-described cable holding strength, since the puncturing device 6 (camera support tube) and the support tube joining unit 14 sufficiently come into contact with each other, in a case where the side surfaces of the camera support tube 13 and the support tube joining unit 14 are made of a material having high heat conduction properties, the heat of the camera unit 11 can be efficiently radiated from the camera support tube 13.

(Method for Installing Camera System for Monitoring Inside of Body)

Next, both the method for installing the system for monitoring the inside of a body according to the modification example 2, and the method of use, will be described.

FIGS. 17(a) to 17(e) and FIGS. 18(a) to 18(d) are schematic views illustrating the method for installing the camera system for monitoring the inside of a body according to the modification example, in a process order. Since the process in FIGS. 17(a) to 17(e) is the same as that in Embodiment 2, the description thereof will be omitted.

As illustrated in FIG. 18(a), after further pulling the drawing tool 7 and drawing out the camera side cable 12 toward the outside of the body through the puncturing device 6, by rotating the puncturing device 6 while pulling the camera side cable 12, it is possible to simply make the puncturing device 6 fit into the support tube joining unit 14. Next, the camera side cable 12 and the puncturing device 6 are fixed to each other by the cable fastener 43.

Next, as illustrated in FIG. 18(b), after fixing the camera side cable 12 and the puncturing device 6 to each other by the cable fastener 43, the camera unit 11 is pulled up to the installation position of the body wall by using the puncturing device 6, and the camera support tube 13 is fixed to the body wall 41 by using the stopper 77.

Since the puncturing device 6 is used as the camera support tube as it is, the installation method becomes simplified, and the installation time is reduced. In addition, when the outer diameter of the puncturing device 6 can be approximately 3 mm when the diameter of the camera side cable connector 12a is approximately 2 mm. Therefore, the wound of the installation unit of the camera unit 11 can be small, and minimal invasiveness can be achieved.

Next, as illustrated in FIG. 18(c), the connector protection cap having a magnet 8 is removed from the camera side cable connector 12a, the camera side cable 12 and the intermediate cable 15 are connected to each other by the camera side cable connector 12a and the first intermediate cable connector 15a, and the intermediate cable 15 and the equipment side cable 16 are connected to each other by the second intermediate cable connector 15b and the equipment side cable connector 16a. Furthermore, since the intermediate cable or the equipment side cable do not pass through the inside of the body, the cable having a large diameter can be used.

Accordingly, the entire image of the inside of the body captured by the camera unit 11 is displayed on the display 18 by the camera unit control equipment 17.

Next, as illustrated in FIG. 18(d), while seeing the image of the display 18, the puncturing device 6 is operated, the camera unit 11 is moved, the height, the orientation, and the angle on the inside of the body cavity is adjusted, and fixing is performed by the fixing tool. An example of the fixing will be described later by using FIG. 23 combining with Embodiment 3.

After the positioning of the camera unit 11 is completed, the camera system for monitoring the inside of a body 1 is started to be used.

Accordingly, the practitioner can perform treatment using the forceps while enlarging and observing the work region (local region) on the display of the endoscope, and can also grasp the state (movement of the forceps or the like, a bleeding site, and a residual, such as gauze, outside the work region) outside the work region on the display 18.

<Method for Collecting Camera Unit 11>

An order of collecting the camera unit 11 after the surgery is finished, will be described.

First, the stopper 77, the camera side cable connector 12a, and the cable fastener 43 are removed, and the puncturing device 6 is extracted to the outside of the body.

Next, the practitioner grips the support unit 22 of the camera unit 11 on the inside of the body using the forceps 33, draws in the pulled camera side cable 12 toward the inside of the body, and then, draws out the camera side cable 12 toward the outside of the body from the trocar 32. Otherwise, the camera side cable 12 may be drawn out of the hole opened for drawing out the cut organ.

<Effect>

As described above, according to the embodiment, during the endoscopic surgery, it is possible to install an apparatus which can grasp the situation on the inside of the body in a wide viewing field and can substantially enhance safety, during a short period of time without stressing out a practitioner by a simple and safe method only by generating a minimal wound which is equivalent to the size of the outer diameter of the puncturing device 6.

Embodiment 3

Still another embodiment of the present invention will be described based on FIGS. 19 to 23 as follows. In addition, in the embodiment, mainly, differences from Embodiments 1 and 2 will be described, configuration elements which have the same functions as those of the configuration elements used in Embodiments 1 and 2 will be given the same reference numerals, and the description thereof will be omitted. In addition, in the embodiment, it is also needless to say modifications similar to those of Embodiments 1 and 2 are possible.

<Schematic Configuration of Camera System for Monitoring Inside of Body>

FIG. 19 is a schematic view illustrating a schematic configuration of the camera system for monitoring the inside of a body 1 according to the embodiment. As illustrated in FIG. 19, the camera system for monitoring the inside of a body 1 according to the embodiment is provided with the camera unit 11 (imaging part) which captures the inside of the body, the camera side cable 12 in which one end is connected to the camera unit 11, the control system 3 including the display 18 (display unit), the equipment side cable 16 in which one end is connected to the control system 3, the connector protection cap having a magnet 8 (first auxiliary tool) connected to the other end of the camera side cable 12, the drawing tool 7 (second auxiliary tool) which includes the rod-like unit 7x connected to the magnet 7g (holding unit) which holds the magnet 8g (held unit) provided in the connector protection cap having a magnet 8, and the magnet 7g, and which draws out the magnet 8g toward the outside of the body from the inside of the body through the inside of the tube-like device in a state of being held by the magnet 7g, the camera support tube 13 (support tube), and the cannula 31. As the camera support tube 13, the needle-like puncturing device used in puncturing may be used as it is. In addition, the equipment side cable connector 16a (projected shape) provided at the other end of the equipment side cable 16 is fitted to the camera side cable connector 12a (recessed shape) provided at the other end of the camera side cable 12, and the camera unit 11 and the control system 3 are electrically connected to each other.

<Camera Support Tube>

As illustrated in FIG. 19, the camera support tube 13 is a support tube which supports the camera unit 11 as being joined to the camera unit 11 on the inside of the body in a state where the camera side cable 12 passes through the inside thereof, and is drawn out toward the outside of the body.

From the viewpoint of the joining strength with the camera unit 11, the camera support tube 13 is formed of a hard material. The material of the camera support tube 13 is not particularly limited if the material has rigidity which makes it possible to obtain the joining strength that can stably support the camera unit 11, and which makes it possible to fix the camera unit 11 at a desirable position and orientation. For example, stainless steel, ceramics (fine ceramics), or reinforced plastic may be used.

Figure 20:
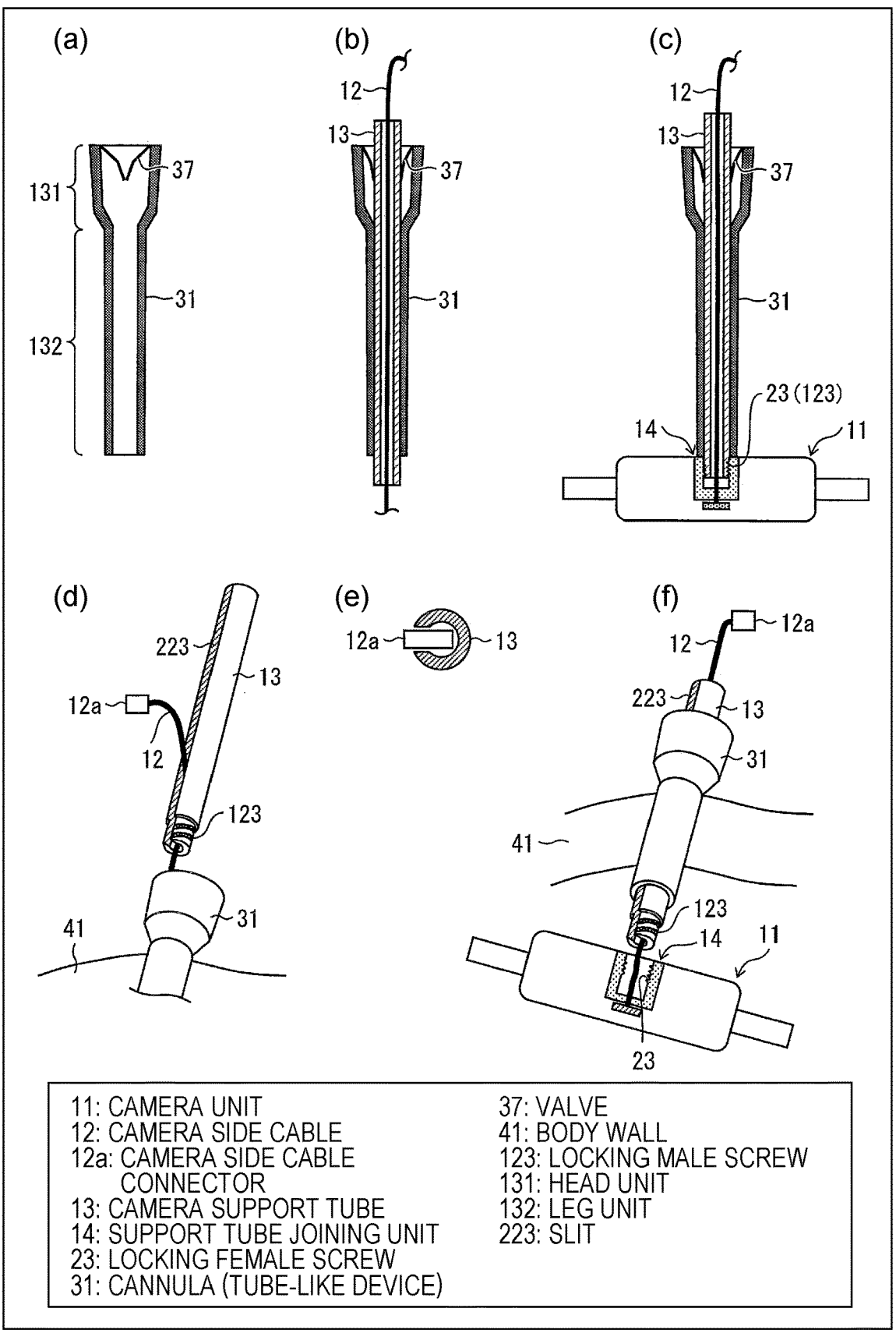
FIG. 20(a) is a sectional view illustrating a schematic configuration of a cannula according to Embodiment 3.
FIG. 20(b) is a sectional view illustrating a state where the camera support tube illustrated in FIGS. 12(a) to 12(f) is inserted into the cannula illustrated in FIG. 20(a)
FIG. 20(c) is a sectional view illustrating an example of a joined state of the camera support tube inserted into the cannula and the camera unit illustrated in FIG. 11.
FIGS. 20(d) and 20(f) are perspective views illustrating a detailed process illustrated in FIG. 22(b)
FIG. 20(e) is a plan view illustrating a relationship between the size of a cable connector illustrated in FIG. 20(d) and the size of the camera support tube.

One end part 13a (first end part) of the camera support tube 13 is guided toward the inside of the body through the body wall 41, such as an abdominal wall. At this time, one end part 13a of the camera support tube 13 may be directly guided toward the inside of the body, or as illustrated in FIG. 20, one end part 13a may be guided toward the inside of the body penetrating the camera support tube 13 on the inside of the cannula 31, by using the cannula 31 inserted into the body wall 41. In addition, as illustrated in the modification example 2, the needle-like puncturing device 6 which is used in puncturing may be used as it is as the camera support tube 13.

In a case where the cannula 31 is used, as the camera support tube 13, the camera support tube 13 which is longer than the cannula 31 in the axial direction is used so that the one end part 13a and the other end part 13b (second end part) are exposed from the cannula 31 in a state the camera support tube 13 is inserted into the cannula 31. In addition, the camera support tube 13 having a size (thickness) to have a void between an outer wall of the camera support tube 13 and an inner wall of the cannula 31 is used in a state of penetrating the camera support tube 13 in the cannula 31 in order to make it possible to rotate the camera support tube 13 around the axis in the cannula 31.

The end part 13a guided toward the inside of the body joins with the camera unit 11 by the support tube joining unit 14.

In addition, it is desirable that the strength for fitting the camera support tube 13 and the support tube joining unit 14 is set to be smaller than the adhering strength of the adhering and fixing unit of the camera side cable 12 and the camera unit 11, in a case where the method for joining the support tube is not a screwing method, and but a fitting method. This is because, since it is necessary to grip, pull, support, and insert the cable while guiding the cable when the camera support tube 13 is inserted into the support tube joining unit 14 of the camera unit 11, if the fitting strength of the camera support tube 13 and the support tube joining unit 14 is greater than the adhering strength of the adhering fixing unit, there is a concern that the adhering and fixing unit is damaged and the body wall of the patient is damaged as the camera unit is pulled in the direction toward the outside of the body.

For example, specifically, it is desirable that the strength for fitting the camera support tube 13 and the support tube joining unit 14 is equal to or less than 30 N (newton) which is smaller than the adhering strength of the adhering and fixing unit. Furthermore, it is desirable that the most appropriate range is set to be a range of 3 N to 6 N. When the range is set, it is possible to perform the fitting without recklessly applying a large force when performing the fitting, and since the feeling that the camera support tube 13 is fitted is transferred to the hand, a special effect that the installation can be performed safely without keeping recklessly applying a force.

In addition, at the above-described fitting strength, since the camera support tube 13 and the support tube joining unit 14 sufficiently come into contact with each other, in a case where the side surfaces of the camera support tube 13 and the support tube joining unit 14 are made of a material having high heat conduction properties, the heat of the camera unit 11 can be efficiently radiated from the camera support tube 13.

<Support Tube Fixing Member>

The camera system for monitoring the inside of a body 1 according to the embodiment is provided with the cannula 31 (holding tube) and a fixing member, as a support tube fixing member (support tube fixing means) which fixes the camera support tube 13 on the outside of the body.

(Cannula 31)

FIG. 20(a) is a sectional view illustrating a schematic configuration of the cannula 31 used in the embodiment, FIG. 20(b) is a sectional view illustrating a state where the camera support tube 13 illustrated in FIGS. 12(a) to 12(h) is inserted into the cannula 31 illustrated in FIG. 20(a), and FIG. 20(c) is a sectional view illustrating an example of a joined state of the camera support tube 13 inserted into the cannula 31 and the camera unit 11 illustrated in FIG. 11.

As illustrated in FIG. 20(a), the cannula 31 which is used in the embodiment is a funnel-like tube (tube-like device) which includes a head unit 131 and a leg unit 132, and in which the inner diameter of the head unit 131 is greater than the inner diameter of the leg unit 132.

Therefore, in the cannula 31, an end part 31b (outside of the body) on the head unit 131 side is greater than an end part 31a on the leg unit 132 side (inside of the body) which is inserted into the body, and when the cannula 31 is inserted into the body wall 41, the head unit 131 functions as a stopper.

Accordingly, there is not case where the camera support tube 13 falls out on the inside of the body, and the cannula 31 can be fixed to the body wall 41.

In addition, the cannula 31 includes a valve 37, and the valve 37 has a valve structure which pressingly expands when an external force is applied toward the thin end part 31a (inside of the body) from the thick end part 31b (outside of the body) at the center part thereof.

Therefore, as illustrated in FIG. 20(b), when the camera support tube 13 is inserted into the cannula 31 through the valve 37, the valve 37 pressingly expands by the camera support tube 13, and the camera support tube 13 is tightly fastened by a biasing force caused by the restoration properties. As a result, the camera support tube 13 is fixed to the cannula 31.

In addition, it is preferable that the diameter of the cannula 31 is small in order to realize minimal invasiveness. Specifically, it is preferable that the diameter of the cannula 31 is equal to or less than 3 mm.

(Fixing Camera Support Tube 13 to Cannula 31 and Joining Camera Support Tube 13 to Camera Unit 11)

Here, a manner of inserting the camera support tube 13 into the cannula 31 and joining the camera support tube 13 to the camera unit 11, will be described with reference to FIGS. 20(b) and 20(c).

In a case where the camera unit 11 joins with the camera support tube 13 on the inside of the body, first, as illustrated in FIG. 20(b), in a state of passing through the camera side cable 12 inside the camera support tube 13, one end part 13a of the camera support tube 13 is pushed against the thick end part 31b (outside of the body) of the cannula 31, and until the end part 13a of the camera support tube 13 is exposed from the cannula 31, the camera support tube 13 is inserted into the cannula 31. At this time, as the valve 37 is pressingly expanded by the camera support tube 13, and the camera support tube 13 is biased due to the restoration properties, the camera support tube 13 is fixed to the cannula 31. In addition, the other end part 13b (outside of the body) of the camera support tube 13 is also exposed from the cannula 31.

Next, as illustrated in FIG. 20(c), by inserting and screwing the locking male screw 123 of the end part 13a on the inside of the body of the camera support tube 13 into the locking female screw 23 of the support tube joining unit 14, the locking male screw 123 is fitted to the locking female screw 23, by using the camera side cable 12 as a guide, and the camera unit 11 and the camera support tube 13 are joined to each other at a high mechanical strength. In addition, the shapes of the locking male screw 123 and the locking female screw 23 are not limited to the screw shape, may be shapes fitted to each other, and instead of the locking female screw 23, a pressing structure or the like in which the elastic material is used can be used.

In addition, not using the screw shape, but using the locking claw or the like, in a case where the camera support tube 13 and the support tube joining unit 14 are inserted and fitted to each other, it is desirable that the fitting strength of the camera support tube 13 and the support tube joining unit 14 is set to be smaller than the adhering strength of the adhering and fixing unit in which the camera side cable 12 and the camera unit 11 are adhered and fixed to each other. This is because, since it is necessary to grip, pull, support, and insert the cable while guiding the cable when the camera support tube 13 is inserted into the support tube joining unit 14 of the camera unit 11, if the fitting strength of the camera support tube 13 and the support tube joining unit 14 is greater than the adhering strength of the adhering fixing unit, there is a concern that the adhering and fixing unit is damaged and the body wall of the patient is damaged as the camera unit is pulled in the direction toward the outside of the body.

For example, specifically, it is desirable that the strength for fitting the camera support tube 13 and the support tube joining unit 14 is equal to or less than 30 N (newton) which is smaller than the adhering strength of the adhering and fixing unit. Furthermore, it is desirable that the most appropriate range is set to be a range of 3 N to 6 N. When the range is set, it is possible to perform the fitting without recklessly applying a large force when performing the fitting, and since the feeling that the camera support tube 13 is fitted is transferred to the hand, a special effect that the installation can be performed safely without keeping recklessly applying a force.

In addition, FIG. 20(c) illustrates a state where the camera support tube 13 is pulled up and the camera unit 11 comes into contact with the end part 13a of the cannula 31 on the inside of the body after joining the camera support tube 13 and the camera unit 11 to each other by the support tube joining unit 14.

The camera support tube 13 is fixed to the cannula 31 which can move in the direction of the external force by applying the external force to the camera support tube 13, for example, by applying the force to the camera support tube 13 by one hand in a state where the practitioner pushes the cannula 31 by the other hand.

In other words, by applying the external force to the camera support tube 13 in the vertical direction (axial direction) or in the rotational direction (circumferential direction), the cannula 31 can move the camera support tube 13 in the vertical direction or in the rotational direction, and when the external force is not applied, the camera support tube 13 can be maintained (fixed) at an arbitrary position in the height direction and in the rotational direction of the camera support tube 13.

(Fixing Member)

A fixing tool (second fixing member) which fixes the camera support tube 13 in a state of being maintained at a constant angle with respect to a body surface 45, by fixing the camera support tube 13 to a fixture (fixed body) fixed to the outside of the body, will be described.

FIGS. 23(a) to 23(c) are perspective views illustrating an example of a schematic configuration of main parts of the camera system for monitoring the inside of a body 1 according to the embodiment. FIGS. 23(a) to 23(c) are respectively perspective views illustrating an example of the support tube fixing member.

<Example 1 of Support Tube Fixing Member>

As illustrated in FIG. 23(a), the camera system for monitoring the inside of a body 1 according to the example includes the cannula 31 illustrated in FIGS. 20(a) to 20(c), and a fixing device 141 (dedicated device), as the support tube fixing member.

In the example, as the fixing tool, by using the dedicated fixing device 141 which can directly fix the camera support tube 13 to the body surface 45, the camera support tube 13 which is fixed to the cannula 31 is fixed.

The fixing device 141 according to the example includes a support table 144 provided with an adhesive layer, which is not illustrated, on one surface (contact surface which is in contact with the body surface 45); an accessory band 145 (belt-like string) which is fixed to a surface opposite to the adhesive layer in the support table 144; and an adjuster 146 which adjusts the fixing length of the band 145.

In the band 145, while one end part is directly fixed to the support table 144, the other end part is fixed to the support table 144 via the adjuster 146. The fixing length of the band 145 can be arbitrarily adjusted by adjusting the length from a fixing end 145a of the band 145 which is directly fixed to the support table 144, to the adjuster 146 which fixes the other end part of the band 145 that is a free end to the support table 144.

In the example, by fixing the cannula 31 which fixes the camera support tube 13, to the support table 144 by the band 145, in a state where the fixing device 141 is fixed to the body surface 45 by the adhesive layer, the camera support tube 13 is fixed to the body surface 45 via the cannula 31.

Therefore, in the example, the practitioner can also operate the camera support tube 13 and can also change the rotational direction or the imaging zoom (distance to the object) of the visual field of the camera unit 11 by easily rotating the camera support tube 13 in the circumferential direction, by pushing the camera support tube 13 to the inside of the body, and by pulling up the camera support tube 13 to the outside of the body.

In addition, by adjusting the fixing position of the cannula 31 by the band 145, it is possible to change the fixing angle (inclination) of the cannula 31 and the camera support tube 13 with respect to the body surface 45. Accordingly, it is also possible to fix the cannula 31 and the camera support tube 13 at a desirable angle, and to arbitrarily change the direction of the visual field of the camera unit 11.

Accordingly, it is possible for the camera support tube 13 to be fixed in a desirable state.

In the example, the adjuster 146 is used in adjusting the fixing length of the band 145 as illustrated in FIG. 23(a), but a method for adjusting the fixing length of the band 145 is not limited thereto. For example, instead of using the adjuster 146, as the band 145, a band provided with a surface fastener, such as a magic tape (registered trademark), may be used.

In the example illustrated in FIG. 23(a), a case where the cannula 31 is tied to the support table 144 by fastening (pressing) the cannula 31 with the band 145, is described, but the camera support tube 13 may be tied to the support table 144 by fastening (pressing) the camera support tube 13 by the band 145.

In a case where the camera support tube 13 is fastened by the band 145, the camera support tube 13 may be fixed at a desirable position by fastening the support tube 13 with the band 145 again after adjusting the fixing length of the band 145, loosening the band 145, moving the support tube 13 or the support table 144, and adjusting the position of the support tube 13. Otherwise, by adjusting the fixing length of the band 145, giving elasticity to the band 145, and adjusting fastening strength, the support tube 13 may be fixed so that the support tube 13 can be moved as a force which is equal to or greater than a certain level is applied to the support tube 13.

In the example, as described above, a case where the cannula 31 illustrated in FIGS. 20(a) to 20(c) is used as the cannula 31, is described as an example. However, in a case where the camera support tube 13 is fastened by the band 145, since the movement of the camera support tube 13 is further restricted by the band 145, the camera support tube 13 is not necessarily fixed to the cannula, and a general cannula can be used as the cannula.

The shape or the material of the dedicated fixing device which is used in the above-described example are not particularly limited if the fixing device can be fixed to the body surface.

In addition, in the above-described example, a case where each fixing device is fixed to the body surface is described as an example, but the embodiment is not limited thereto.

For example, the camera support tube 13 or the cannula 31 may be fixed by the dedicated fixing device installed on an operating table.

For example, as an arm, a so-called joint arm or an articulated arm which has at least one joint unit, can bend the arm by the joint unit, and can freely change a bending angle, is used, the arm may be fixed to the operating table or to the fixing device installed on the operating table or in the operating room, instead of being fixed to the support table or the body surface 45, and the support table provided with the arm may be fixed to the fixing device installed on the operating table or in the operating room. Accordingly, since it is possible to make the reach from the fixing position of the fixing device to a clamp unit long, effects similar to those in a case where the fixing device is fixed to the body surface 45, which is close to the affected part, can be achieved.

<Example 2 of Support Tube Fixing Member>

Another example of the support tube fixing member of the present invention will be described.

FIG. 23(b) is a perspective view illustrating an example of a schematic configuration of main parts of the camera system for monitoring the inside of a body 1 according to the embodiment.

The camera system for monitoring the inside of a body 1 according to the embodiment is provided with the cannula 31 illustrated in FIGS. 20(a) to 20(c) and an adhesive tape 46, as the support tube fixing member.

In the embodiment, by using the adhesive tape 46 which can be directly fixed to the body surface 45, the camera support tube 13 fixed to the cannula 31 is fixed. In addition, in the embodiment, the camera support tube 13 is indirectly fixed to the body surface 45 via the cannula 31.

As the adhesive tape 46, an adhesive tape which has an adhesive layer in a contact unit which is in contact with the body surface, and which is generally used in surgery, can be used. The adhesive tape 46 is provided with the adhesive layer which is not illustrated, on one surface (contact surface which is in contact with the body surface 45), and can be directly fixed to the body surface 45 by adhesive properties of the adhesive layer.

In addition, in the embodiment, the practitioner can also operate the camera support tube 13 and can also change the rotational direction or the imaging zoom (distance to the object) of the visual field of the camera unit 11 by easily rotating the camera support tube 13 in the circumferential direction, by pushing the camera support tube 13 to the inside of the body, and by pulling up the camera support tube 13 to the outside of the body.

In addition, in the embodiment, by changing the fixing position (that is, the position to which a pressing force caused by the adhesive tape 46 is applied to the cannula 31) of the adhesive tape 46 in the cannula 31, it is possible to change a fixing angle (inclination) of the cannula 31 and the camera support tube 13 with respect to the body surface 45. Accordingly, in the embodiment, it is also possible to fix the cannula 31 and the camera support tube 13 at a desirable angle, and to arbitrary change the viewing field direction of the camera unit 11.

In addition, for example, under the cannula 31 (that is, between the cannula 31 and the body surface 45), by nipping an object having a desirable thickness similar to the support table 144 illustrated in FIG. 23(a), as a fixing height adjusting member which adjusts the fixing height of the cannula 31, the fixing angle (inclination) of the cannula 31 and the camera support tube 13 may be changed. In other words, the camera system for monitoring the inside of a body 1 according to the embodiment may further be provided with the fixing height adjusting member which is not illustrated in addition to the cannula 31 and the adhesive tape 46, as the support tube fixing member.

Accordingly, in the embodiment, it is also possible for the camera support tube 13 to be fixed in a desirable state.

In addition, in the example illustrated in FIG. 23(b), a case where the cannula 31 is fixed by the adhesive tape 46 by adhering the adhesive tape 46 to the cannula 31, is illustrated as an example, but in the embodiment, the camera support tube 13 may also be directly fixed by the adhesive tape 46 by adhering the adhesive tape 46 to the camera support tube 13.

In a case where the camera support tube 13 is directly fixed by the adhesive tape 46, in a case where the practitioner changes the position of the support tube 13 after operating the support tube 13, adjusting the position of the support tube 13, and fixing the camera support tube 13 using the adhesive tape 46, the practitioner operates the support tube 13 and adjusts the position of the support tube 13 again by peeling the adhesive tape 46. After this, again, the camera support tube 13 may be fixed by the adhesive tape 46.

Accordingly, even in a case where the camera support tube 13 is directly fixed by the adhesive tape 46, it is possible for the camera support tube 13 to be fixed in a desirable state.

In addition, in the embodiment, in a case where the camera support tube 13 is directly fixed by the adhesive tape 46, since the movement of the camera support tube 13 is further restricted by the adhesive tape 46, the camera support tube 13 is not necessarily fixed to the cannula, and a general cannula can be used as the cannula.

<Example 3 of Support Tube Fixing Member>

Still another example of the present invention will be described based on FIGS. 12(g), 12(h), and 23(c) as follows. In addition, in the embodiment, mainly, differences from other embodiments will be described, configuration elements which have the same functions as those of the configuration elements used in other embodiments will be given the same reference numerals, and the description thereof will be omitted. In addition, in the embodiment, it is also needless to say modifications similar to those of other embodiments are possible.

In the above-described other embodiments, a case where the camera support tube 13 or the cannula 31 which fixes the camera support tube 13, are fixed to the outside of the body by the fixing tool, is described as an example.

In the embodiment, a case where the camera support tube 13 is fixed by fixing the camera side cable 12 to the camera support tube 13, and by fixing the camera side cable 12 to the outside of the body by the fixing tool, is described as an example.

FIG. 12(g) is a view in which the sectional view and the upper view of the camera support tube 13 when the cable fastener 43 (locking member) is provided at the end part 13b on the outside of the body in the camera support tube 13, are aligned, FIG. 12(h) is a view in which the sectional view and the upper view of the camera support tube 13 when the camera side cable 12 passes through the camera support tube 13, are aligned, and FIG. 23(c) is a perspective view illustrating an example of the schematic configuration of the main parts of the camera system for monitoring the inside of a body 1 according to the embodiment.

The camera system for monitoring the inside of a body 1 according to the embodiment is provided with, for example, the cannula 31, the cable fastener 43, and the adhesive tape 46 which are illustrated in FIGS. 12(g), 12(h), and 23(c), and the camera side cable 12 also functions as the support tube fixing member.

As described in Embodiment 1, the camera side cable 12 is connected to the equipment side cable 16 via the connectors 12a and 16a. In the embodiment, in order to lock the camera side cable 12 to the camera support tube 13, as illustrated in FIGS. 12(g) and 12(h), the cable fastener 43 (locking member) is provided at the end part 13b on the outside of the body of the camera support tube 13.

According to the embodiment, by fixing the camera side cable 12 to the bottom part (a part having a narrowed width) of the longitudinal groove 43a of the cable fastener 43, it is possible to fix the camera side cable 12 to the camera support tube 13.

Therefore, according to the embodiment, after the camera side cable 12 and the camera support tube 13 are fixed by the cable fastener 43 as illustrated in FIG. 12(h), by fixing the camera side cable 12 by the adhesive tape 46 or the like as illustrated in FIG. 23(c), it is possible to fix the position of the camera support tube 13.

<Method for Installing Camera System for Monitoring Inside of Body>

Next, both the method for installing the camera system for monitoring the inside of a body according to the embodiment, and the method of use, will be described. In addition, description of parts which are common to those in the installation method of Embodiment 1 will be omitted.

FIGS. 21(a) to 21(e) and FIGS. 22(a) to 22(d) are schematic views illustrating the method for installing the camera system for monitoring the inside of a body according to the embodiment, in a process order. In addition, FIGS. 21(a) to 21(e) and FIGS. 22(a) to 22(d) illustrate a method of guiding one end part 13a of the camera support tube 13 toward the inside of the body by making the camera support tube 13 penetrate the inside of the cannula 31 using the cannula 31.

As illustrated in FIG. 21(a), first, the practitioner opens the ports 41a to 41d (holes) for inserting the forceps or the endoscope into the body cavity on the body wall 41, and inserts each of the plural trocars 32 (hereinafter, referred to as trocars 32a to 32c) into the ports 41a to 41c. Furthermore, the cannula 31 is inserted into the port 41d. As illustrated in FIG. 21(a), in opening the hole of the port 41d, inserting the cannula 31 and opening the hole may be performed at the same time, for example, by using the cannula 31 which inserts the puncturing device 6.

In addition, here, for example, the insertion into the body wall may be performed only by using a device having a puncturing function, such as the trocar, instead of the cannula 31, in the next process, the wire-like drawing tool 7 may be directly inserted into the trocar.

As illustrated in FIG. 21(b), the practitioner extracts the puncturing device 6 from the cannula 31, grips the support unit 22 of the camera unit 11 by using the forceps 33a, and inserts the camera side cable 12 which mounts the connector protection cap having a magnet 8 on the camera side cable connector 12a (not illustrated), and the camera unit 11 into the body cavity in advance.

Next, as illustrated in FIG. 21(c), the practitioner inserts the endoscope 34 into the body cavity through the trocar 32c, grips the support unit 22 of the camera unit 11 by the forceps 33a while observing the inside of the body using the endoscope 34, moves the camera side cable 12 and the camera unit 11 to the lower part of the port 41d, and further, inserts the drawing tool 7 into the cannula 31, and the end part of the camera side cable 12 is absorbed to the connector protection cap having a magnet 8. In the embodiment, since the magnets (7g, 8g) are used in adhering the drawing tool 7 and the connector protection cap having a magnet 8, the absorption is performed by the magnetic force even when the position is slightly deviated, and the operation can be simply performed during a short period of time.

Next, as illustrated in FIG. 21(d), the drawing tool 7 is drawn out of the cannula 31, and the connector protection cap having a magnet 8 to which the camera side cable 12 is connected is drawn out toward the outside of the body. Since the handle unit 7y is present at one more end part of the drawing tool 7, the drawing tool 7 is not mistakenly dropped on the inside of the body, and the operation can be completely performed.

Figure 36:
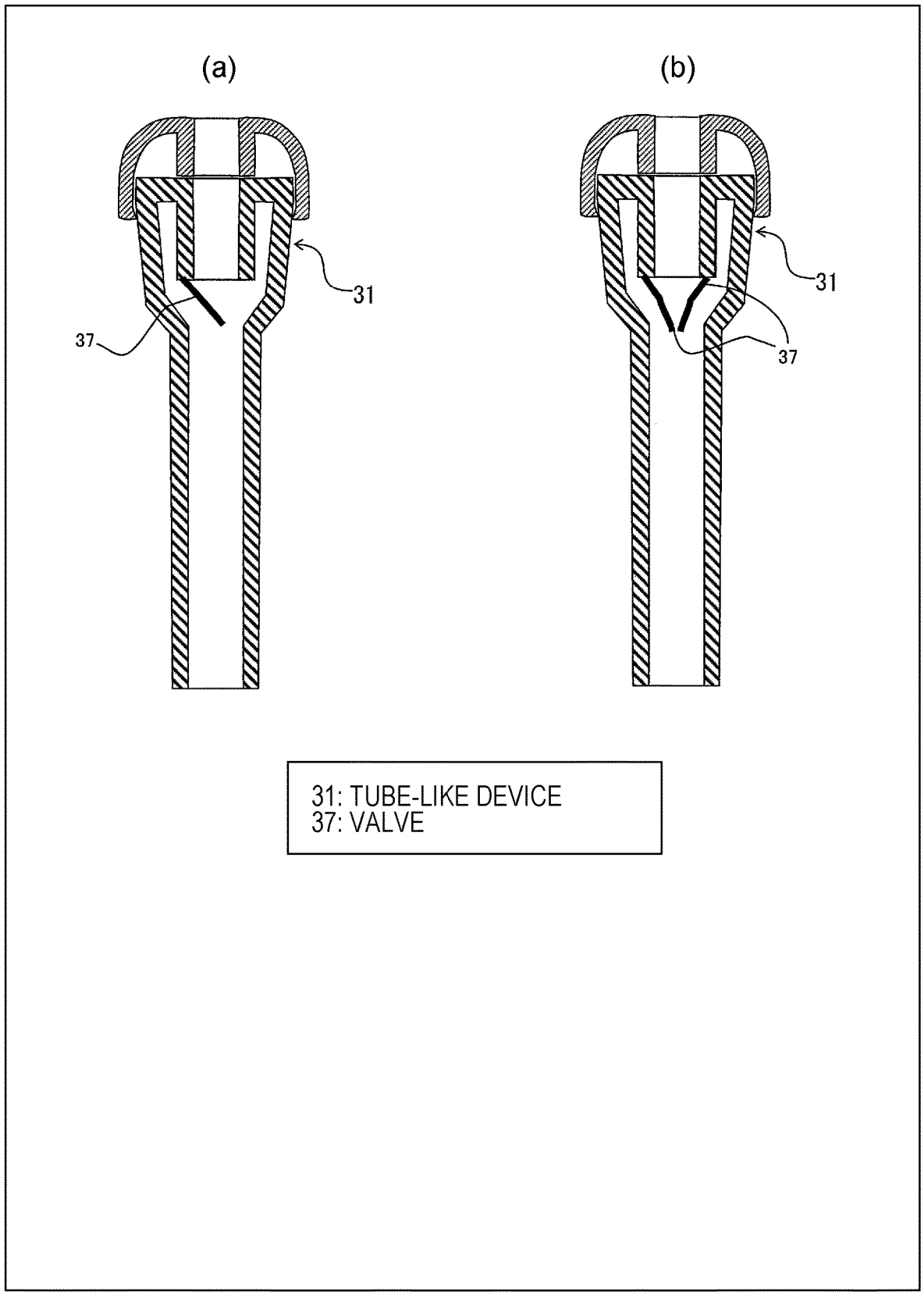
FIGS. 36(a) and 36(b) are sectional views illustrating a configuration example of the cannula.

It is not necessary that the magnetic force of the magnet 8g of the connector protection cap having a magnet 8 to be used at this time has sufficiently large adhering strength for drawing out the camera unit 11 and the camera side cable 12, and additionally, it is necessary to consider the load due to the valve structure of the cannula 31 or the trocar which passes through the inside thereof when drawing out the camera unit 11 and the camera side cable 12. In the tube-like device 31 (tube-like device) which is a trocar or a cannula, there are various types of devices, such as a device made of one valve as illustrated in FIG. 36(a), or a device which opens in a radial shape by both valves as illustrated in FIG. 36(b). In any type of the tube-like device 31, it is necessary to smoothly draw out the connector protection cap having a magnet 8. In addition, in main cannula or trocar which is available in the market, as a result of measuring the load due to the valve, the range of the load was 0.3 N to 0.9 N. Accordingly, the magnetic force may be equal to or greater than at least 1 N. In addition, when the removing is performed after the drawing-out, the adhering strength by which a human being can easily perform the removing by hand is desirable, and since it is necessary that the fitting strength of the connector protection cap having a magnet 8 and the camera side cable connector 12a is further reduced so that the connector protection cap having a magnet 8 does not come off during the drawing-out, it is desirable that the most appropriate range is set to be a range of 1 N to 4 N.

In addition, the load due to the valve is dependent on the shapes of the connector protection cap having a magnet 8 and the camera side cable connector 12a. The connector protection cap having a magnet 8 can have an arbitrary shape corresponding to the shape of the camera side cable connector 12a, but regarding the connector protection cap having a magnet 8 provided with the held unit (magnet 8g) on the cap unit 8c, it is preferable that the length of the connector protection cap having a magnet 8 is equal to or greater than 32 mm.

In addition, as described above, the length only of the connector protection cap having a magnet 8 may be equal to or greater than 32 mm. However, as described above, in a case where the tip end of the camera side cable connector 12*a* is formed to be slightly thin, the connector protection cap having a magnet 8 (provided with the magnet 8*g* on the cap unit 8*c*) is fitted at the thin part, the outer circumference of the end surface of the connector protection cap having a magnet 8 matches the outer circumference of the part (thick part positioned further on the joint side than the end part) which is not the end part of the camera side cable connector 12*a*, and a step is not generated between the side surface of the connector protection cap having a magnet 8 and the side surface of the camera side cable connector 12*a*, the total length of the length of the connector protection cap having a magnet 8 and the length of the part (thick part positioned further on the joint side than the end part) which is not the end part of the camera side cable connector 12*a*, may be equal to or greater than 32 mm. In other words, in a configuration in which a first part and a second part which is narrower than the first part further on the tip end side than the first part are included in the camera side cable connector 12*a* (connector which becomes the other end of the cable), and the outer circumference of the end surface of the connector protection cap having a magnet 8 matches the outer circumference of the first part of the camera side cable connector 12*a* when the connector protection cap having a magnet 8 (first auxiliary tool provided in the held unit on the cap unit) is fitted to the second part of the camera side cable connector 12*a* (connector), the total length of the length of the connector protection cap having a magnet 8 (first auxiliary tool) and the length of the first part of the camera side cable connector 12*a* (connector) is equal to or greater than 32 mm.

Figure 37:
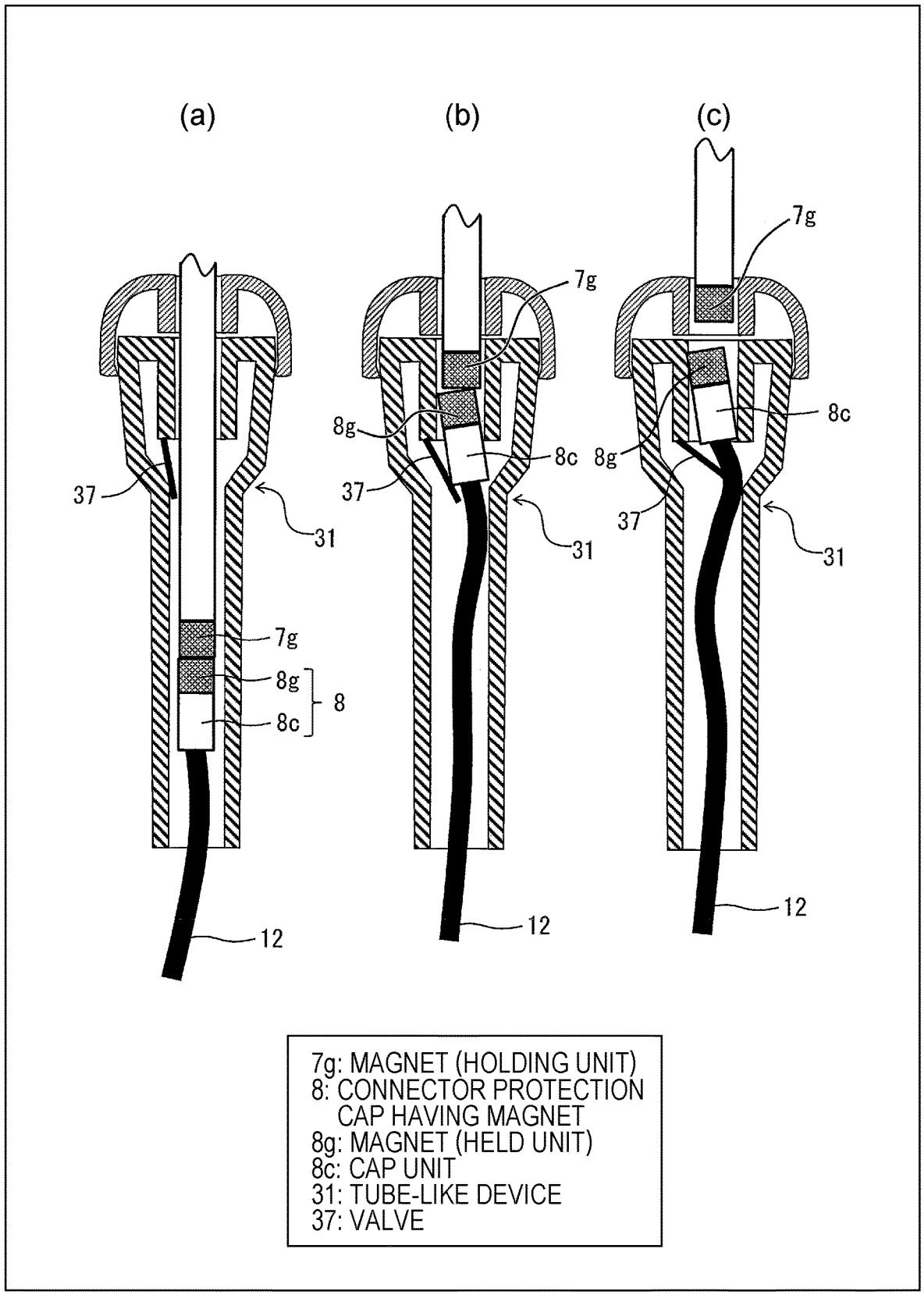
FIGS. 37(a) to 37(c) are sectional views illustrating movement in a single valve cannula in a case where the length of a connector protection cap having a magnet 8 is not desirable.

For example, as illustrated in FIG. 37(*a*), in a case where the inner diameter of the tube-like device 31 in the vicinity of the valve by the one valve, when the connector protection cap having a magnet 8 is short, there is a concern that the entire device is inclined and hooked to the inner wall of the tube-like device 31 when the terminal end of the cap unit 8*c* or the camera side cable 12 is pressed to the valve 37 (FIG. 37(*b*)), and the terminal end of the cap unit 8*c* or the camera side cable 12 comes off of the magnet 7*g* of the drawing tool 7 due to deterioration of the absorption force caused by a decrease in the adhering area (FIG. 37(*c*)). This is because the tip end of the connector protection cap having a magnet 8 does not pass through the tube-like device 31 when the terminal end of the cap unit 8*c* or the camera side cable 12 is pressed to the valve 37. When the tube-like device 31 having a large inner diameter is used, the connector protection cap having a magnet 8 is likely to be more inclined, and is likely to come off.

Figure 38:
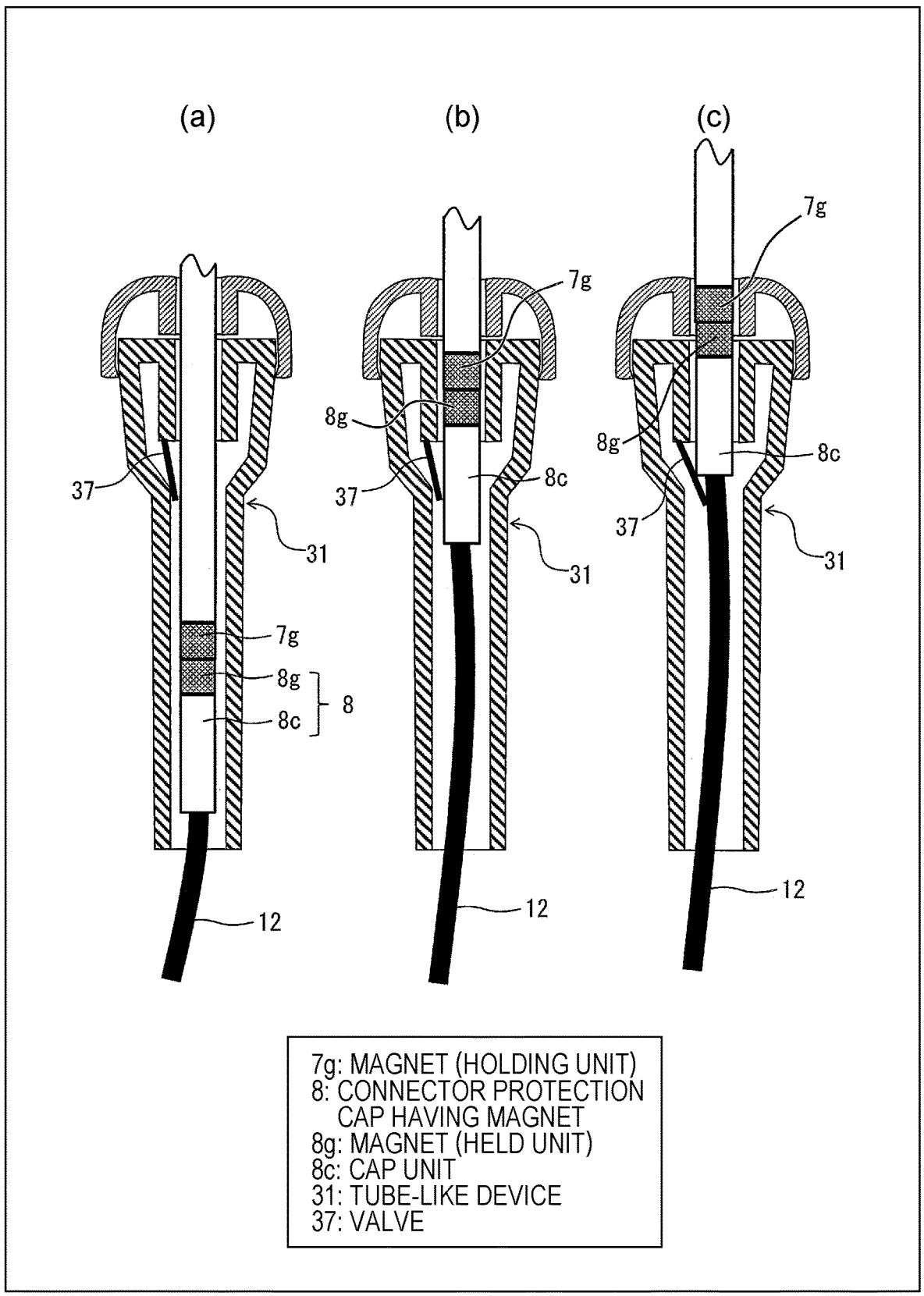
FIGS. 38(a) to 38(c) are sectional views illustrating the movement in the single valve cannula in a case where the length of the connector protection cap having a magnet 8 is desirable.

Meanwhile, in a case where the connector protection cap having a magnet 8 is long as illustrated in FIG. 38(*a*), there is not a case where the connector protection cap having a magnet 8 is rarely inclined even when the terminal end of the connector protection cap having a magnet 8 or the camera side cable 12 is pressed to the valve 37 (FIG. 38(*b*)), and the connector protection cap having a magnet 8 comes off of the magnet 7*g* of the drawing tool 7 (FIG. 38(*c*)). This is because the terminal end of the connector protection cap having a magnet 8 passes through the tube-like device 31 when the terminal end of the connector protection cap having a magnet 8 and the camera side cable 12 is pressed to the valve 37. Therefore, as illustrated in FIG. 5(*a*), regarding the connector protection cap having a magnet 8 provided with the held unit (magnet 8*g*) on the cap unit 8*c*, it is desirable that the length of the connector protection cap having a magnet is longer (for example, equal to or greater than 32 mm) than the length of the part positioned further on the upper side (outside of the body) than the valve 37 of the tube-like device 31. Furthermore, as illustrated in FIG. 5(*e*), regarding the connector protection cap having a magnet 8 having a structure in which the cap unit 8*c* and the held unit (magnet 8*g*) are linked to each other by the linking wire 8*w*, it is desirable that the length of the held unit is longer (for example, equal to or greater than 32 mm) than the length of the part positioned further on the upper side (outside of the body) than the valve 37 of the tube-like device 31.

In other words, it is desirable that the valve 37 (movable member) which movably blocks the tube hole is provided between the opening on the outside of the body and the opening on the inside of the body of the tube-like device 31, the outer shape of the connector protection cap having a magnet 8 does not change from the end surface of the magnet 8*g* to the first distance, and when the distance between the joint of the valve 37 and the opening on the outside of the body of the tube-like device 31 is the second distance, the first distance>the second distance×⅔.

In addition, in a configuration in which the outer circumference of the end surface of the connector protection cap having a magnet 8 matches the outer circumference of the first part of the camera side cable connector 12*a* when the first part and the second part which is narrower than the first part further on the tip end side than the first part are included in the camera side cable connector 12*a* (connector which becomes the other end of the cable), and the connector protection cap having a magnet 8 (first auxiliary tool provided with the magnet 8*g* on the cap unit 8*c*) is fitted to the second part of the camera side cable connector 12*a* (connector), it is desirable that the total length of the length of the connector protection cap having a magnet 8 (first auxiliary tool) and the length of the first part of the camera side cable connector 12*a* (connector) is the first distance, and the first distance>the second distance×⅔.

In addition, in a case where the trocar which is made of a hard material and has a narrow diameter, or of which the inside has a complicated structure, is used as the tube-like device 31, since the connector protection cap having a magnet 8 is likely to be hooked on the inside, the advantage of the aspect is more excellently shown.

In addition, regarding the fitting strength of the camera side cable connector 12*a* and the connector protection cap having a magnet 8, it is necessary that the connector protection cap having a magnet 8 does not come off when drawing out the camera side cable 12, and in a case the magnet is used in the auxiliary tool set, it is desirable that the force is equal to or greater than the magnetic force, for example, 2 N (newton). In addition, during the connection of the connector of the equipment side cable 16 or the intermediate cable 15, strength by which a human being easily performs attachment and detachment when taking out the connector protection cap having a magnet 8, is desirable. Therefore, it is desirable that the most appropriate range is set to be a range of 4 N to 10 N.

Figure 21:
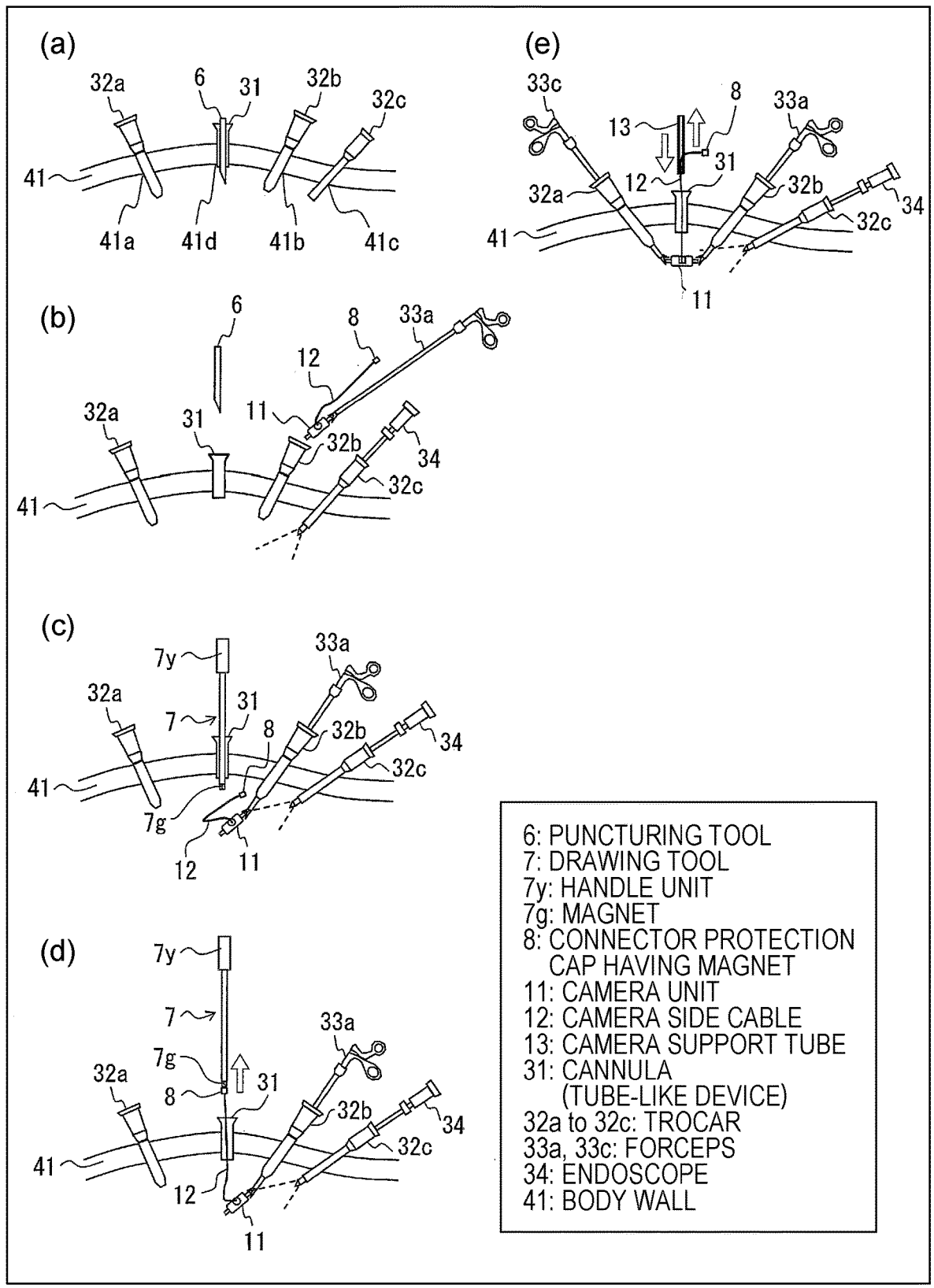
FIGS. 21(a) to 21(e) are schematic views illustrating a method for installing the imaging apparatus in the camera system for monitoring the inside of a body according to Embodiment 3, in a process order.
Figure 22:
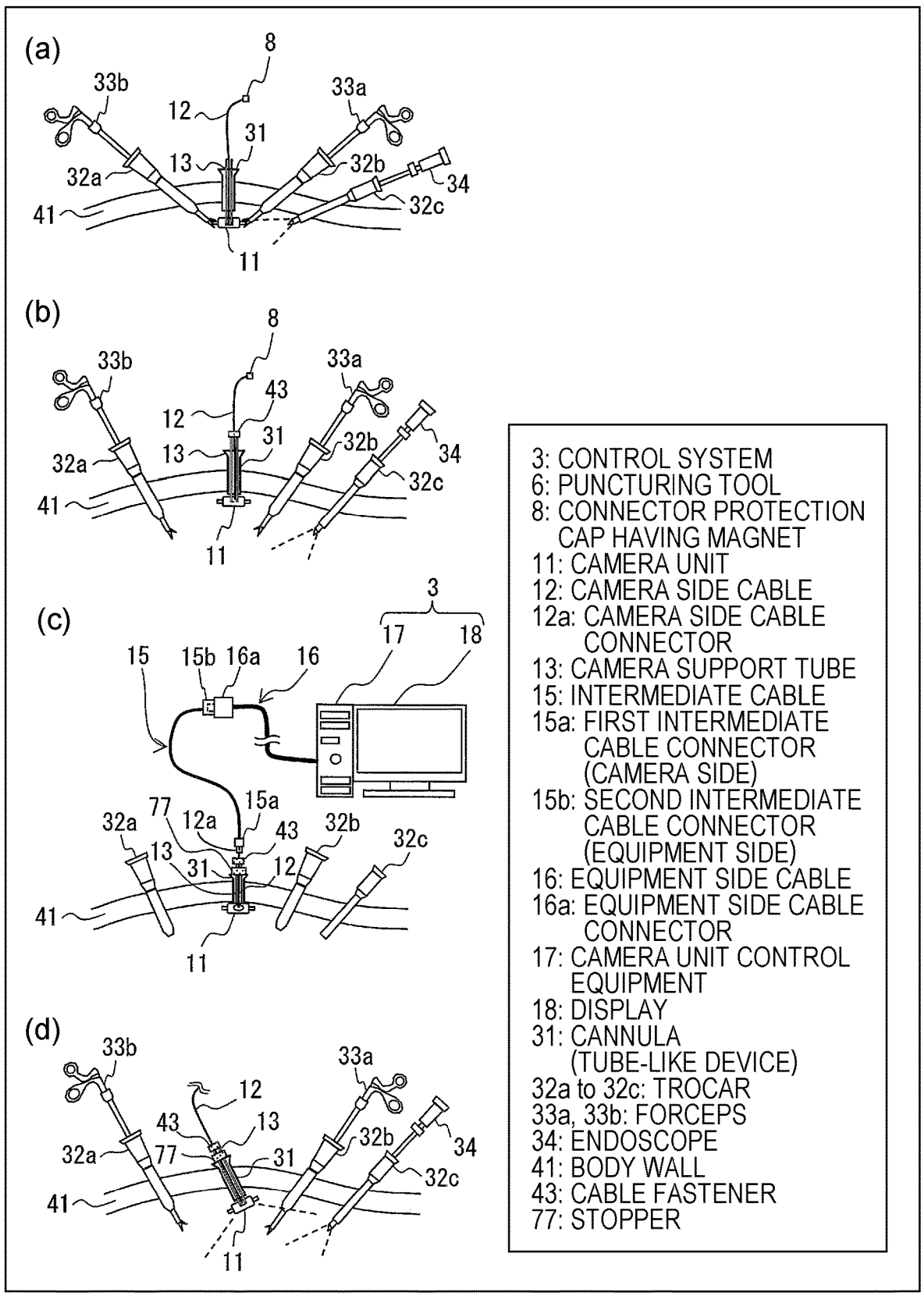
FIGS. 22(a) to 22(d) are schematic views illustrating the method for installing the imaging apparatus in the camera system for monitoring the inside of a body according to Embodiment 3, in a process order following FIGS. 21(a) to 21(e).

Next, as illustrated in FIG. 21(*e*) and FIG. 20(*d*), the camera side cable 12 guided toward the outside of the body, passes through the inside of the camera support tube 13 from the slit 223 on the side surface of the camera support tube 13. At this time, as illustrated in FIG. 20(*e*), a part of the camera side cable connector 12*a* may be exposed from the slit 223 of the camera support tube 13.

In addition, as illustrated in FIG. 34(*a*), a part of the width of the slit 223 may be smaller than the diameter of the camera side cable 12. For example, regarding both ends of the camera support tube 13, the plurality of pair projections 255 are formed to face each other at both edges of the slit. In this manner, the slit width becomes smaller than the cable diameter only at a part of the pair projection 255, and when the camera side cable 12 passes through the camera support tube 13, the camera side cable 12 can be temporarily elastically deformed and passes only at a part of the pair projection 255, and after the camera side cable 12 passes, the diameter of the camera side cable 12 returns to the original diameter. Accordingly, the camera side cable 12 do not easily come off of the camera support tube 13, and the workability when installing the camera support tube 13 is considerably improved. In addition, as illustrated in FIG. 34(b), similar effects are achieved even when the pair projections 255 are formed one by one at each of both ends of the camera support tube 13.

Furthermore, as illustrated in FIGS. 20(f) and 21(e), by using the camera side cable 12 as the guide, the camera support tube 13 is inserted into the cannula 31, and as illustrated in FIG. 22(a), the practitioner inserts the forceps 33 into the body cavity through the trocar 32, grips the support units 22 on both side surfaces of the camera unit 11 using two forceps 33a and 33b so that the support tube joining unit 14 of the camera unit 11 and the opening of the camera support tube 13 become parallel and close to each other, stably holds the posture of the camera unit 11 while pulling the camera side cable 12, and joins the camera support tube 13 and the support tube joining unit 14 to each other by a method of screwing or inserting. In addition, in a case where the camera side cable 12 and the camera side cable connector 12a pass through the inside of the puncturing device 6, in the process of FIG. 21(b), the puncturing device 6 is not extracted and remains as it is, and the puncturing device 6 may be used as the camera support tube 13.

In addition, not using the screw shape, but using the locking claw or the like, in a case where the camera support tube 13 and the support tube joining unit 14 are inserted and fitted to each other, when the camera support tube 13 is inserted into the support tube joining unit 14 of the camera unit 11, the force (for example, 3 N to 6 N) which is necessary for fitting the camera support tube 13 and the support tube joining unit 14 is sufficiently smaller than the adhering strength (for example, equal to or greater than 30 N) of the adhering and fixing unit of the camera unit 11 of the camera side cable 12. Therefore, by pulling the cable while guiding the cable, the camera support tube 13 can be safely inserted and fitted.

Next, in a case of inserting, as illustrated in FIG. 22(b), after fixing the camera side cable 12 and the camera support tube 13 by the cable fastener 43, as illustrated in FIG. 22(c), the camera unit 11 is pulled up to the installation position of the body wall by using the camera support tube 13, and the camera support tube 13 is to the cannula 31 by using the stopper 77.

In addition, since the camera support tube 13 does not come off of the support tube joining unit 14 provided in the camera unit 11, it is necessary that the cable holding strength of the cable fastener 43 which holds the camera side cable 12 by the camera support tube 13 is greater than the fitting strength of the camera support tube 13.

Specifically, for example, in a case where the fitting strength of the inserted camera support tube 13 is 3 N to 6 N, strength which is greater than 3 N to 6 N, that is, strength which is equal to or greater than at least 5 N is necessary. In addition, desirably, it is preferable that the strength is greater than the fitting strength (4 N to 10 N) of the connector protection cap having a magnet 8. According to this, even when an unexpected force is applied to the cable when removing the connector protection cap having a magnet 8, the cable fastener 43 does not come off, and the removing is safely performed. In addition, since it is not necessary that the strength is equal to or greater than the strength the cable itself, the most appropriate range is set to be a range of 5 N to 50 N.

In addition, at the above-described cable holding strength, since the camera support tube 13 and the support tube joining unit 14 sufficiently come into contact with each other, when the side surfaces of the camera support tube 13 and the support tube joining unit 14 are made of a material having high heat conduction properties, the heat of the camera unit 11 is efficiently radiated from the camera support tube 13.

Next, as illustrated in FIG. 22(c), the connector protection cap having a magnet 8 is removed from the camera side cable connector 12a, the camera side cable 12 and the intermediate cable 15 are connected to each other by the camera side cable connector 12a and the first intermediate cable connector 15a, and the intermediate cable 15 and the equipment side cable 16 are connected to each other by the second intermediate cable connector 15b and the equipment side cable connector 16a. Furthermore, since the intermediate cable or the equipment side cable do not pass through the inside of the body, the cable having a large diameter can be used.

Next, as illustrated in FIG. 22(d), while seeing the image of the display 18, the cannula 31 is operated, the camera unit 11 is moved, the height, the orientation, and the angle on the inside of the body cavity is adjusted, and fixing is performed by the fixing tool.

Furthermore, in the installation method illustrated in FIGS. 21(a) to 21(e) and FIGS. 22(a) to 22(d), a method of guiding the auxiliary tool set through the cannula 31 is described, but the invention is not limited thereto. After performing the puncturing in the process of FIG. 21(a), the puncturing device 6 may be exchanged with the camera support tube 13, and the auxiliary tool set may be guided through the camera support tube 13. In addition, instead of the cannula 31, by using the trocar 32, the auxiliary tool set is also guided to the trocar 32.

<Method for Collecting Camera Unit>

An order of collecting the camera unit 11 after the surgery is finished, will be described.

First, the cable fastener 43 is removed, and the practitioner grips the support unit 22 of the camera unit 11 on the inside of the body using the forceps 33, removes the joining of the camera support tube 13 and the support tube joining unit 14, removes the camera side cable 12 through the slit 223, and extracts the camera support tube 13 to the outside of the body. Next, the practitioner removes the camera side cable connector 12a, pulls the camera unit 11 by the forceps 33, draws in the camera side cable 12 toward the inside of the body, and draws out the camera unit 11 toward the outside of the body from the trocar 32. Otherwise, the camera side cable 12 may be drawn out of the hole opened for drawing out the cut organ.

Before removing the camera side cable connector 12a from the equipment side cable connector 16a, in a state where the cable connectors 12a and 16a are connected to each other, the work of removing the camera support tube 13 through the slit 223 is possible. Therefore, since there is a low possibility that the camera side cable 12 is mistakenly dropped on the inside of the body during the work, and the camera side cable 12 is lost and it is necessary to search the camera side cable 12, and the work can be efficiently performed during a short period of time, there is a special effect that minimal invasiveness is improved.

In addition, not using the screw shape, but using the locking claw or the like, in a case where the camera support tube 13 and the support tube joining unit 14 are inserted and fitted to each other, similar to the time when the camera unit 11 and the camera support tube 13 are separated, it is desirable that the fitting strength of the camera support tube 13 and the support tube joining unit 14 is set to be smaller than the adhering strength of the adhering and fixing unit of the camera side cable 12 and the camera unit 11. If the fitting strength of the camera support tube 13 and the support tube joining unit 14 is greater than the adhering strength of the adhering and fixing unit, when removing the camera support tube 13 from the camera unit 11, it is necessary to apply a large force, and thus, there is a concern that the adhering and fixing unit is damaged and the body wall of the patient is damaged as the camera unit is pulled in the direction toward the outside of the body.

For example, when the fitting strength is within a range of 3 N to 6 N, it is possible to remove the camera support tube 13 without recklessly applying a large force, and since the feeling that the camera support tube 13 is removed is transferred to the hand, a special effect that the separation can be performed safely without keeping recklessly applying a force.

In addition, the camera side cable connector 12a passes via the inside of the body when being collected, and as described above, there is not a problem in maintaining cleanness.

<Effect>

In the embodiment, in a case where the practitioner changes the position of the support tube 13 after operating the support tube 13, adjusting the position of the support tube 13, and fixing the camera side cable 12 using the adhesive tape 46, the practitioner also operates the support tube 13 and adjusts the position of the support tube 13 again by peeling the adhesive tape 46. After this, again, the camera side cable 12 may be fixed by the 46.

In addition, for example, under the camera side cable 12 (that is, between the camera side cable 12 and the body surface 45), or according to the situation, under the cannula 31 or the camera support tube 13, by nipping an object having a desirable thickness similar to the support table 144 illustrated in FIG. 23(a), as a fixing height adjusting member, the fixing angle (inclination) of the cannula 31 connected to the camera side cable 12 and the camera support tube 13 may be changed. In other words, in the embodiment, the support tube fixing member may further be provided with the fixing height adjusting member which is not illustrated.

Accordingly, in a case where the camera side cable 12 is directly fixed by the adhesive tape 46, it is also possible for the camera support tube 13 to be fixed in a desirable state.

In addition, in the embodiment, a case where the cannula 31 illustrated in FIGS. 20(a) to 20(c) is used as the cannula 31 as described above, is illustrated as an example, but the camera support tube 13 according to the embodiment is not necessarily fixed to the cannula, and a general cannula can be used as the cannula.

In other words, in the embodiment, by fixing the camera side cable 12 to the camera support tube 13, and by fixing the camera side cable 12 to the outside of the body, it is possible to fix the camera support tube 13 using the camera side cable 12. In other words, by fixing the camera side cable 12 by the adhesive tape 46, the position and the orientation of the camera support tube 13 connected to the camera side cable 12 are fixed. Therefore, similar to a case where the camera support tube 13 is directly fixed to the outside of the body by the fixing tool, the camera support tube 13 may not be fixed to the cannula.

In addition, in the embodiment, as described above, a case where the camera support tube 13 is fixed by fixing the camera side cable 12 to the camera support tube 13 using the cable fastener 43, and by fixing the camera side cable 12 to the outside of the body by the adhesive tape 46, is described as an example. However, the embodiment is not limited thereto, and the camera support tube 13 or the cannula 31, and the camera side cable 12 may be fixed to the outside of the body by the fixing tool, such as the adhesive tape, after fixing the camera side cable 12 to the camera support tube 13 using the cable fastener 43 as described above. It is needless to say that two or more of the camera side cable 12, the camera support tube 13, and the cannula 31 may be fixed. In any case, by fixing the camera side cable 12 to the camera support tube 13 using the cable fastener 43, it is also possible to obtain an effect that improvement of workability and prevention of the camera side cable from being cut are possible, as described above.

Figure 23:
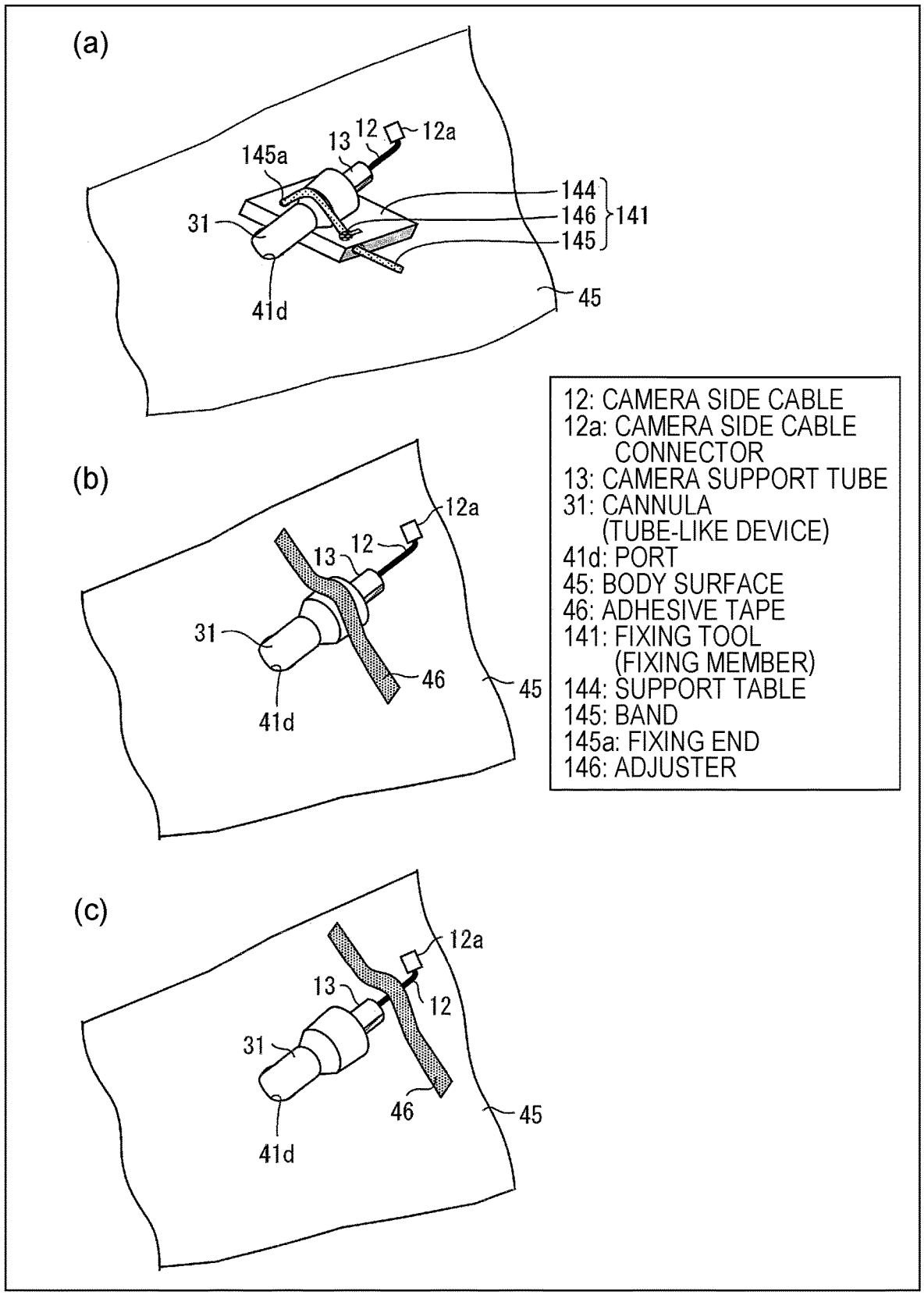
FIG. 23(a) is a perspective view illustrating an example of a schematic configuration of main parts of the camera system for monitoring the inside of a body according to Embodiment 3. In addition.
FIGS. 23(b) and 23(c) are respectively perspective views illustrating another example of the schematic configuration of the main parts of the camera system for monitoring the inside of a body according to Embodiment 3.
Figure 24:
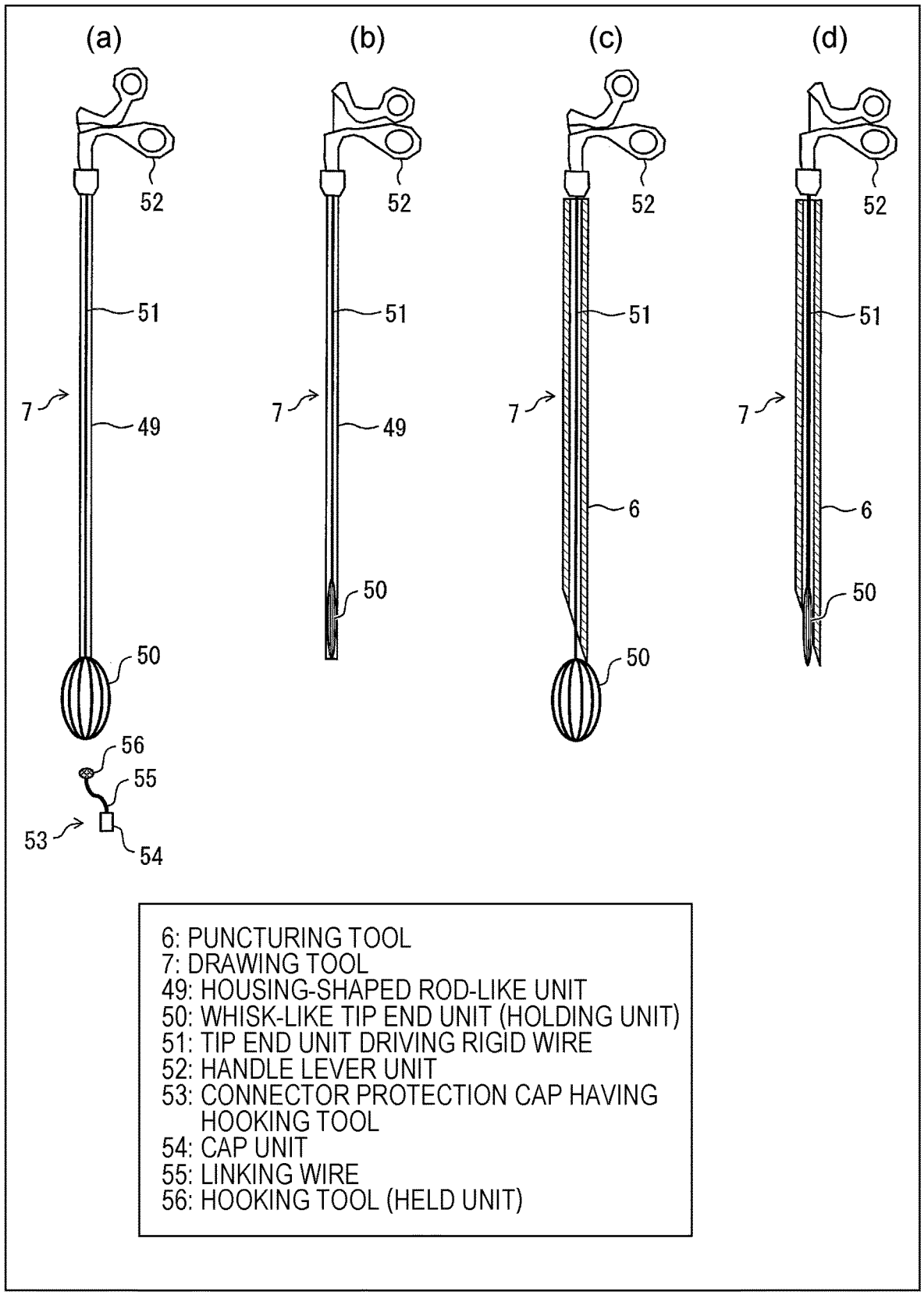
FIGS. 24(a) to 24(d) are views illustrating an example of an auxiliary tool set according to Embodiment 4.
Figure 25:
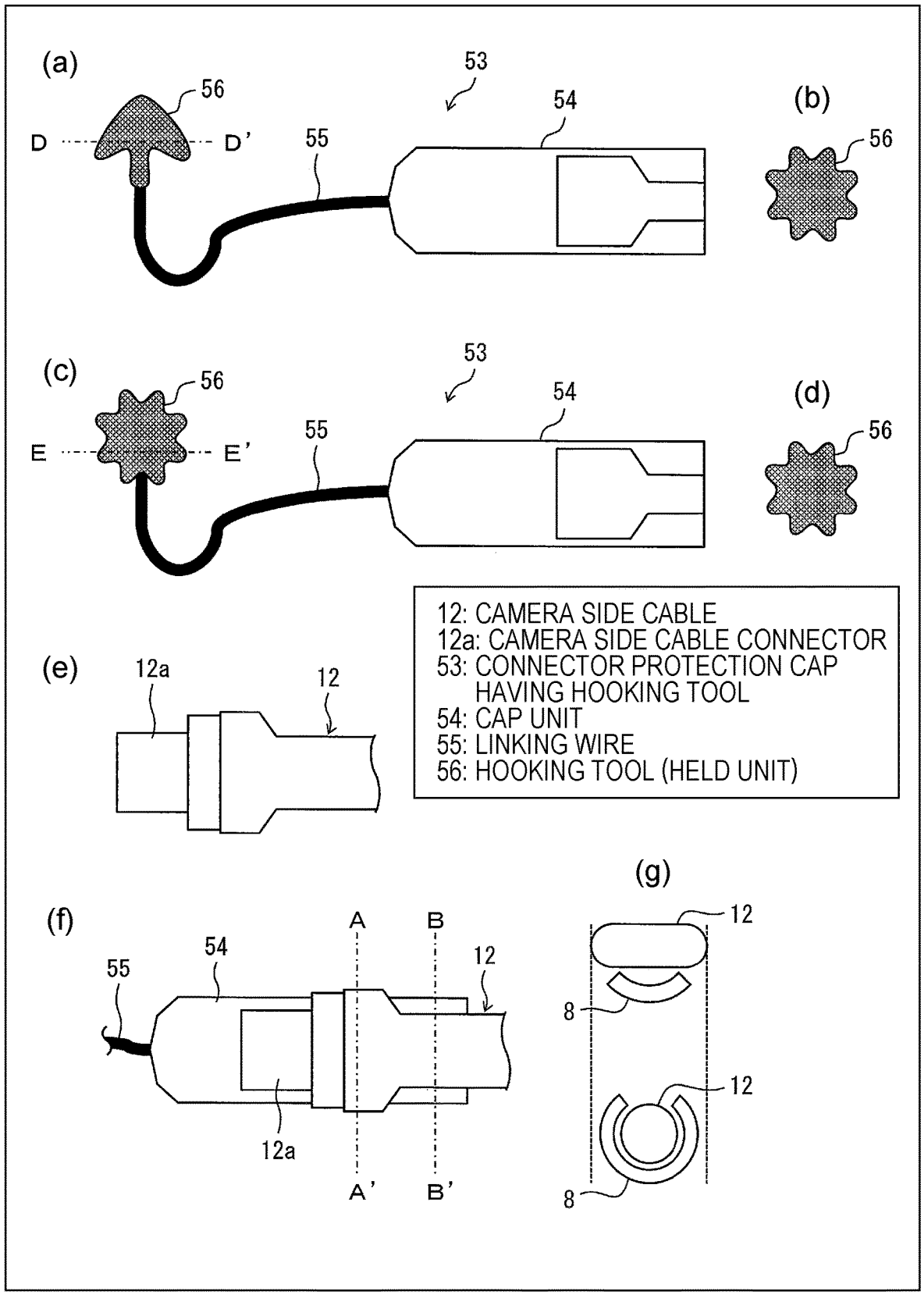
FIG. 25(a) is a view illustrating an example of the connector protection cap having a magnet and a hooking tool.
FIG. 25(b) is a sectional view taken along line D-D' of FIG. 25(a)
FIG. 25(c) is a view illustrating another example of the connector protection cap having a magnet and a hooking tool.
FIG. 25(d) is a sectional view taken along line E-E' of FIG. 25(c)
FIG. 25(e) is a view illustrating a connector unit of the camera cable.
FIG. 25(f) is a view illustrating a state where the connector protection cap having a magnet is mounted on the camera cable connector unit.
FIGS. 25(g) and 25(h) are views respectively illustrating a section taken along line A-A' and a section taken along line B-B' of FIG. 25(f).
Figure 39:
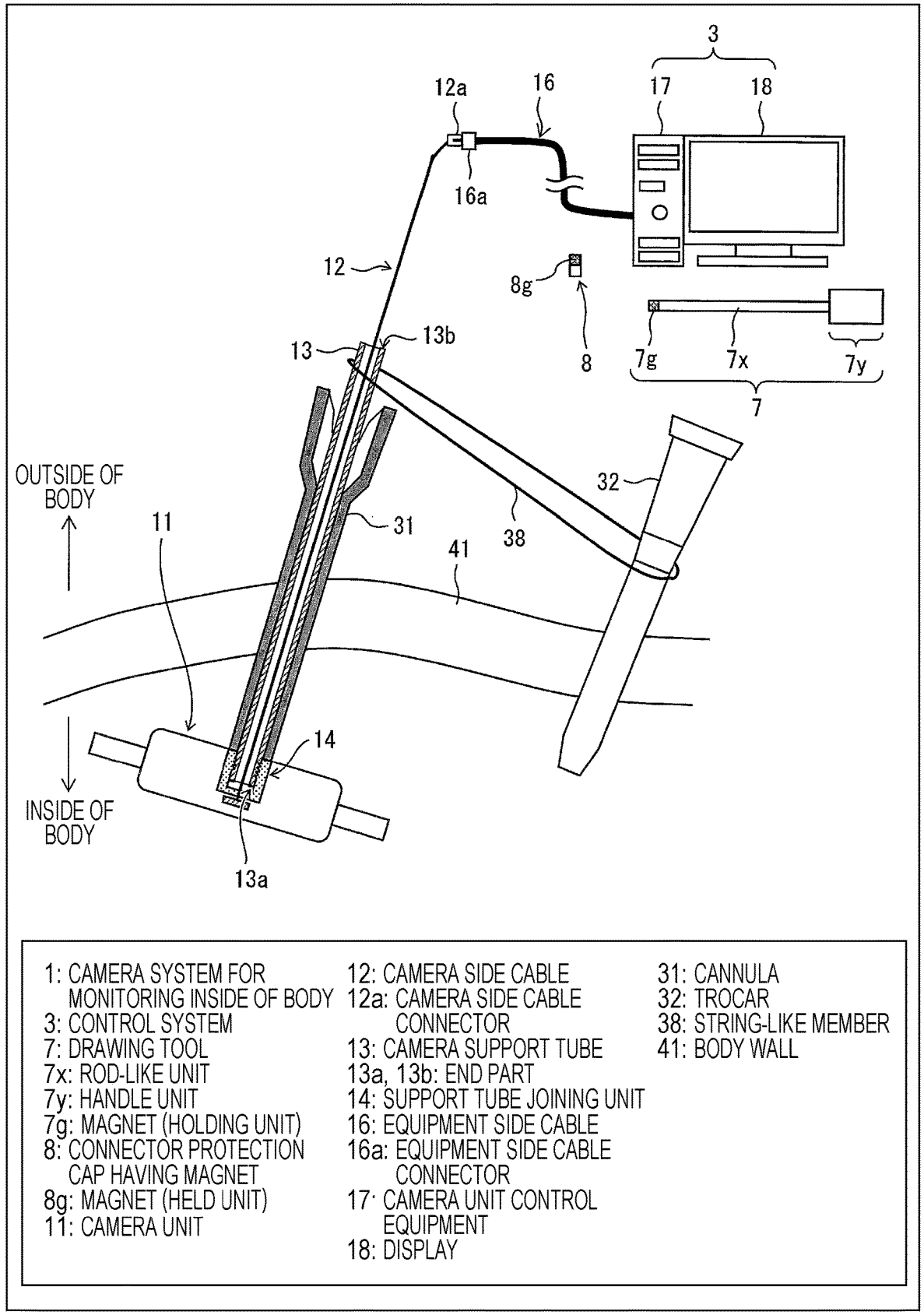
FIG. 39 is a schematic view illustrating a method for fixing the camera support tube to the body.

In addition, in FIG. 23, a case where the adhesive tape 46 is used in fixing the camera side cable 12 or the camera support tube 13, or the cannula 31, is described. However, the fixing tool is not limited thereto, and as illustrated in FIG. 39, by hooking a string-like member 38 (fixing tool) which makes a wheel to the trocar 32 and the camera support tube 13, it is possible to fix the camera support tube 13 to the body wall 41 in a desirable state (the length by which being guided toward the inside of the body, the rotational direction, and the inclination).

In this case, the string-like member fixing unit (for example, a fixing unit which can fix the string-like member 38 by making the string-like member 38 pass or by binding the string-like member) which prevents the movement of the string-like member in the axial direction of the camera support tube 13 may be provided in the camera support tube 13, similar effects can be obtained.

Embodiment 4

A case where the magnet is used as the drawing tool is described in Embodiments 1 to 3. In Example 4, an embodiment in which a drawing tool having a whisk-like tip end part, will be described based on FIGS. 24 to 27 as follows.

In addition, in the embodiment, mainly, differences from Embodiments 1 to 3 will be described, configuration elements which have the same functions as those of the configuration elements used in Embodiments 1 to 3 will be given the same reference numerals, and the description thereof will be omitted. In addition, in the embodiment, it is also needless to say modifications similar to those of Embodiments 1 to 3 are possible.

(Drawing Tool and Connector Protection Cap Having Magnet)

FIG. 24(a) is a sectional view illustrating a schematic configuration of the drawing tool having the whisk-like tip end part and the connector protection cap having a magnet and a hooking tool which are used in the embodiment, FIG. 24(b) is a sectional view illustrating a state where the whisk-like tip end part is accommodated in a pipe-shaped rod-like unit, FIG. 24(c) is a view illustrating a state where the puncturing device is used instead of the pipe-shaped rod-like unit with respect to FIG. 24(a), and FIG. 24(d) is a view illustrating a state where the whisk-like tip end part is accommodated in the puncturing device.

As illustrated in FIG. 24(a), the drawing tool 7 used in the embodiment is configured of a whisk-like tip end part 50 for hooking a connector protection cap having a magnet and a hooking tool 53, and a pipe-shaped rod-like unit 49 which are provided at one end part, a tip end unit driving hard wire 51, and a handle lever unit 52 provided at the other end part.

The whisk-like tip end part 50 is configured of a plurality of curved holding wires connected at two points of both ends, and has a shape of an elliptical body (rotational elliptical body). The plurality of holding wires can be deformed as the external force is applied.

In addition, as illustrated in FIG. 24(b), a structure in which the whisk-like tip end part 50 (holding unit) is drawn in toward the inside of the pipe-shaped rod-like unit 49 via the tip end unit driving hard wire 51 when operating the handle lever unit 52. In the whisk-like tip end part 50, in a state where the force is not applied, the interval between the holding wires increases as the tip end widens in a shape of a whisk, and when the lever is pulled and a force of drawing in a part thereof toward the inside of the pipe-shaped rod-like unit 49 is applied, the holding wire is deformed and accommodated inside the pipe-shaped rod-like unit 49, and the interval between the holding wires decreases. In this manner, the interval between the holding wires which configure the whisk-like tip end part 50 is variable.

More specifically, as illustrated in FIG. 24(a), when the whisk-like tip end part 50 is on the outside of the pipe-shaped rod-like unit 49, it is preferable that the interval between the holding wires is equivalent to the outer diameter of a hooking tool 56 which will be described later, or is slightly smaller than the outer diameter of the hooking tool 56. Still more specifically, it is more preferable that the interval between the holding wires when the whisk-like tip end part 50 is on the outside of the pipe-shaped rod-like unit 49 has a size which corresponds to the diameter of a groove part of the hooking tool 56 (diameter of a circle which is inscribed on the sectional shape of the hooking tool 56). Accordingly, when pushing the whisk-like tip end part 50 against the hooking tool 56, it is possible to put the hooking tool 56 into the whisk-like tip end part 50, and it is possible to prevent the hooking tool 56 from going out to the outside of the whisk-like tip end part 50.

In addition, as illustrated in FIG. 24(b), when the whisk-like tip end part 50 is on the inside of the pipe-shaped rod-like unit 49, it is preferable that the interval between the holding wires is smaller than the outer diameter of the hooking tool 56 which will be described later.

As described above, by using the pipe-shaped rod-like unit 49, it is possible to change the interval between the holding wires of the whisk-like tip end part 50.

The outer diameter during the accommodation can be smaller than the inner diameter of an inserting device, such as the needle-like puncturing device 6, the camera support tube 13, the cannula 31, or the trocar 32. In addition, the handle lever unit 52 has a dimension which is sufficiently larger than the inner diameter of the devices.

FIG. 24(c) is an example in which the puncturing device 6 which is used in puncturing may be used as it is instead of the dedicated pipe-shaped rod-like unit 49. The pipe-shaped rod-like unit 49 can use the existing pipe-like device, such as the camera support tube 13, the cannula 31, or the trocar 32. In addition, FIG. 24(d) is a view illustrating a state where the whisk-like tip end part 50 is drawn into the puncturing device 6.

FIG. 25(a) is a view illustrating an example of the connector protection cap having a magnet and a hooking tool 53. FIG. 25(b) is a sectional view taken along line D-D' of FIG. 25(a), FIG. 25(c) is a view illustrating another example of the connector protection cap having a magnet and a hooking tool, and FIG. 25(d) is a sectional view taken along line E-E' of FIG. 25(c). The connector protection cap having a magnet and a hooking tool 53 is configured of a connector protection cap unit having a magnet 54 (cable connector protection unit), a linking wire 55 (linking wire unit), and a hooking tool 56. The connector protection cap unit having a magnet 54 is connected to the hooking tool 56 via the linking wire 55.

The connector protection cap unit having a magnet 54 is a waterproof and antifouling cap of the camera side cable connector 12a illustrated in FIG. 25(e), has a recessed shape which corresponds to the shape of the camera side cable connector 12a, and as illustrated in FIG. 25(f), the connector protection cap unit having a magnet 54 is mounted being fitted at this part. FIG. 25(g) is a section taken along line A-A' of FIG. 25(f), and FIG. 25(h) is a section taken along line B-B', and illustrates a structure which is hooked and fastened by using a neck of the connector 15 therebetween, and does not fall out even when being pulled. In order to make the inner diameter and the outer diameter of the pipe-shaped rod-like unit 49, such as the puncturing device 6, as small as possible, the width of the connector protection cap unit having a magnet 54 illustrated in FIGS. 25(f) to 25(h) is equal to or smaller than the width of the intermediate cable 15 and the camera side cable 12.

The hooking tool 56 has a structure which is likely to be hooked to the whisk-like tip end part 50 of the drawing tool 7, and is unlikely to be dropped, and for example, as illustrated in FIGS. 25(a) and 25(b), a groove which corresponds to the shape of the whisk-like tip end part 50 enters in a shape of a key when viewed from the side surface, and as illustrated in FIG. 25(b) when viewed from above, a shape provided with a plurality of projected units and recessed units in the periphery. In addition, as illustrated in FIGS. 25(c) and 25(d), a projection which corresponds to the shape of the whisk-like tip end part 50 may have a shape on the entire surface. When the whisk-like tip end part 50 is pressed to the hooking tool 56, the hooking tool 56 gets in between the holding wires of the whisk-like tip end part 50, and when pulling up the whisk-like tip end part 50, the whisk-like tip end part 50 is hooked by the groove or the projection, and at the same time, the whisk-like tip end part 50 is drawn into the pipe-shaped rod-like unit 49, and according to this, the interval between the holding wires of the whisk-like tip end part 50 becomes narrow, and the whisk-like tip end part 50 can be tightly encroached on the hooking tool 56 and is not dropped.

As illustrated in FIG. 26(a), for example, the puncturing device 6 inserted into the body wall 41 passes through the puncturing device 6, the drawing tool 7 having the whisk-like tip end part 50 is guided toward the inside of the body, and the whisk-like tip end part 50 is pressed to the hooking tool 56. Since the holding wire of the whisk-like tip end part 50 has ductility, by pressing the whisk-like tip end part 50 to the hooking tool 56, the holding wire is deformed, the interval between the holding wires widens, and the hooking tool 56 gets into the middle (holding space) of the whisk-like tip end part 50. After the hooking tool 56 gents into the middle of the whisk-like tip end part 50, the shape of the holding wire returns to the original shape.

Next, while narrowing the interval between the holding wires by pulling the handle lever unit 52 and drawing in the whisk-like tip end part 50 to the pipe-shaped rod-like unit 49, as illustrated in FIG. 26(b), the hooking tool 56 is drawn in toward the inside of the puncturing device 6. As illustrated in FIG. 26(c), since the groove or the projection of the hooking tool 56 has a shape in which the holding wire of the whisk-like tip end part 50 gets in, the groove or the projection of the hooking tool 56, and the holding wire mesh with each other, and are held in a state where the hooking tool 56 is certainly stabilized in the puncturing device 6. Accordingly, without being hooked and coming off at the opening end part of the puncturing device 6, the holding wires can smoothly pass. In this manner, the holding wire of the whisk-like tip end part 50 forms the holding space, and can hold the hooking tool 56 on the inside of the holding space.

Next, as illustrated in FIG. 26(d), further, the drawing tool 7 is pulled up, and the connector protection cap unit having a magnet 54, the camera side cable connector 12a, and the camera side cable 12, which are in the puncturing device 6, can be guided toward the inside thereof. Accordingly, the reduction of the installation time can be achieved.

In addition, in order to realize the minimal invasiveness, it is preferable that the outer diameter of the puncturing device 6 is small. Specifically, it is preferable that the outer diameter is equal to or less than 3 mm.

FIG. 27(a) is a view illustrating still another example of the connector protection cap having a magnet and a hooking tool 53. As illustrated in FIG. 27(a), a configuration in which the hooking tool 56 connected to the connector protection cap having a magnet is small, and the linking wire 55 is longer than the puncturing device 6, is employed. Since the size of a part of the hooking tool 56 is small, as illustrated in FIG. 27(b), the puncturing device 6 having a smaller diameter can be used. In addition, since the linking wire 55 is longer than the puncturing device 6, as illustrated in FIG. 27(c), a part of the hooking tool 56 can be drawn out from the puncturing device 6 in advance. Since the camera side cable connector 12a is greater than the inner diameter of the puncturing device 6, the pulling-up is stopped at this position, but fixing is performed by the stopper 77.

Although not illustrated hereinafter, next, the camera side cable connector 12a part of the end part of the camera side cable 12 is drawn out to the outside of the body for each puncturing device 6. Since the camera side cable 12 is fixed by the stopper 77, the camera side cable 12 is prevented from being mistakenly dropped on the inside of the body when drawing out the puncturing device 6.

The diameter of the camera side cable connector 12a is slightly large to be approximately 3 mm, but the area is small, the body wall 41 can pass through the hole of the body wall while temporarily widening the hole. Accordingly, the diameters of the puncturing device 6 and the camera side cable 12 can be approximately 2 mm. Therefore, the wound of an installation unit of the camera unit 11 can be the minimum, and more minimal invasiveness can be achieved.

Next, after the temporary stopping by the cable fastener 43, the stopper 77 is removed, and the puncturing device 6 is extracted from the linking wire 55.

Figure 26:
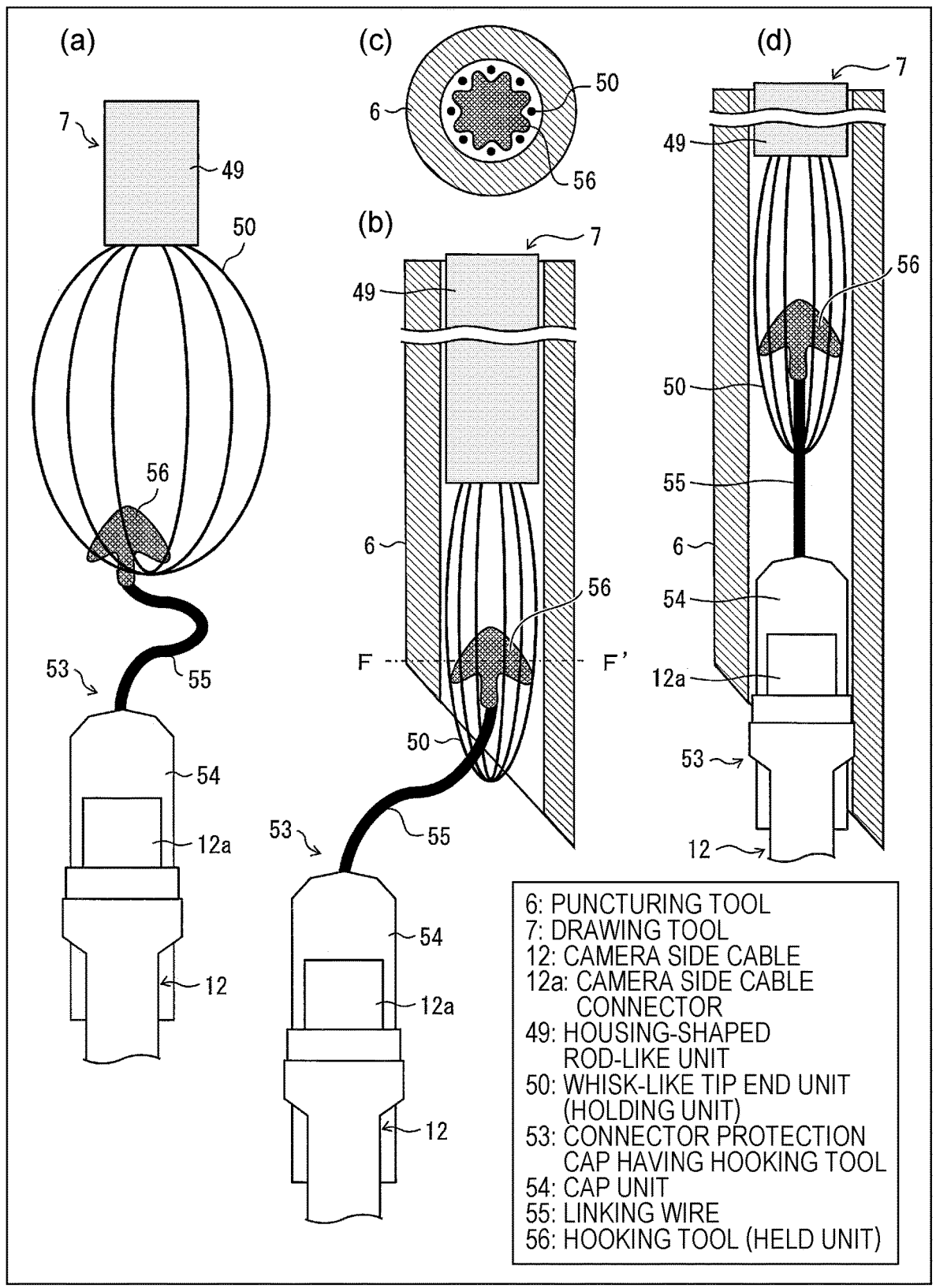
FIG. 26(a) is a view illustrating a state where the whisk-like tip end part of the drawing tool is hooked to the hooking tool of the connector protection cap having a magnet.
FIG. 26(b) is a view illustrating a state of being drawn into the puncturing device through which the tip end part has already passed, from a state of FIG. 26(a)
FIG. 26(c) is a sectional view taken along line F-F' of FIG. 26(b)
FIG. 26(d) is a view illustrating a state where the drawing tool is further pulled up, and the connector protection cap having a magnet and the connector unit are inserted into the puncturing device.
Figure 27:
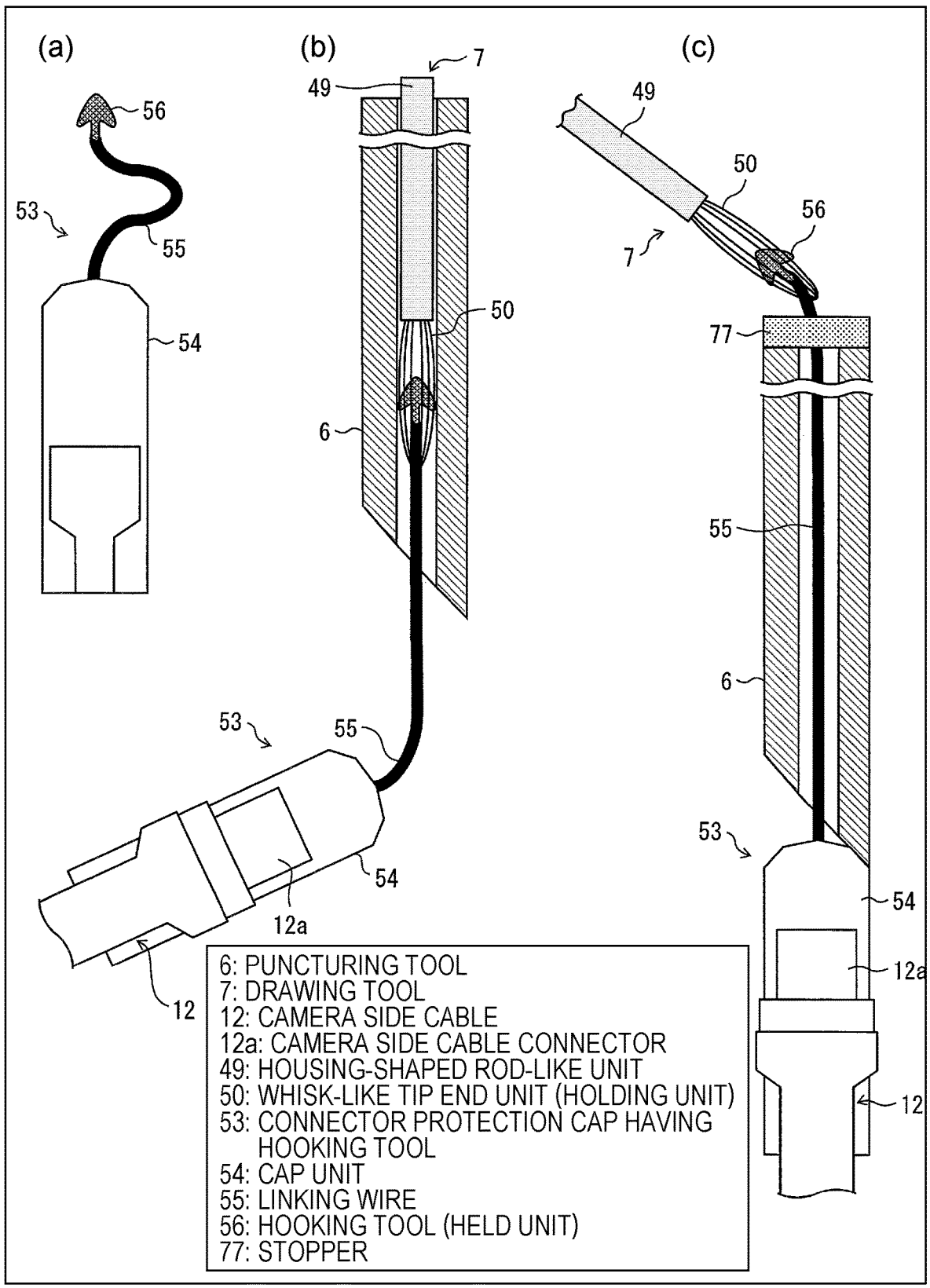
FIG. 27(a) is a view illustrating still another example of the connector protection cap having a magnet and a hooking tool.
FIG. 27(b) is a view illustrating a state where the hooking tool connected to the connector protection cap having a magnet of FIG. 27(a) is hooked to the whisk-like tip end part of the drawing tool, and is drawn into the puncturing device.
FIG. 27(c) is a view illustrating a state where the hooking tool connected to the connector protection cap having a magnet is drawn out toward the outside of the body through the puncturing device.

In addition, in the examples illustrated in FIGS. 26 and 27, a configuration in which the interval between the holding wires is changed as the whisk-like tip end part 50 is drawn in toward the inside of the pipe-shaped rod-like unit 49, by using the pipe-shaped rod-like unit 49, is described, but the invention is not limited thereto. As illustrated in FIGS. 24(c) and 24(d), without using the pipe-shaped rod-like unit 49, the interval between the holding wires may be changed as the whisk-like tip end part 50 is drawn in toward the inside of the puncturing device 6. In this case, since the pipe-shaped rod-like unit 49 is not necessary, it is possible to further reduce the light of the puncturing device 6.

In addition, in the above-described example, the whisk-like tip end part is used in the hooking method, but the invention is not limited thereto, and a shape which widens to a wide range in a shape of a net, and a small shape which can be accommodated, may be employed.

The interval between the holding wires at the center part of the whisk-like tip end part 50 is greater than the interval between the holding wires at the end part of the whisk-like tip end part 50.

In order to easily and stably hold the hooking tool 56 on the inside of the holding space, it is preferable that the interval (the size of the opening unit of the holding space) between the holding wires is constant. Therefore, instead of the whisk-like tip end part, it is preferable to use a mesh-like tip end unit made of lattice having a size which corresponds to the outer diameter of the hooking tool 56. If the mesh-like holding wire is used, the interval between the holding wires is constant, and thus, it is possible to more easily and stably hold the hooking tool 56 on the inside of the holding space.

In a medical apparatus of PTL 2, in order to draw out the communication cable toward the inside of the body, it is necessary to perform a difficult operation, such as hooking the wire to a hook unit on the inside of the body.

Meanwhile, in the camera system for monitoring the inside of a body of the embodiment, since the whisk-like tip end part 50 is provided with the plurality holding wires, and the holding wires are formed in the holding space, by guiding the hooking tool 56 toward the inside of the holding space, it is possible to hold the hooking tool 56 at the tip end of the drawing tool 7 on the inside of the body. Therefore, it is possible to easily draw out the camera side cable connector 12a toward the outside of the body.

[Regarding Each of Above-Described Embodiments]

The cannula described in each embodiment is merely an example of the tube-like device (tube-like device, tube-like member, bushing), and the cannulas can be used instead of the trocar which is the same tube-like device (tube-like device, tube-like member, bushing).

CONCLUSION

A camera system for monitoring the inside of a body (1) according to aspect 1 of the present invention, includes: an imaging part (camera unit 11) for monitoring the inside of a body; a cable (camera side cable 12) which is connected to the imaging part, and is drawn out toward the outside of the body through a port opened on the body wall; a control system (3) which is provided on the outside of the body, is connected to the cable, and includes at least a display apparatus (display 18); and a drawing tool which guides the imaging part and the cable toward the inside of the body, and is used for drawing out the cable end part toward the outside of the body.

The camera system for monitoring the inside of a body (1) according to aspect 2 of the present invention, in the above-described aspect 1, includes an imaging part (camera unit 11) including a support tube (camera support tube 13) in which one end part 13a is guided toward the inside of the body, and a joining unit (support tube joining unit 14) joined to the support tube on the inside of the body. In addition, as the support tube 13, the puncturing device 6 may be used.

In the camera system for monitoring the inside of a body (1) according to aspect 3 of the present invention, in the above-described aspect 2, a bushing (cannula 31) having a tube-like structure which can insert the support tube on the inside may be provided and fixed to the bushing on the outside of the body, and the fixing member may fix the support tube by fixing the bushing to the body surface.

A method for installing a camera system for monitoring the inside of a body according to aspect 4 of the present invention, includes: a process of opening a hole on the body wall at an imaging part installation position of the camera system for monitoring the inside of a body, by using the needle-like puncturing device, from the outside of the body; a process of guiding the imaging apparatus toward the inside of the body; a process of forcing out the drawing tool from the tip end of the pipe-like puncturing device inserted into the body; a process of gripping the tip end part of the camera side cable on the inside of the body, and adhering the tip end part to the drawing tool, by using the gripping forceps inserted from the outside of the body; a process of drawing out the drawing tool, and drawing out the end part of the camera side cable toward the outside of the body; a process of fixing the drawn-out cable on the outside of the body; and a process of electrically connecting the cable to the control system (3) on the outer side of the body including at least the display apparatus (display 18).

The method for installing the camera system for monitoring the inside of a body according to aspect 5 of the present invention, in the above-described aspect 4, further includes a process of making one end part 13a pass through the support tube (camera support tube 13) guided toward the inside of the body after drawing out the cable guided toward the inside of the body toward the outside of the body; a process of joining the imaging part and the support tube to each other by a joining unit (support tube joining unit 14) provided in the imaging part, on the inside of the body; and a process of adjusting the length of the support tube, the rotational direction of the support tube, and the inclination of the support tube with respect to the body surface, on the inside of the body, and directly or indirectly fixing the support tube to the body surface.

The method for installing the camera system for monitoring the inside of a body according to aspect 6 of the present invention, in the above-described aspect 4, further includes a process of joining the imaging part and the puncturing device by the joining unit (support tube joining unit 14) provided in the imaging part using the puncturing device 6 as the support tube (camera support tube 13) after drawing out the cable guided toward the inside of the body toward the outside of the body, on the inside of the body; and a process of adjusting the length of the support tube, the rotational direction of the support tube, and the inclination of the support tube with respect to the body surface, on the inside of the body, and directly or indirectly fixing the support tube to the body surface.

The method for installing the camera system for monitoring the inside of a body according to aspect 7 of the present invention, in the above-described aspect 5 or 6, includes a process of guiding the bushing (cannula 31) which having a tube-like structure which can insert the support tube and the puncturing device therein, together with the puncturing device 6, when opening the body wall.

Summary of Embodiments

A camera system for monitoring the inside of a body (1) according to aspect 1A of the present invention, includes: an imaging part (camera unit 11) for monitoring the inside of a body; a control system (3) which is provided on the outside of the body, and includes at least a display apparatus (display 18); a cable (camera side cable 12) in which one end is connected to the imaging part; and an auxiliary tool (auxiliary tool set) for drawing out the other end of the cable toward the outside of the body from the inside of the body, and the auxiliary tool includes a rod-like unit, a holding unit (magnet 7g) provided in the rod-like unit, and a held unit (connector protection cap having a magnet 8) connected to the other end of the cable, and the held unit is held by the holding unit by the magnetic force, on the inside of the body.

In the camera system for monitoring the inside of a body according to aspect 2A of the present invention, in the above-described aspect 1A, at least any one of the holding unit and the held unit may have a magnet.

In the camera system for monitoring the inside of a body according to aspect 3A of the present invention, in the above-described aspect 2A, the holding unit may be provided with a magnet, and the held unit may be provided with a magnetic body.

In the camera system for monitoring the inside of a body according to aspect 4A of the present invention, in the above-described aspect 3A, the magnet and the magnetic body may be a biocompatible material, or the surface may be covered with the biocompatible material.

In the camera system for monitoring the inside of a body according to aspect 5A of the present invention, in the above-described aspect 4A, the surface of the magnetic body may be covered with the biocompatible material, the held unit may have an absorbed unit which is a part of which the thickness is thinner than that of the biocompatible material, and the held unit may be held by the holding unit via the absorbed unit.

In the camera system for monitoring the inside of a body according to aspect 6A of the present invention, in any of the above-described aspects 1A to 5A, one of the holding unit and the held unit may be provided with a recessed unit (magnet recessed joining unit 48), and the other one of the holding unit and the held unit may be provided with a projected unit (magnet projected joining unit 47) fitted to the recessed unit.

In the camera system for monitoring the inside of a body according to aspect 7A of the present invention, in any of the above-described aspects 1A to 6A, the outer diameter of the holding unit may be equal to or smaller than the outer diameter of the cable, and the outer diameter of the cable connector provided at the end part of the cable. Furthermore, the outer diameter of a rod-like unit may be equal to or smaller than the outer diameter of the cable, and the outer diameter of the cable connector provided at the end part of the cable.

In the camera system for monitoring the inside of a body according to aspect 8A of the present invention, in any of the above-described aspects 1A to 7A, a puncturing device (6) for providing a hole for passing through the end part of the cable on the body wall may further be provided, the puncturing device may be cylindrical, and the inner diameter of the puncturing device may be greater than the outer diameter of the holding unit and the outer diameter of the camera side cable connector (12a) provided at the end part of the cable.

In the camera system for monitoring the inside of a body according to aspect 9A of the present invention, in any of the above-described aspects 1A to 7A, a puncturing device for providing a hole for passing through the end part of the cable on the body wall may further be provided, the puncturing device may be cylindrical, and the diameter of the puncturing device may be equivalent to the outer diameter of the cable.

In the camera system for monitoring the inside of a body according to aspect 10A of the present invention, in the above-described aspect 8A or 9A, the puncturing device may function as a support tube (camera support tube 13) which supports the imaging part as being fixed to the imaging part.

A camera system for monitoring the inside of a body according to aspect 11A of the present invention, includes: an imaging part for monitoring the inside of a body; a control system which is provided on the outside of the body, and includes at least a display apparatus; a cable in which one end is connected to the imaging part; and an auxiliary tool for drawing out the other end of the cable toward the outside of the body from the inside of the body, the auxiliary tool includes a rod-like unit, a holding unit (whisk-like tip end part 50) provided at the tip end of the rod-like unit, and a held unit (connector protection cap having a magnet and a hooking tool 53) connected to the other end of the cable, the holding unit includes a plurality of holding wires of which the intervals therebetween is variable, and the plurality of holding wires forms a holding space for holding the held unit on the inside.

In the camera system for monitoring the inside of a body according to aspect 12A of the present invention, in any one of the above-described aspects 1A to 11A, the held unit may be provided with the cable connector protection unit connected to the end part of the cable, a contact unit (magnet 8g, hooking tool 56) which comes into contact with the holding unit, and a linking wire unit (linking wire 8w, linking wire 55) which connects the cable connector protection unit and the contact unit to each other.

In the camera system for monitoring the inside of a body according to aspect 13A of the present invention, in the above-described aspect 12A, a puncturing device for providing a hole for passing through the end part of the cable on the body wall may further be provided, and the length of the linking wire unit may be longer than the length of the puncturing device.

An auxiliary tool (auxiliary tool set) according to aspect 14A of the present invention, which is used for installing the imaging part on the inside of the body, in a camera system for monitoring the inside of a body (1) provided with an imaging part (camera unit 11) which is disposed on the inside of a body and monitors the inside of a body, a control system (3) which is provided on the outside of the body, and includes at least a display apparatus (display 18), and a cable (camera side cable 12) in which one end is connected to the imaging part, including: a rod-like unit, a holding unit (magnet) provided in the rod-like unit, and a held unit connected to the other end of the cable, and on the inside of the body, the held unit (connector protection cap having a magnet 8) is held by the holding unit by the magnetic force.

A method for installing a camera system for monitoring the inside of a body according to aspect 15A of the present invention is a method for installing a camera system for monitoring the inside of a body, including an imaging part for monitoring the inside of a body, a control system which includes at least a display apparatus, and a cable in which one end is connected to the imaging part, includes: a process of guiding the imaging part, the cable, and the held unit connected to the other end of the cable, toward the inside of the body via a first hole provided on the body wall; a process of guiding a rod-like member and a holding unit provided in the rod-like member toward the inside of the body, via a second hole provided on the body wall; a process of making the holding unit and the held unit close to each other, and holding the held unit by the holding unit by the magnetic force, on the inside of the body; a process of drawing out the end part of the cable toward the outside of the body by drawing out the rod-like member from the second hole; and a process of electrically connecting the cable to the control system on the outside of the body.

The method for installing a camera system for monitoring the inside of a body according to aspect 16A of the present invention, in the above-described aspect 15A, may further include: a process of providing the second hole on the body wall by using the pipe-like puncturing device which disposes the rod-like member on the inside.

The method for installing a camera system for monitoring the inside of a body according to aspect 17A of the present invention, in the above-described aspect 16A, may further include: a process of connecting the imaging part and the support tube for fixing the imaging part to each other on the inside of the body; a process of adjusting at least one selected from a group made of the length of the support tube, the rotational direction of the support tube, and the inclination of the support tube with respect to the body surface; and a process of directly or indirectly fixing the support tube to the body surface.

In the method for installing a camera system for monitoring the inside of a body according to aspect 18A of the present invention, in the above-described aspect 17A, the puncturing device may be used as the support tube.

In the method for installing a camera system for monitoring the inside of a body according to aspect 19A of the present invention, in any one of the above-described aspects 16A to 18A, the held unit may be connected to the cable via a linking wire unit, and the length of the linking wire unit may be longer than the length of the puncturing device, and after drawing out the rod-like member from the second hole, and after drawing out the held unit toward the outside of the body, the puncturing device may be drawn out from the body wall, and the end part of the cable may be drawn out toward the outside of the body.

As described above, the camera system for monitoring the inside of a body, includes: an imaging part for monitoring the inside of a body; a control system which is provided on the outside of the body, and includes at least a display apparatus; a cable in which one end is connected to the imaging part; a first auxiliary tool which is connected to the other end of the cable; and a second auxiliary tool which includes a holding unit which holds a held unit provided in the first auxiliary tool, and a rod-like unit connected to the holding unit, and which draws out the held unit toward the outside of the body from the inside of the body through the inside of a tube-like device in which one end is guided toward the inside of the body, in a state of being held by the holding unit.

In the next configuration of the camera system for monitoring the inside of a body, the held unit is held by the holding unit by a magnetic force.

In the next configuration of the camera system for monitoring the inside of a body, one of the holding unit and the held unit has a magnet and the other one of the holding unit and the held unit has a magnetic body, and in a state where the holding unit holds the held unit, an end surface of the magnet and an end surface of the magnetic body face each other.

In the next configuration of the camera system for monitoring the inside of a body, in a state where the holding unit holds the held unit, the end surface of the holding unit and the end surface of the held unit come into contact with each other.

In the next configuration of the camera system for monitoring the inside of a body, shapes of each of the end surface of the holding unit and the end surface of the held unit are equivalent to each other.

In the next configuration of the camera system for monitoring the inside of a body, in a state where the holding unit holds the held unit, the end surface of the holding unit and the end surface of the held unit come into contact with each other so that outer circumferences overlap each other.

In the next configuration of the camera system for monitoring the inside of a body, gravity center positions of end surfaces of each of the magnet and the magnetic body are on an axis of the cylindrical holding unit or on an axis of the cylindrical held unit.

In the next configuration of the camera system for monitoring the inside of a body, connection strength between the first auxiliary tool and the other end of the cable is greater than holding strength between the holding unit and the held unit.

In the next configuration of the camera system for monitoring the inside of a body, at least one end surface and a side surface of the magnet and the magnetic body are covered with a biocompatible coating material or cover material, and the thickness of the coating material or the cover material of the end surface is less than that on the side surface.

In the next configuration of the camera system for monitoring the inside of a body, a movable member which movably blocks a tube hole is provided between an opening on the outside of the body and an opening on the inside of the body of the tube-like device, and a first distance>a second distance×(⅔) in the first auxiliary tool when a distance from a joint of the movable member to an opening on the outside of the body is the second distance regardless of the outer shape from the end surface of the held unit to the first distance.

In the next configuration of the camera system for monitoring the inside of a body, at least a part of surfaces of each of the holding unit and the held unit has a color which corresponds to visible light having a wavelength of 420 nm to 570 nm.

In the next configuration of the camera system for monitoring the inside of a body, at least a part of the surfaces of each of the holding unit and the held unit is formed of a light-storing material or a reflective material.

In the next configuration of the camera system for monitoring the inside of a body, the holding unit is provided with a plurality of holding wires in which the interval therebetween varies, and the plurality of holding wires form a holding space for holding the held unit on the inside thereof.

In the next configuration of the camera system for monitoring the inside of a body, one end part is guided toward the inside of the body, and the end part is provided with a support tube joined to the imaging part.

In the next configuration of the camera system for monitoring the inside of a body, a cable fastener which fastens the cable is provided in the support tube, and fastening strength of the cable fastener is greater than joining strength between the support tube and the imaging part.

In the next configuration of the camera system for monitoring the inside of a body, a slit which reaches from the one end part to the other end part is formed in the support tube.

In the next configuration of the camera system for monitoring the inside of a body, a fixing tool which directly or indirectly fixes the support tube to the body in a state where the length of the support tube on the inside of the body, the rotational direction of the support tube, and the inclination of the support tube with respect to the body surface, which are set by a practitioner, are held, is further provided.

In the next configuration of the camera system for monitoring the inside of a body, a cooling system which cools the support tube which transfers heat generated in the imaging part, is further provided.

In the next configuration of the camera system for monitoring the inside of a body, the support tube and the imaging part are joined to each other by the joining unit provided in the imaging part, and a heat conductive body which transfers the heat from a heat generating member included in the imaging part to the joining unit, is provided.

In the next configuration of the camera system for monitoring the inside of a body, the support tube and the imaging part are joined to each other by the joining unit provided in the imaging part, and the recessed joining unit has a heat transferring projected unit having heat transferring properties on the bottom part, and the inner circumferential surface of the support tube and the heat transferring projected unit come into contact with each other when the imaging part and the support tube join with each other.

In the next configuration of the camera system for monitoring the inside of a body, a recessed cable connector is provided at the other end of the cable.

In the next configuration of the camera system for monitoring the inside of a body, an additional cable connected to the control system is provided, and the cable connected to the imaging part and the additional cable connected to the control system, are connected to each other via an intermediate cable.

In the next configuration of the camera system for monitoring the inside of a body, a part which makes a projection at an edge of the slit of the support tube is included, and the width of a part of the slit which corresponds to the part that makes the projection becomes smaller than the diameter of the cable.

In the next configuration of the camera system for monitoring the inside of a body, the end surface of the holding unit and the end surface of the held unit have a circular shape.

In the next configuration of the camera system for monitoring the inside of a body, the difference between the outer diameter of the end surface of the magnet and the outer diameter of the end surface of the magnetic body is equal to or less than 30 percent with respect to the outer diameter of the end surface of the magnet.

In the next configuration of the camera system for monitoring the inside of a body, the magnet is included in the holding unit, and the magnetic body which is not a magnet is included in the held unit.

In the next configuration of the camera system for monitoring the inside of a body, the connection strength of the first auxiliary tool and the other end of the cable is a range of 4 N to 10 N.

In the next configuration of the camera system for monitoring the inside of a body, the holding strength of the holding unit and the held unit is a range of 0.5 N to 4 N.

In the next configuration of the camera system for monitoring the inside of a body, the fastening strength of the cable fastener is a range of 5 N to 50 N.

In the next configuration of the camera system for monitoring the inside of a body, the first auxiliary tool includes a cap unit which protects the other end of the cable, and the total length between the cap unit and the held unit provided on the cap unit is a range of 32 mm to 50 mm.

In the next configuration of the camera system for monitoring the inside of a body, a first part and a second part which is narrower than the first part further on the tip end side than the first part are included in a connector provided at the other end of the cable, when the first auxiliary tool is fitted to the second part of the connector, the outer circumference of the end surface of the first auxiliary tool matches the outer circumference of the first part of the connector, and the total length of the length of the first auxiliary tool and the length of the first part of the connector is equal to or greater than 32 mm.

In the next configuration of the camera system for monitoring the inside of a body, the total length of the length of the first auxiliary tool and the length of the first part of the connector is the first distance, and is greater than the second distance×(⅔).

An auxiliary tool set which is used in a camera system for monitoring the inside of a body provided with an imaging part which is disposed on the inside of a body and monitors the inside of a body, a control system which is provided on the outside of the body, and includes at least a display apparatus, and a cable in which one end is connected to the imaging part, includes: a first auxiliary tool which is connected to the other end of the cable; and a second auxiliary tool which includes a holding unit which holds a held unit provided in the first auxiliary tool, and a rod-like unit connected to the holding unit, and which draws out the held unit toward the outside of the body from the inside of the body through the inside of a tube-like device in which one end is guided toward the inside of the body, in a state of being held by the holding unit.

The present invention is not limited to each of the above-described embodiments, various changes are possible within the range described in claims, and an embodiment which can be obtained by appropriately combining technical means which are respectively disclosed in different embodiments is also included in the technical range of the present invention. Furthermore, by combining the technical means which are respectively disclosed in each embodiment, it is possible to form new technical characteristics.

INDUSTRIAL APPLICABILITY

The present invention can be appropriately employed in endoscopic surgery or the like.

REFERENCE SIGNS LIST

1 CAMERA SYSTEM FOR MONITORING INSIDE OF BODY
3 CONTROL SYSTEM
6 PUNCTURING DEVICE (TUBE-LIKE DEVICE)
7 DRAWING TOOL (FIRST AUXILIARY TOOL, ROD-LIKE MEMBER)
7g MAGNET (HOLDING UNIT)
7h HOLDING UNIT
7x ROD-LIKE UNIT
7y HANDLE UNIT
8 CONNECTOR PROTECTION CAP HAVING A MAGNET (SECOND AUXILIARY TOOL)
8g MAGNET (HELD UNIT)
8h HELD UNIT
8c CAP UNIT
11 CAMERA UNIT
12 CAMERA SIDE CABLE
12a CAMERA SIDE CABLE CONNECTOR
13 CAMERA SUPPORT TUBE (TUBE-LIKE MEMBER)
15 INTERMEDIATE CABLE
16 EQUIPMENT SIDE CABLE
16a EQUIPMENT SIDE CABLE CONNECTOR
18 DISPLAY
31 CANNULA (TUBE-LIKE DEVICE, TUBE-LIKE DEVICE)
41 BODY WALL

The invention claimed is:

1. A camera system for monitoring a body cavity, the camera system comprising:
   a camera to monitor the body cavity;
   a cable including first and second ends, the first end of the cable being connected to the camera and the second end of the cable being an opposite end of the cable from the first end;
   a first auxiliary tool having a cylindrical shape, the first auxiliary tool being structured to attach to the second end of the cable; and
   a second auxiliary tool including a rod, wherein
   the second auxiliary tool is structured to attach to the first auxiliary tool at an opposite end of the first auxiliary tool from the cable,
   the rod of the second auxiliary tool is structured to pass through a tube inserted in the body cavity,
   the first auxiliary tool includes, at a tip thereof, a first magnet having a cylindrical shape,
   the second auxiliary tool includes at a tip of the rod thereof, a second magnet having a cylindrical shape,
   the second magnet is structured to hold the first magnet by a magnetic force,
   the second auxiliary tool is structured to be capable of withdrawing the first magnet from the body cavity to an outside of a body through the tube such that the second magnet holds the first magnet, and
   in a state where the second magnet holds the first magnet, a second end surface of the second magnet which is perpendicular to a central axis of the second magnet and a first end surface of the first magnet which is perpendicular to a central axis of the first magnet face each other.

2. The camera system for monitoring a body cavity according to claim 1,
   wherein, in a state where the second magnet holds the first magnet, the second end surface of the second magnet and the first end surface of the first magnet come into contact with each other.

3. The camera system for monitoring a body cavity according to claim 2,
   wherein shapes of the second end surface of the second magnet and the first end surface of the first magnet are equivalent to each other.

4. The camera system for monitoring a body cavity according to claim 3,
   wherein, in the state where the second magnet holds the first magnet, the second end surface of the second magnet and the first end surface of the first magnet come into contact with each other so that outer circumferences overlap each other.

5. The camera system for monitoring a body cavity according to claim 1, wherein:
   a gravity center position of the first end surface of the first magnet is on the central axis of the first magnet, and
   a gravity center position of the second end surface of the second magnet is on the central axis of the second magnet.

6. The camera system for monitoring a body cavity according to claim 1, wherein connection strength between the first auxiliary tool and the second end of the cable is greater than holding strength between the second magnet and the first magnet.

7. The camera system for monitoring a body cavity according to claim 1, wherein at least one end surface and a side surface of the first magnet and the second magnet are covered with a biocompatible coating material or cover material, and a thickness of the biocompatible coating material or the cover material of the at least one end surface is less than that on the side surface.

8. The camera system for monitoring a body cavity according to claim 1,
wherein a movable member which movably blocks a tube hole is provided between an opening on the outside of the body and an opening on a body-cavity side of the tube, and a first distance is greater than a second distance×(2/3) in the first auxiliary tool when a distance from a joint of the movable member to the opening on the outside of the body is the second distance regardless of an outer shape from the first end surface of the first magnet to the first distance.

9. The camera system for monitoring a body cavity according to claim 1,
wherein at least a part of surfaces of the second magnet and the first magnet has a color which corresponds to visible light having a wavelength of 420 nm to 570 nm.

10. The camera system for monitoring a body cavity according to claim 1,
wherein at least a part of surfaces of the second magnet and the first magnet is formed of a light-storing material or a reflective material.

11. A camera system for monitoring a body cavity, the camera system comprising:
a camera to monitor the body cavity;
a cable including first and second ends, the first end of the cable being connected to the camera and the second end of the cable being an opposite end of the cable from the first end;
a first auxiliary tool having a cylindrical shape, the first auxiliary tool being structured to attach to the second end of the cable; and
a second auxiliary tool including a rod; wherein
the second auxiliary tool is structured to attach to the first auxiliary tool at an opposite end of the first auxiliary tool from the cable,
the rod of the second auxiliary tool is structured to pass through a tube inserted in the body cavity;
the first auxiliary tool includes, at a tip thereof, a first magnet having a cylindrical shape;
the second auxiliary tool includes, at a tip of the rod thereof, a second magnet having a cylindrical shape;
the second magnet is structured to hold the first magnet;
the second auxiliary tool is structured to be capable of withdrawing the first magnet from the body cavity to an outside of a body through the tube such that the second magnet holds the first magnet;
in a state where the second magnet holds the first magnet, a first end surface of the first magnet which is perpendicular to a central axis of the first magnet and a second end surface of the second magnet which is perpendicular to a central axis of the second magnet face each other.

12. A camera system for monitoring a body cavity, the camera system comprising:
a camera to monitor the body cavity;
a cable including first and second ends, the first end of the cable being connected to the camera and the second end of the cable being an opposite end of the cable from the first end;
a first auxiliary tool structured to attach to the second end of the cable; and
a second auxiliary tool including a rod, wherein
the second auxiliary tool is structured to attach to the first auxiliary tool at an opposite end of the first auxiliary tool from the cable,
the rod of the second auxiliary tool is structured to pass through a tube inserted in the body cavity,
the first auxiliary tool includes a held unit,
the second auxiliary tool includes a holding unit at a tip of the rod thereof,
the holding unit is structured to hold the held unit by a magnetic force,
the second auxiliary tool is structured to be capable of withdrawing the held unit from the body cavity to an outside of a body through the tube such that the holding unit holds the held unit, and
at least a portion of surfaces of the holding unit and the held unit has a color which corresponds to visible light having a wavelength of 420 nm to 570 nm.

* * * * *